(12) United States Patent
Park et al.

(10) Patent No.: US 8,344,041 B2
(45) Date of Patent: Jan. 1, 2013

(54) MONOMER FOR DENTAL COMPOSITIONS

(75) Inventors: Jonggu Park, Lawrence, KS (US);
Paulette Spencer, Parkville, MO (US);
Elizabeth Murphy Topp, Lawrence, KS (US); Qiang Ye, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 545 days.

(21) Appl. No.: 12/415,180

(22) Filed: Mar. 31, 2009

(65) Prior Publication Data

US 2009/0247660 A1    Oct. 1, 2009

Related U.S. Application Data

(60) Provisional application No. 61/041,401, filed on Apr. 1, 2008.

(51) Int. Cl.
*C08G 18/67* (2006.01)
*A61K 59/68* (2006.01)
*G03F 7/029* (2006.01)
*C09K 3/00* (2006.01)

(52) U.S. Cl. ............... 522/174; 522/25; 522/28; 522/30; 522/152; 252/182.13; 252/182.14; 252/182.23; 526/304; 523/118

(58) Field of Classification Search ............... 522/25, 522/28, 30, 152, 174; 526/304; 523/118; 252/180.23, 182.13, 182.14, 182.32
See application file for complete search history.

(56) References Cited

U.S. PATENT DOCUMENTS 4,302,381 A    11/1981 Omura et al.
5,658,963 A *   8/1997 Qian et al. ............... 522/14
2007/0111136 A1* 5/2007 Miyasaka et al. ......... 430/270.1

FOREIGN PATENT DOCUMENTS

KR    2009-0090866 A1    8/2009
WO    WO 2007079070 A1 *  7/2007

OTHER PUBLICATIONS

Chung, C.-M. et al., Synthesis and Photopolymerization of Trifunctional Methacrylates and Their Application as Dental Monomers, Journal of Biomedical Materials Research, 2002, pp. 622-627.
Kim, J.-G. et al., Trifunctional Methacrylate Monomers and Their Photocured Composites with Reduced Curing Shrinkage, Water Sorption, and Water Solubility, Biomaterials, 2003, pp. 3845-3851.
Kim, J.-G. et al., Elution from Light-Cured Dental Composites: Comparison of Trimethacrylate and Dimethacrylate as Base Monomers, Journal of Biomedical Materials Research, Part B, Applied Biomaterials, 2005, pp. 328-333.
International Search Report and Written Opinion dated Jan. 29, 2010 as issued in International Application No. PCT/US2009/039113 filed Apr. 1, 2009.

* cited by examiner

*Primary Examiner* — Michael Pepitone
*Assistant Examiner* — Jessica Paul
(74) *Attorney, Agent, or Firm* — Workman Nydegger

(57) ABSTRACT

A novel monomer, 1,1,1-tri-[4-(methacryloxyethylaminocarbonyloxy)-phenyl]ethane (MPE) can be used in preparing dental compositions The MPE monomer can be combined into a dental adhesive with hydroxyethyl methacrylate (HEMA) and BisGMA (bisphenol A dimethacrylate). The MPE polymer can be polymerized with a photoinitiator system, such as a system that includes an iodonium salt. The iodonium salt can be diphenyliodonium hexafluorophosphate.

30 Claims, 42 Drawing Sheets

MONOMER FOR DENTAL COMPOSITIONS

CROSS-REFERENCE TO RELATED APPLICATIONS

The present patent application claims benefit of U.S. Provisional Application Ser. No. 61/041,401 entitled "NOVEL MONOMER FOR DENTAL ADHESIVE", filed Apr. 1, 2008, which provisional application is incorporated herein by specific reference.

This invention was made with government support under R01 DE0143292 awarded by the National Institutes of Health. The government has certain rights in the invention.

BACKGROUND OF THE INVENTION

The use of restorative composites in dentistry has been primarily driven by the esthetic features of these materials. Interest in dental composites as an alternative to amalgam has been further promoted by the public's concern about mercury release from dental amalgam. Despite their extensive use, the short clinical lifetime of composites is a significant limitation. While the clinical lifetime of traditional mercury-containing dental amalgam restorations is generally 10-20 years, the lifetime for methacrylate-based composite restorations is about 8 years in anterior sites and as little as 2-4 years in posterior sites.

The primary factor in the premature failure of composite restorations is recurrent caries at the margins of these restorations. Recurrent decay is most often localized gingivally and is linked to the lack of a consistent seal at the tooth/material interface. Water in the mouth is a major interfering factor when bonding adhesives and/or composites to the tooth. The water content of the dentin surface varies as a function of depth, the nature of the substrate (i.e. caries-affected or healthy dentin) and the presence of residual rinse water.

Effective bonding at the prepared tooth/composite material interface requires dentin adhesives that provide superior properties and rapid polymerization under clinical conditions. The reactivity and the mechanical behavior are influenced by the photoinitiator system and curing conditions.

BRIEF SUMMARY OF THE INVENTION

In one embodiment, the present invention can be a monomer having Formula 1, as shown below, or a derivative thereof. The derivatives can include any hydrogen being substituted with a proper group, as described below. Also, the derivatives can include any aromatic ring being a carbocycle that is substituted or unsubstituted. Also, the alkyl groups can be longer groups, such as C3-C10 alkyl groups. Other derivatives can be used. The present invention can also include compositions having the monomer. The compositions having the monomer can include compositions configured for preparing a dental composition. Also, the monomer can be present, unpolymerized, in a dental composition, such as adhesive or prosthesis.

In one embodiment, Formula 1 is 1,1,1-tri-[4-(methacryloxyethylaminocarbonyloxy)-phenyl]ethane (MPE).

In one embodiment, a composition having MPE or derivative thereof can include one or more co-monomers. The co-monomers can be any co-monomer described herein or otherwise known. Examples of the one or more co-monomers are selected from monomers or oligomers having one or more ethylenically unsaturated groups, di-acrylates and methacrylates, tri-acrylates and methacrulates, poly-acrylates and methacrylates, 2-hydroxyethyl methacrylate (HEMA), methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, diurethane dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol ("Bis-GMA"), bis[1-(2-acryloxy)]-p-ethoxyphenyldimethylmethane, bis[1-(3-acryloxy-2-hydroxy)]-p-propoxyphenyldimethylmethane, trishydroxyethyl-isocyanurate trimethacrylate, the bis-acrylates and bis-methacrylates of polyethylene glycols of molecular weight 200-500, copolymerizable mixtures of acrylated monomers, copolymerizable acrylated oligomers, phosphoric acid derivatives and carboxylic acid derivatives of ethylenically unsaturated monomers, vinyl compounds, styrene, diallyl phthalate, divinyl succinate, divinyl adipate and divinylphthalate, and combinations thereof.

In one embodiment, the co-monomers include HEMA and BisGMA. The composition can include HEMA/BisGMA/MPE at 45/30/25 w/w ratio, or at a 35-55/20-40/15-35 w/w ratio, or at a 30-60/15-45/10-40 w/w ratio. The composition can also include ethanol. For example, the composition can include HEMA/BisGMA/MPE+40 wt % EtOH, or from 30-50% EtOH, or from 20-60% EtOH.

In one embodiment, the composition can include a photoinitiator system. The photoinitiator system can include a component selected from the group of acylphosphine oxides, bis-acyl phospine oxides, camphorquinone, benzophenone, alkyl ethers of benzoin, diphenoxy benzophenone, benzildimethylketal, halogenated functional benzophenones, amino functional benzophenones, benzils, benzimidazozles, 2-hydroxy-2-methylphenol-1-propanone, fluorenone, fluorenone derivatives, 2,2-diethoxyacetophenone, benzoin, 9,10-phenanthrenequinone, anthraquinone derivatives, 2-benzyl-2-N,N-dimethylamino-1-(f-morpholinophenyl)butanone, zanthone, zanthone derivatives, halogenated acetophenone, halogenated acetophenone derivatives, thioxanthone, thioxanthone derivatives, sulfonyl chlorides of aromatic compounds, diacetyl, furil, anisil, 4,4'-dichlorobenzil, 4,4'-dialkoxybenzil, phenylpropanedione, acylphosphine oxides, 2-(dimethylamino)ethyl methacrylate, diphenyliodonium hexafluorophosphate, ethyl-4-(dimethylamino)benzoate, or combinations thereof.

In one embodiment, the photoinitiator system can include a iodonium salt. For example, the iodonium salt can be selected from the group of diphenyliodonium hexafluorophosphate, diphenyliodonium chloride, or the like.

In one embodiment, the composition can include the photoinitiator system at a total amount of 0.001 wt % to about 10 wt %, or 0.01 wt % to about 1 wt %, or 0.1 wt % to about 1 wt %, or about 0.5 wt %.

In one embodiment, the composition can include camphorquinone at about 0.5 wt % and ethyl-4-(dimethylamino)benzoate at about 0.5 wt %). Also, the composition can include camphorquinone from about 0.1 to about 1 wt %, ethyl-4-(dimethylamino)benzoate from 0.1 to about 1 wt %, and iodonium salt from about 0.1 to about 1 wt %.

In one embodiment, the composition can include a dental composition filler.

In one embodiment, the composition is a dental composition comprising a polymer prepared from polymerizing the monomer MPE or derivative thereof. Also, the dental composition can include a polymer prepared from polymerizing one or more co-monomers. Moreover, the polymer can be prepared from with a photoinitiator system.

In one embodiment, the present invention includes a method of preparing a dental composition. Such a method can include polymerizing the monomer MPE or derivative. Depending on the type of dental composition, the MPE monomer can be polymerized in a mouth of a subject or in a laboratory or manufacture setting. The MPE or derivative thereof can be polymerized with one or more co-monomers with the monomer. Optionally, the monomer and co-monomers can be polymerized with a photoinitiator system.

In one embodiment, the method of preparing a dental composition can include using a photoinitiator system that includes a iodonium salt for polymerization. For example, the iodonium salt can be diphenyliodonium hexafluorophosphate.

In one embodiment, the present invention includes a method of making the monomer MPE. The method can include chemical synthesis of 1,1,1-tri-[4-(methacryloxyethylaminocarbonyloxy)-phenyl]ethane (MPE) by reaction of 1,1,1-tris(4-hydroxyphenyl)ethane and 2-isocyantoethyl methacrylate. FIG. 1 shows an example of the chemical synthesis.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1A:
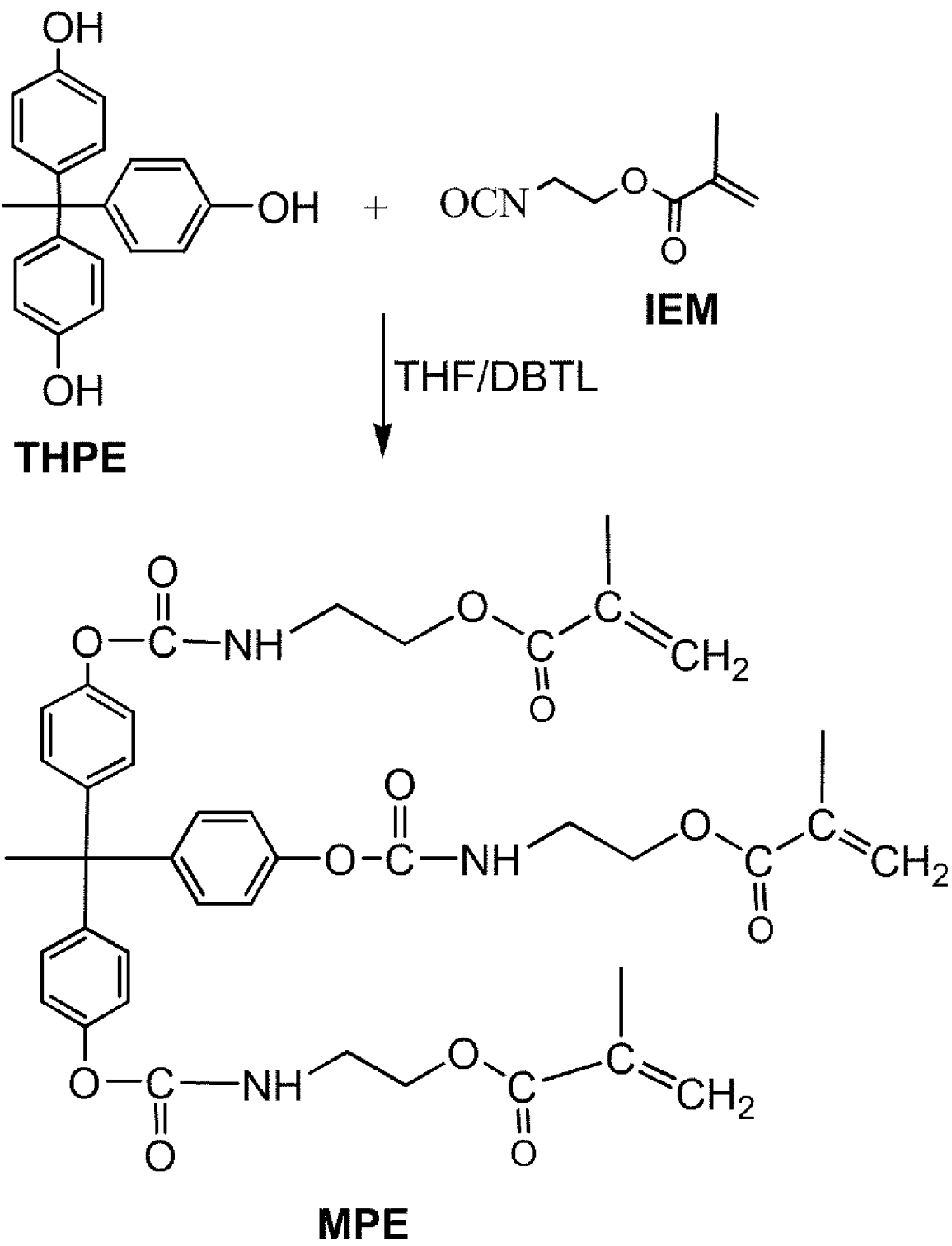
FIG. 1A is a schematic representation of a reaction scheme for synthesis of 1,1,1-tri-[4-(methacryloxyethylamino-carbonyloxy)-phenyl]ethane (MPE).

The primary factor in the premature failure of moderate to large composite restorations is recurrent caries at the margins of these restorations. Recurrent caries are most often localized gingivally and are linked to the lack of a consistent seal at the tooth/material interface. Clinicians frequently find very little enamel available for bonding at the gingival margin of class II composite restorations, and thus, the bond at this margin depends on the integrity of the seal formed with dentin. The breakdown of the bond at the dentin/adhesive/composite interfaces has been linked to the failure of current materials to develop a durable seal to dentin. Water is a major interfering factor when bonding adhesives and/or composites to the tooth. It has been shown detrimental adhesive phase separation at the interface with wet dentin and degradation of adhesive monomers or oligomers from class II composite after 3-months aqueous aging. Another factor, is the ester linkages in the methacrylate matrix. The ester groups are critical to the polymerization of the methacrylate-based adhesives, but are also subject to attack by water and salivary esterases.

I. Introduction

The structure of methacrylate adhesives suggests a general mechanism for their chemical and enzymatic degradation in oral fluids. On prolonged exposure of the restoration to oral fluids, water begins to penetrate the resin. Water initially enters the matrix by diffusion into loosely cross-linked or hydrophilic domains. The hydrophilic domain exhibits limited monomer/polymer conversion because of adhesive phase separation and lack of compatibility between the photoinitiator and hydrophilic phase. The poorly polymerized hydrophilic phase degrades rapidly in the aqueous environment. Water may also be trapped within the matrix during photopolymerization in the moist environment of the mouth. Portions of the matrix may be directly exposed to oral fluids, particularly at the gingival margin of Class II and V composite restorations. The presence of water promotes the chemical hydrolysis of ester bonds in methacrylate materials. This reaction is expected to be relatively slow at the neutral pH typical of saliva, but excursions in pH caused by foods or cariogenic bacteria may lead to transient acid or base catalysis. The carboxylate and alcohol degradation products of ester hydrolysis are more hydrophilic than the parent ester, further enhancing the local ingress of water. In addition, the carboxylate groups are anionic at normal salivary pH causing a degree of matrix swelling and strain due to charge repulsion. Over years of exposure to salivary fluids, local domains of the methacrylate network may become sufficiently degraded and/or hydrophilic to permit access by esterases, which greatly accelerate ester bond hydrolysis. Mechanical wear of the adhesive that may be exposed at the margins of the restorations may further accelerate matrix degradation by abrading the surface, increasing the surface area and allowing greater ingress of both water and enzymes.

Although many factors may contribute to the premature breakdown of methacrylate-based adhesives, the ester linkages in the methacrylate matrix can be susceptible to breakdown since these linkages are susceptible to attack by water and esterases. Each monomethatylate contributes one ester bond, and each dimethacrylate contributes two, so that ester linkages are numerous and widely distributed in the network. Esters anchor the cross-linking dimethacrylates and the pendant monomethacrylate side chains to the vinyl chains, forming critical structural bonds. When exposed to oral fluids, the ester bonds are vulnerable to two forms of hydrolytic attack: (i) chemical hydrolysis catalyzed by acids or bases, and (ii) enzymatic hydrolysis catalyzed by salivary enzymes, particularly esterases. Both require the presence of water in close association with the bond that will be hydrolyzed.

In order to inhibit the mechanism of degradation, the rate and extent of water ingress into the matrix should be minimized. This can be accomplished by the use of relatively hydrophobic monomers, by increasing cross-link density and/or by a high degree of conversion during polymerization. A drawback to this approach is the reduced water compatibility of hydrophobic monomers. In particular, it has been shown that very poor interfacial integrity with wet dentin and limited durability of the a/d bond with hydrophobic monomers. A second strategy involves selectively modifying methacrylate side chains to create branched and/or urethane functional groups that are poor esterase substrates while retaining some hydrophilic character (e.g., by balancing with incorporating polar functional groups such as hydroxyl, urethane, ether, etc.). Clearly, any change in the chemical structure intended to increase esterase resistance is likely to alter other chemical and physical properties of the matrix. The optimal adhesive will be produced by balancing the desired physical, chemical and mechanical properties of the matrix with the need for esterase resistance.

Clinically, dentin compositions are placed on the moist dentin surface and subsequently light-cured. Residual water on the dentin surface may dilute the adhesive monomers prior to polymerization, possibly influencing the formation of the polymer network and the resulting mechanical properties. Because of its small size, water is expected to penetrate into nano/micrometer-size free volume spaces between polymer chains, or cluster around functional groups that are capable of hydrogen bonding. The water penetration may alter mechanical properties observed at the macro scale. Thus, it is important to determine the mechanical properties of samples polymerized under moist conditions.

In one embodiment, the present invention provides monomers for use in preparing dental compositions, as well as the compositions themselves, for improved stability. The improved stability can be by esterase resistance of the new dental composition formed with the MPE monomer. Also, the improved stability can be obtained from increased crosslink density and/or both the intra- and intermolecular hydrogen bonds of urethane groups in the polymer matrix.

Generally, the present invention relates to a novel urethane-linked trimethacrylate monomer, dental compositions having a polymer formed from the monomer, methods of synthesis, and methods of use thereof in dental compositions. The urethane-linked trimethacrylate monomer can be used as a co-monomer in dental compositions, such as adhesives, restorations, and the like. The monomer can improve dental compositions that are formed in the presence of moisture, such as in the mouth, because dental compositions that include the new monomer have less methacrylic acid release without sacrificing polymerization conversion, penetration into dentin or mechanical properties, as compared to model adhesives that are representative of state-of-the-art commercial dentin adhesives.

Additionally, the present invention relates to a photoinitiator system that can be employed to polymerize dental compositions, such as compositions that include the novel urethane-linked trimethacrylate monomer. As such, the invention generally relates to the photoinitiator system, compositions having the photoinitiators of the system, methods of preparing the photoinitiator system, and methods of polymerizing dental compositions with the photoinitiator system.

II. MPE Monomer

Figure 1B:
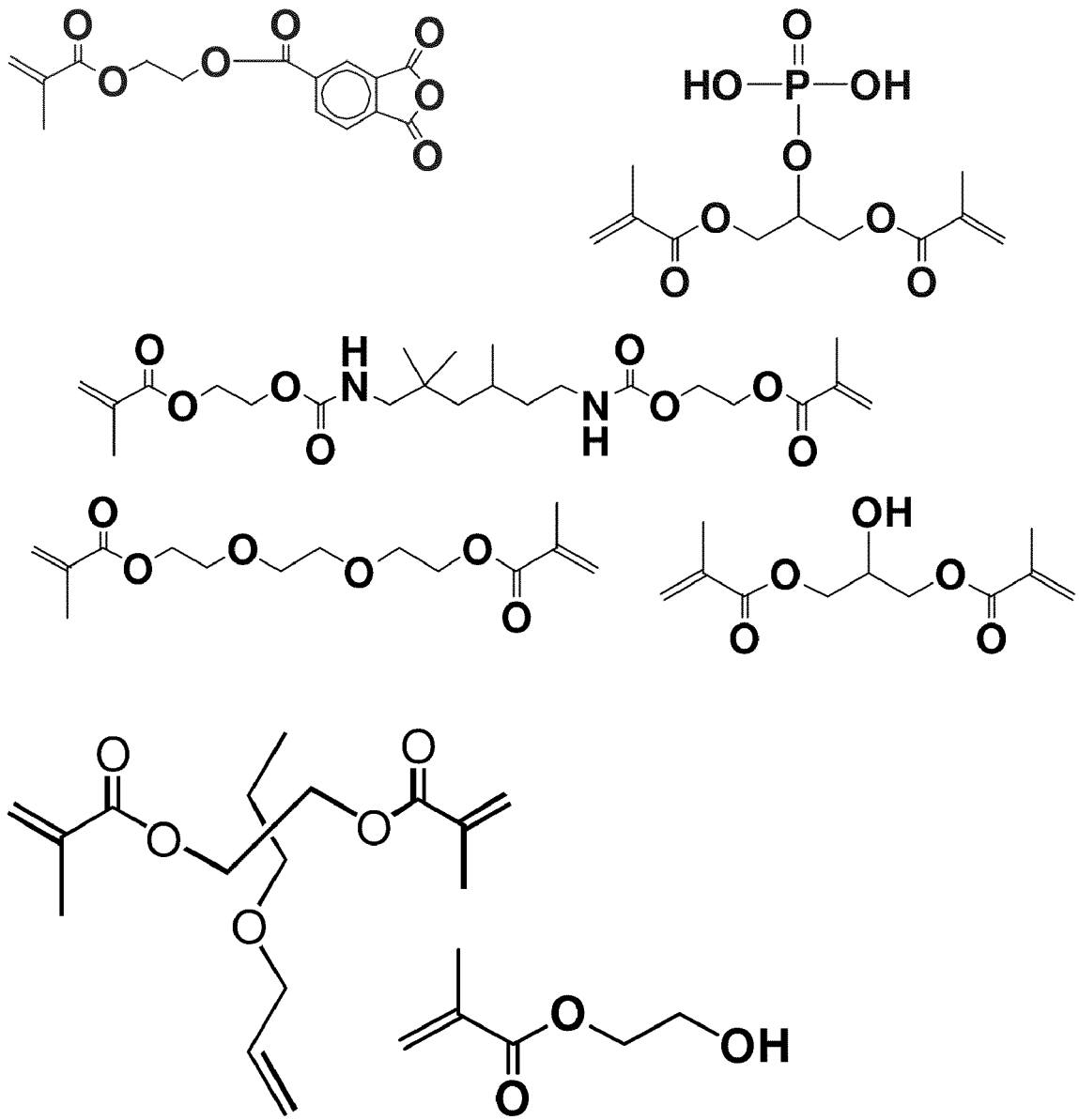
FIG. 1B shows examples of some co-monomers for dental compositions.

The structure and synthesis of the novel monomer, 1,1,1-tri-[4-(methacryloxyethylaminocarbonyloxy)-phenyl] ethane (MPE) is shown in FIG. 1A and in Formula 1 below. The MPE monomer can be formulated into a dental composition. For example, MPE can be combined into a dental adhesive with hydroxyethyl methacrylate (HEMA) and Bis-GMA (bisphenol A dimethacrylate). However, MPE can also be polymerized with other monomers, such as 4-META, GDMP, UDMA, TEGDMA, GDMA, TMPEDMA, or the like, as shown in FIG. 1B. Additionally, the novel monomer can be derivatives of MPE. The new trimethacrylate monomer, MPE, containing a urethane-linked group for use as a co-monomer in dentin adhesives was synthesized and characterized. The trifunctional MPE was readily synthesized in good yields, 90%.

In one embodiment, the monomer has a structure as shown in Formula 1 or derivative thereof.

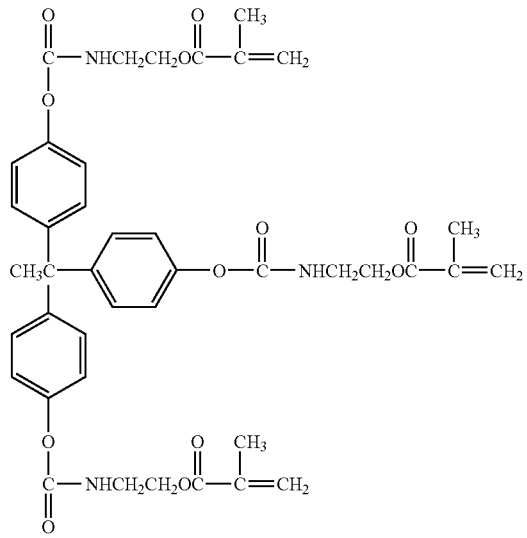

In Formula 1, any of the C═O groups can be substituted with SO, SO₂, or C═S.

In Formula 1, the aromatic ring groups can be any aromatic or carbocycle or cycloalkyl, which are aromatic, carbocyclic, and/or heterocyclic 5, 6 and 7 membered rings being mono, bi, tri, tetra, penta, hexa, hepta or octa cyclic fused rings that are substituted or unsubstituted, each heterocyclic ring can include one or more hetero atoms chosen from to O, S, N, Se, or P. Each ring can be substituted with a one ore more substituents at a para, meta, and/or ortho position. Each ring can have 1, 2, 3, 4, or 5 substituents. Each hydrogen can be substituted with aliphatic and/or aromatic substituent, defined as R1.

In one embodiment, each R1 is independently selected from the group H, F, Cl, Br, I, —OH, —CF₃, —OR2, —CN, —NO₂, NR2R2, —C(O)R2, —C(O)OR2, —OC(O)R2, —C(O)NR2R2, —NR2C(O)R2, —OC(O)NR2R2, —NR2C(O)OR2, —NR2C(O)NR2R2, —C(S)R2, —C(S)OR2, —OC(S)R2, —C(S)NR2R2, —NR2C(S)R2, —NR2C(S)R2, —OC(S)NR2R2, —NR2C(S)OR2, —NR2C(S)NR2R2, —C(NR2)R2, —C(NR2)OR2, —OC(NR2)R2, —C(NR2)NR2R2, —NR2C(NR2)R2, —OC(NR2)NR2R2, —NR2C(NR2)OR2, —NR2C(NR2)NR2R2, —S(O)$_p$R2, —SO₂NR2R2, R2, —C(NO)CH₃, —C(NO)C1-C6 alkyl, —C(NO)C(CH₃)₃, oxaziridine ring, nitrone or ozaziridine ring with C1-C6 straight or branched substituted or unsubsituted saturated or unsaturated alkyl, where p can be 0, 1, or 2, and R2 is an aromatic or an aliphatic group.

In one embodiment, when included, R2, at each occurrence, is independently selected from the group H, OH, C1-C6 alkyl, C2-C6 alkenyl, C2-C6 alkynyl, 5-7 membered saturated or unsaturated aromatic or carbocycle that is substituted or unsubstituted, 5-7 membered saturated or unsaturated aromatic or carbocycle that is substituted or unsubstituted and with one or more heteroatoms, —C(O)C1-C6 alkyl, —C(O)C2-C6 alkenyl, —C(O)C2-C6 alkynyl, —C(O)C3-C14 saturated or unsaturated aromatic or carbocycle that is substituted or unsubstituted, —C(O)C3-14 saturated or unsaturated aromatic or carbocycle that is substituted or unsubstituted and with one or more heteroatoms, —C(O)O—C1-C6 alkyl, —C(O)O—C2-C6 alkenyl, —C(O)O—C2-C6 alkynyl, —C(O)OC5-C7 saturated or unsaturated aromatic or carbocycle that is substituted or unsubstituted, —C(O)O-5-7 membered saturated or unsaturated aromatic or carbocycle that is substituted or unsubstituted or unsubstituted and with one or more heteroatoms. For example, the heteroatoms are nitrogen, oxygen, sulfur, or selenium.

In one embodiment, when substituted, R2 is substituted with R3, which at each occurrence, is independently selected from the group F, Cl, Br, OH, I, ═O, ═S, ═NR4, ═NOR4, ═N—NR4R4, —CF₃, —OR4, —CN, —NO₂, —NR4R4, —C(O)R4, —C(O)OR4, —OC (O)R4, —C(O)NR4R4, —NR4C(O)R4, —OC(O)NR4R4, —NR4C(O)OR4, —NR4C(O)NR4R4, —C(S)R4, —C(S)OR4, —OC(S)R4, —C(S)NR4R4, —NR4C(S)R4, —O C(S)NR4R4, —NR4C(S)OR4, —NR4C(S)NR4R4, —C(NR4)R4, —C(NR4)OR4, —OC(NR4)R4, —C(NR4)NR4R4, —NR4C(NR4)R4, —OC(NR4)NR4R4, —NR4C(NR4)OR4, —NR4C(NR4) NR4R4, S(O)$_p$R4, —SO₂NR4R4, —R4, —C(NO)C(CH₃)₃, oxaziridine ring, nitrone or ozaziridine ring with C1-C6 straight or branched substituted or unsubsituted saturated or unsaturated alkyl, wherein R4 is an aromatic or aliphatic group, substituted or unsubstituted.

In one embodiment, when included R4, at each occurrence, is independently selected from the group H, C1-C6 alkyl, C2-C6 alkenyl, C2-C6 alkynyl, 5-7 membered saturated or unsaturated aromatic or carbocycle that is substituted or unsubstituted, 5-7 membered member saturated or unsaturated aromatic or carbocycle that is substituted or unsubstituted and with one or more heteroatoms, —C(O)C1-C6 alkyl, —C(O)C2-C6 alkenyl, —C(O)C2-C6 alkynyl, —C(O)C5-C7 saturated or unsaturated aromatic or carbocycle that is substituted or unsubstituted, —C(O)C5-C7 saturated or unsaturated aromatic or carbocycle that is substituted or unsubstituted and with one or more heteroatoms, —C(O)O—C1-C6 alkyl, —C(O)O—C2-C6 alkenyl, —C(O)O—C2-C6 alkynyl, —C(O)OC5-C7 saturated or unsaturated aromatic or carbocycle that is substituted or unsubstituted, —C(O)OC5-C7 saturated or unsaturated aromatic or carbocycle that is substituted or unsubstituted and with one or more heteroatoms. The heteroatoms can be nitrogen, oxygen, sulfur, and selenium, or the like.

In Formula 1, each methyl group or ethyl group can include a C1-C10 alkyl, C2-C10 alkenyl, C2-C10 alkynyl, which is saturated or unsaturated and substituted or unsubstituted.

Figure 1C:
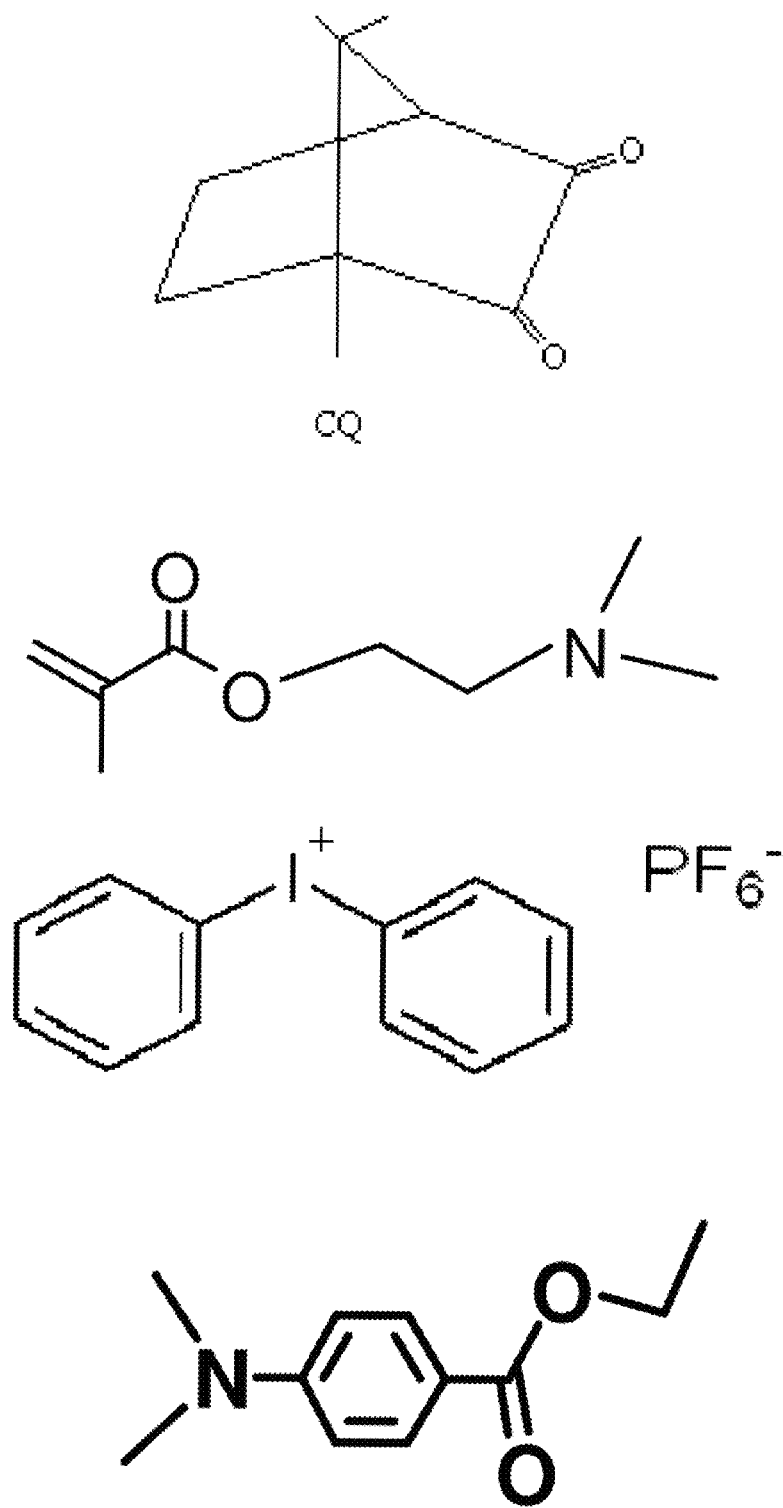
FIG. 1C shows examples of some photoinitiators.

FIG. 1C illustrates various photoinitiators that can be used to polymerize the dental composition having MPE. Examples include camphorquinone (CQ), 2-(dimethylamino)ethyl methacrylate (DMAEMA), diphenyliodonium hexafluorophosphate (DPIHP), and ethyl-4-(dimethylamino)benzoate (EDMAB), or photoinitiator combinations thereof.

The new MPE monomer and its derivatives can be synthesized by addition reaction. The MPE monomers can be prepared into dental compositions as a co-monomer that is polymerized in the presence of other dental monomers in order to prepare the dental composition. While MPE was polymerized with hydroxyethyl methacrylate (HEMA) and BisGMA (bisphenol A dimethacrylate), other dental monomers can be used to prepare dental compositions. MPE was polymerized into a dental composition with light polymerized in the presence of 0, 8, or 16 wt % H₂O, which showed the MPE monomer can be polymerized in the presence of water. Adhesives were photopolymerized in the presence of 0, 8 and 16 wt % water to simulate the wet conditions of the mouth and were compared to control adhesives (HEMA/BisGMA, 45/55 w/w, at 0, 8 and 16 wt % water).

The ability of the dental composition having MPE to polymerize in the presence of water is important. Dental compositions formulated in the presence of water to simulate the behavior of these materials within the wet demineralized dentin matrix. When polymerized in the presence of water, dentin adhesives that include MPE within the polymer matrix show greater resistance to esterase degradation, suggesting improved performance in the wet, oral environment.

Additionally, MPE dental compositions were shown to have superior stability when in contact to components of human saliva. Human saliva contains a variety of enzymes which may participate in the degradation of the adhesive as well as the composite. The extent of hydrolysis for the methacrylate materials appeared to be largely dependent on chemical structures of the monomer. The superior stability of MPE containing dental compositions is important. The enhanced esterase resistance afforded by adhesives containing the synthesized urethane-linked trimethacrylate monomer is greater when the material is photopolymerized in the presence of water, suggesting better performance in the moist environment of the mouth.

The extent of polymerization influences the physical and mechanical properties of the polymer, and may also contribute to their susceptibility to enzymatic degradation. The degree of conversion (DC) of samples polymerized in the presence of 8 wt % and 16 wt % water was greater than those cured without water, which may be due to enhanced mobility of reactive species in lower viscosity solutions containing water. There was no significant difference in the DC of control and experimental adhesives, suggesting that the experimental adhesives reach DC comparable to that of the control, regardless of the presence or absence of water.

Dental compositions, based on the adhesive data, that are prepared with MPE are expected to have improved mechanical properties, or properties that are at least comparable to standard compositions. As such, the MPE monomer can be prepared to substantially any dental composition.

In one embodiment, the dental compositions formed with MPE can be capable of forming a hybrid layer, which can be from the application of acids or self-etching acidic primers to the dentin, followed by dental resin penetration into the decalcified zone. The complete penetration of dental monomers into the demineralized dentin can create strong bonding, and to envelop the collagen fibers.

In one embodiment, the high functionality and urethane functional group of MPE can contribute to increased esterase resistance of any dental resin containing this material (i.e., MPE), especially in the presence of water. The factors affecting the enzymatic degradation of methacrylate resins include the DC, crosslink density, monomer structure and morphology of polymer network. The improved esterase resistance of the experimental adhesive in this study could be explained in terms of a greater degree of crosslinking due to the higher functionality of the new monomer and/or minimizing the enzyme's access to the ester bond due to both the intra- and intermolecular hydrogen bonds (NH of urethane and C=O of ester) of the new monomer in the polymer matrix.

In one embodiment, the MPE monomer can be used as a co-monomer in dentin adhesives with increased esterase resistance. The new experimental adhesives showed a degree of double bond conversion comparable with the control. On exposure to porcine liver esterase, the net cumulative MAA release from the experimental adhesives containing new monomer was significantly less than the controls, indicating that the new adhesive has greater esterase resistance when formulated under wet conditions simulating the oral cavity than adhesives that model current commercial adhesives.

In one embodiment, the present invention includes a dentin adhesive or other composition having MPE that has the ability to tolerate higher concentrations of water without experiencing micro-level phase separation and resistance to breakdown when exposed to esterase. These beneficial properties are achieved without sacrificing degree of conversion, adhesive penetration or mechanical properties.

In one embodiment, the present invention includes a method for synthesizing and characterizing MPE. Methods of synthesis are shown in FIG. 1 and explained below.

In one embodiment, the new MPE monomer can be used in dental composite restorative materials, pit and fissure sealants, and adhesive resin cements for dentistry. As such, any other monomers that can be used in visible-light polymerization of dental compositions can be combined with the MPE monomer to make dental polymers.

Dental compositions in accordance with embodiments of the present invention can include pit and fissure sealants, permanent fillings, temporary fillings, cements, varnishes, composites, adhesives, and the like. Accordingly, these dental compositions can be configured for being cured after being placed into the mouth such as for filling and sealing root canals. For example, the dental compositions can be formulated for adhering veneers, inlays, onlays, crowns, pontics, and bridges in the mouth. Also, the dental compositions can be used in orthodontics for affixing an orthodontic bracket to a tooth.

Generally, a dental composition can include at least one polymerizable resin and at least one polymerizing initiator that are admixed together into a dental composition that is configured for placement on a person's tooth. The dental composition is formulated to blend with the person's tooth under natural conditions and/or white light.

In another embodiment, a kit or two-part composition having a combination of compositions can be provided. Such a combination of compositions can include at least one dental composition configured for placement onto a person's tooth, and at least one composition comprised of a polymerization initiator. The polymerization initiator composition can be used for being combined with the at least one dental composition prior to, during, or after being applied to the person's tooth in order to induce polymerization. The combination of compositions can be formulated to blend with the person's tooth under normal conditions and/or white light. the polymerization can be initiated as described herein.

A dental composition can include any composition that is formulated to be combined with another composition prior to being fixedly applied to a tooth. As such, the resultant combination of compositions, such as an admixture, can be properly formulated to adhere to a tooth, where the individual compositions may or may not have sufficient dental-compatibility or adherence.

Additionally, the dental composition can include solid prefabricated dental prostheses. Accordingly, a dental prosthesis such as a veneer, crown, inlay, onlay, pontic, or bridge can be prefabricated before being adhered to the patient's tooth. These dental prostheses can be comprised of a dental composite that has been cast into a solid form. A dental prosthesis can be affixed to a tooth with an adherent dental composition such as a dental composition having the novel monomer described herein.

The monomer or polymer prepared therefrom can also be admixed with a dispersing agent to facilitate the dispersement and retention of the monomer or polymer in the composition. Examples of dispersing agents include polymers and copolymers of styrene sulfonate salts, acrylic and styrene copolymers, sulfonated polyesters, oleoyl methyl taurine, sodium dodecyl sulfate, amine dispersants, methyl stearate, ethyl stearate, methyl hexanoate, methyl heptanoate, methyl octanoate, methyl laurate, methyl oleate, methyl adipate, methyl caprylate, methyl caproate, methyl anthranilate, methyl palmitate, methyl palmitoleate, methyl oxalate, methyl 2-nonanoate, methyl benzoate, 2-methylbenzophenone, methyl benzilate, methylbenzyl acetate, trimethyl borate, methyl caprate, methyl butyrate, methyl decanoate, methyl cyclohexanecarboxylate, methyl dimethoxyacetate, methyl diphenylacetate, methyl heptanoate, methyl linoleate and the like.

Additionally, the dental compositions can include a variety of materials such as polymerizable resins, polymerization initiators, fillers, coupling agents, plasticizers and the like. The polymerizable resin can include monomers, oligomers, and polymers having one or more ethylenically unsaturated groups, where ethylenically unsaturated groups can be polymerized by free radical polymerization. Such free radical polymerizable materials include monomers and/or mono-, di-, tri-, or poly-acrylates and methacrylates. For example, the polymerizable resins can include methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, diurethane dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol ("Bis-GMA"), bis[1-(2-acryloxy)]-p-ethoxyphenyldimethylmethane, bis[1-(3-acryloxy-2-hydroxy)]-p-propoxyphenyldimethylmethane, trishydroxyethyl-isocyanurate trimethacrylate, the bis-acrylates and bis-methacrylates of polyethylene glycols of molecular weight 200-500, copolymerizable mixtures of acrylated monomers, and copolymerizable acrylated oligomers, and the like. Alternatively, phosphoric acid derivatives and carboxylic acid derivatives of these ethylenically unsaturated monomers can be used. Also, vinyl compounds such as styrene, diallyl phthalate, divinyl succinate, divinyl adipate and divinylphthalate can be polymerized. Additionally, mixtures of two or more of these free radically polymerizable materials can be used if desired. However, it should be recognized that this is not an exhaustive listing of polymerizable resins, and other polymerizable resins can be used in accordance with the present invention.

The polymerizable resins can be included in the dental composition over a wide range of concentrations. The concentration can depend on the amount of filler, plasticizer, and polymerization initiator as well as other factors. For example, the dental composition can have a polymerizable resin such as an ethylenically unsaturated monomer at a preferred range of from about 10% to about 99% by weight, more preferred range of from about 15%-80% by weight, and most preferred range of from about 25% to about 50% by weight.

Typically, free radical polymerization requires an initiator to generate a free radical. Various types of initiators can produce a free radical upon being exposed to light, heat, or chemicals. The initiator compounds are provided into the dental compositions of the invention in an effective amount to initiate or enhance the rate of polymerization or curing.

Photo-initiators are a group of compounds that will generate a free radical when exposed to light having a specific wavelength. As such, different photo-initiators can be selected depending on the wavelength of light that will initiate the polymerization. Examples of photo-initiators can include benzophenone, benzoin, 9,10-phenanthrenequinone, diacetyl, furil, anisil, 4,4'-dichlorobenzil, 4,4'-dialkoxybenzil, phenylpropanedione, acylphosphine oxides, camphorquinone, derivatives thereof, and the like. Photopolymerization can be initiated, for example, by irradiation with light having a wavelength of from about 400 nm to about 500 nm.

Examples of a photoinitiator system can include a component selected from the group of acylphosphine oxides, bisacyl phospine oxides, camphorquinone, benzophenone, alkyl ethers of benzoin, diphenoxy benzophenone, benzildimethylketal, halogenated functional benzophenones, amino functional benzophenones, benzils, benzimidazozles, 2-hydroxy-2-methylphenol-1-propanone, fluorenone, fluorenone derivatives, 2,2-diethoxyacetophenone, benzoin, 9,10-phenanthrenequinone, anthraquinone derivatives, 2-benzyl-2-N,N-dimethylamino-1-(f-morpholinophenyl)butanone, zanthone, zanthone derivatives, halogenated acetophenone, halogenated acetophenone derivatives, thioxanthone, thioxanthone derivatives, sulfonyl chlorides of aromatic compounds, diacetyl, furil, anisil, 4,4'-dichlorobenzil, 4,4'-dialkoxybenzil, phenylpropanedione, acylphosphine oxides, 2-(dimethylamino)ethyl methacrylate, diphenyliodonium hexafluorophosphate, diphenyliodonium chloride, ethyl-4-(dimethylamino)benzoate, or combinations thereof.

A preferred photoinitiator system can include camphorquinone (CQ), 2-(dimethylamino)ethyl methacrylate (DMAEMA) and diphenyliodonium hexafluorophosphate (DPIHP). Another photoinitiator system is camphorquinone (CQ) and ethyl-4-(dimethylamino)benzoate (EDMAB). Any photoinitiator system can also include a iodonium salt.

Heat-initiators can be used in hot-curing systems, which is particularly suitable for producing inlays and onlays. Some heat-initiators can be activated with temperatures less than 150° C. Examples of heat-initiators can include t-butyl peroxide, dibenzoyl peroxide, dilauroyl peroxide, t-butyl peroctoate, t-butyl perbenzoate, and the like.

On the other hand, in certain applications a chemical-initiator, which typically is a system of at least two co-initiators that generate a free radical, can be used to induce polymerization. These chemical-initiator systems use a reactive pair, for example, benzoyl peroxide, lauryol peroxide, or dibenzoyl peroxide, in combination with a N,N-dimethyl-p-toluidine, N,N-dihydroxyethyl-p-toluidine, and other similar amines. Alternatively, a combined system including a photo-initiator, heat-initiator, and/or chemical-initiator can be used.

The concentration of the polymerization initiator depends on the concentration of the polymerizable resin, or more particularly on the concentration of the ethylenically unsaturated monomers. Additionally, the concentration of the polymerization initiator depends on the type of initiator. For example, the dental composition can include a polymerization initiator at a preferred range of from about 0.001% to about 5% by weight, more preferred range of from about 0.01% to about 2.5% by weight, and most preferred range of from about 0.1% to about 1% by weight. However, the concentration of initiator can be varied depending on the type of initiator and/or type of resin as well as the desired properties of the composition.

In another embodiment, a dental composition can include a filler to impart radiopaque, radiolucent, and/or non-radiopaque visual characteristics to the composition. The particles can include organic materials and inorganic materials. Examples of organic fillers include pulverized polycarbonates, polyepoxides, and the like. Additionally, polymeric particles or microbeads comprised of homopolymers or heteropolymers of the already described monomers can be used as organic fillers. Also, mixtures of fillers can be used.

Examples of inorganic fillers are naturally-occurring or synthetic materials such as quartz, nitrides (e.g., silicon nitride), colloid silica, feldspar, borosilicate, kaolin, ytterbium trifluoride, talc, and glasses. The glasses can be comprised of, for example, silicon (Si), cerium (Ce), antimony (Sb), tin (Sn), zirconium (Zr), strontium (Sr), barium (Ba), aluminum (Al), zinc (Zn), and the like. More particularly, the glasses can be oxides of these materials.

In one embodiment, the composition can include a filler at a preferred range of from about 0% to about 90% by weight, more preferred range of from about 0% to about 50% by weight, and most preferred range of from about 0% to about 25%. The filler can be comprised of particles having a preferred diameter range of from about 0.005 micrometers to about 50 micrometers, more preferred range of from about 0.5 micrometers to about 25 micrometers, or most preferred range of from about 1 micrometer to about 10 micrometers. For alternative embodiments it may be more preferable for the fillers having an average particle size of from about 0.005 micrometers to about 2 micrometers can be used. However, larger or smaller particles sizes can be used. Additionally, x-ray opaque fillers having particles sizes less than 5 micrometers such as ytterbium trifluoride and the like can impart beneficial characteristics to the tooth.

In order to enhance the bond between the filler and the dental composition, a coupling agent can optionally be used. Examples of coupling agents can include, without limitation, gamma-methacryloxypropyltrimethoxysilane, gamma-mercaptopropyltriethoxysilane, beta-(3,4-epoxycyclohexyl)-ethyltrimethoxysilane, gamma-glycidoxypropyltrimethoxysilane, and the like.

Various other additives can be included within the dental composition in accordance with the present invention. These additives can include stabilizers, UV absorbers, polymerization accelerators, polymerization inhibitors, dyes, pigments, and lubricants. Additionally, the dental compositions can include flavorants, anti-microbials, fragrance, viscosity modifiers, rheology modifiers, fluoride releasing materials, and plasticizers.

The monomer of the present invention can be derivatized. That is, the monomer, MPE, can include substituents and/or substitutions at various locations on the chemical scaffold. For example, the MPE monomer can be derivatized as follows: any of the ring groups can include substituents; any of the alkyl portions can include substituents; the oxygen molecules can be substituted with N, S, SO2 or the like; any hydrogen can be substituted with a halogen or short alkyl group; and other well known chemical modifications can also be employed.

III. Photoinitiator System

In dental resins, photopolymerization is catalyzed by mixed photoinitiator systems and occurs in the moist environment of the mouth. The model resin formulations used in this study are a mixture of a hydrophobic component (bisGMA) and a hydrophilic components (HEMA) and are based on conventional dentin adhesives. Commercial adhesives were not used, since differences in filler type and content, additives and processing conditions by the various manufacturers may influence results and adversely affect reproducibility. The model resins were formulated with water to simulate wet bonding conditions in the mouth and to allow for possible phase separation of the adhesive during photopolymerization.

The selection of an appropriate photoinitiator system can be important for efficient polymerization of dental resins with satisfactory mechanical and physical properties, especially when polymerization occurs in the mouth. Accordingly, an iodonium salt can be used in a photoinitiator system with improved characteristics for the dental composition that is obtained. The iodonium salt can be part of a two-component, three-component, or four component photoinitiator systems.

The chemistry of the photoinitiators used in dental resins is critical to their efficient polymerization and to satisfactory mechanical and physical properties of the polymer. Most photoinitiators formulated for commercial dental resins consist of two-components: (i) the photoinitiator (typically a camphorquinone, CQ) which can absorb light directly and (ii) a co-initiator (typically an amine) that does not absorb light but interacts with the activated photoinitiator to generate a reactive free radical and initiates polymerization. Camphorquinone (CQ) is a typical visible light-activated free radical photoinitiator with an absorbance range between 400 and 500 nm. CQ requires a tertiary amine reducing agent, usually ethyl-4-(dimethylamino)benzoate (EDMAB) and/or 2-(dimethylamino)ethyl methacrylate (DMAEMA), for efficient polymerization to occur.

The experimental data provided herein show that four different photoinitiator systems were included in a model bisGMA/HEMA resin and used to prepare samples at different water contents; the dynamic mechanical properties and the final degree of conversion of the samples were then characterized. The data shows that adding iodonium salt to the two-component photoinitiator systems increased the final degree of conversion, glass transition temperature, rubbery modulus, and crosslink density. The photoinitiator system containing ethyl-4-(dimethylamino)benzoate as a co-initiator and the iodonium salt exhibited the highest rubbery modulus. The enhanced properties in the presence of the iodonium salt can be attributed to the production of an active phenyl radical with regeneration of the original camphorquinone, which may increase the compatibility between monomers and initiators, especially in the presence of water. The results show that a photoinitiator system containing an iodonium salt can increase both mechanical properties and final conversion of model resin polymerized in the presence of water.

Examples of iodonium salts that can be included in a photoinitiator system can include diphenyliodonium hexafluorophosphate, diphenyliodonium chloride, and the like.

Additionally, the present invention can include a photoinitiator system that uses a halonium ion and/or halonium salt in combination with or place of the iodonium salt as described herein. The halonium ion is any onium compound (ion) containing a bridged halogen atom carrying a positive charge. This cation has the general structure R—$X^+$—R where X is any halogen and R any organic residue and this structure can be cyclic or an open chain molecular structure, examples of which are aromatic, cycloalkyls, and aliphatics that are branched or unbranched, substituted or unsubstituted. For example, R can be any R1, R2, R3, R4 or the like as described herein. A halonium ion also seems to refer generically to the simpler onium compounds (ions) based on halogens: fluoronium, $H_2F^+$; chloronium, $H_2Cl^+$; bromonium, $H_2Br^+$; iodonium, $H_2I^+$. Any halonium ion, such as the iodonium ion, with one or more R groups being a hydrogen or organic residue, that is a salt, can be used in the photoinitiator system in combination or in place of any iodonium salt described herein. However, the ionic halonium ions can be used instead of salts.

In one embodiment, the photoinitiator system is a three-component system, in which an iodonium salt is added to a two-component system. The two component system can be any known or standard two-component initiator system. It has been shown that the three-component photoinitiator system containing an iodonium salt (diphenyliodonium hexafluorophosphate (DPIHP)) increases both mechanical properties and final degree of conversion of a bisGMA/HEMA resin.

The results presented herein suggest that DMAEMA is a less efficient photoreducer than EDMAB, leading to lower DC and dynamic mechanical properties. This behavior may be attributed to the fact that DMAEMA is more prone to combine with oxygen than aromatic amines. In addition, since DMAEMA carries a methacrylate group with a double bond, DMAEMA-dimer or oligomers may be formed in the presence of radicals. The addition of DPIHP to the two-component photoinitiator systems increased the final degree of conversion, Tg, storage modulus, and crosslink density, especially in the presence of water. The enhanced properties observed in the presence of the iodonium salt, DPIHP may be due in part to its ability to generate an active phenyl radical. As an electron acceptor, the iodonium salt abstracts an electron from the inactive CQ neutral radical, regenerating the original CQ and producing a diphenyliodonium radical. The diphenyliodonium radical rapidly fragments into a molecule of phenyl iodide and a phenyl radical that is very active in initiating the polymerization. In addition, since DPIHP is ionic in nature as a salt, it may increase the compatibility between amphiphilic monomers (i.e., having both hydrophilic and hydrophobic characteristics) and initiators, especially in the presence of water.

EXPERIMENTAL

2-Hydroxyethylmethacrylate (HEMA, Acros Organics, NJ) and 2,2-bis[4-(2-hydroxy-3-methacryloxypropoxy)phenyl]-propane (BisGMA, Polysciences, Warrington, Pa.) were used as received without further purification as monomers in dentin adhesives. 1,1,1-tri-[4-(methacryloxyethylaminocarbonyloxy)-phenyl]ethane (MPE) was used as a co-monomer and synthesized in-house (FIG. 1). 1,1,1-tris(4-hydroxyphenyl)ethane, dibutyltin dilaurate (DBTL), and 2-isocyantoethyl methacrylate (IEM) were obtained from Aldrich, Milwaukee, Wis., USA and used for MPE synthesis. Camphorquinone (CQ) and ethyl-4-(dimethylamino)benzoate (EDMAB) were obtained from Aldrich (Milwaukee, Wis., USA) and used as photoinitiators without further purification. Porcine liver esterase (PLE, EC 3.1.1.1) was obtained from Sigma Chemical Co., St. Louis, USA. All other chemicals were reagent grade and used without further purification.

1.
A new monomer, 1,1,1-tri-[4-(methacryloxyethylaminocarbonyloxy)-phenyl]ethane (MPE), was synthesized by the reaction of 1,1,1-tris(4-hydroxyphenyl)ethane and 2-isocyantoethyl methacrylate, as shown in FIG. 1.

The new monomer, MPE, was synthesized following the procedures described by Xie et al., with slight modification. Briefly, to a three-neck flask containing 1,1,1-tris(4-hydroxyphenyl)ethane (THPE, 8.89 g, 0.029 mol), dibutyltin dilaurate (DBTL, 0.03 g), and dry tetrahydrofuran (THF, 50 mL) under $N_2$ atmosphere, 2-isocyantoethyl methacrylate (IEM, 13.73 g, 0.089 mol) was added dropwise with stirring at 0° C. Following complete addition of IEM, the reaction was allowed to continue at room temperature for another 5 hrs. The reaction was monitored by thin layer chromatography (mobile phase: $CHCl_3$:MeOH=9:1). After the reaction was completed, the product-containing solution was purified by washing with distilled water and ethyl acetate until the solution was clear. After drying over anhydrous $MgSO_4$, 0.05 wt % of 2,6-di-tert-butyl-4-methylphenol (BHT) was added and the solvent removed with a rotary evaporator at 35-40° C. The yield MPE, which is a white foamy compound, was in the range of 87-90%.

The MPE structure was identified by FTIR (FIG. 2) and $^1$H-NMR spectroscopy (FIG. 3A) and 13C-NMR spectroscopy.

Figure 2:
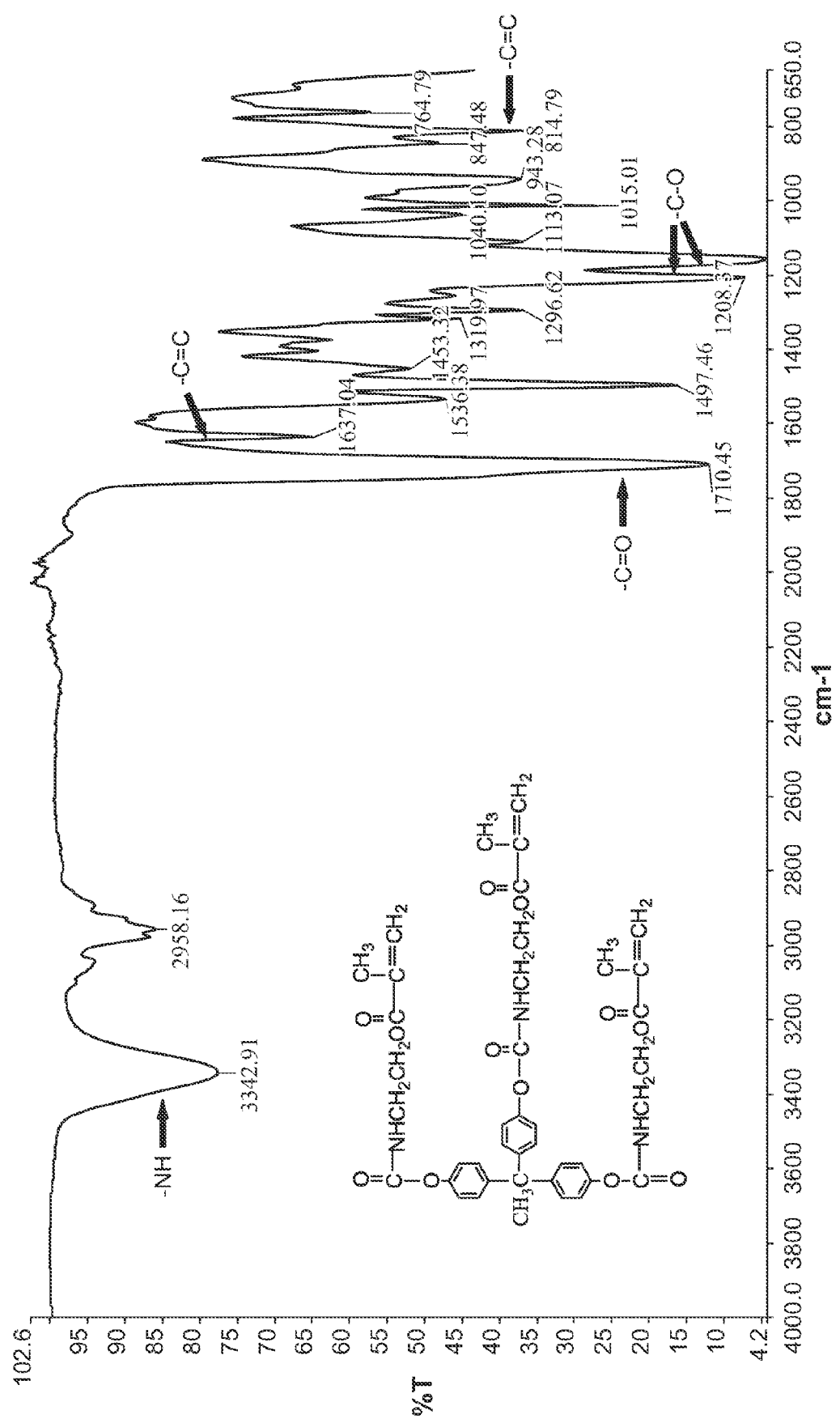
FIG. 2 is a FTIR spectrum of MPE.

FTIR (neat): 3270 cm$^{-1}$ (—NH), 1710 cm$^{-1}$ (C=O), 1637.9 cm$^{-1}$ (C=C, stretching), 1158.4 cm$^{-}$(C—O, stretching) (FIG. 2). The characteristic FTIR peaks for MPE are: 3342.9 cm$^{-1}$ (NH stretching on CONH), 1710.5 cm$^{-1}$ (C=O stretching on OCONH and OCO, where both carbonyl peaks overlap), 1637.0 cm$^{-1}$ (C=C bending on methacrylate group), 1536.4 cm$^{-1}$ (amide II, CONH), 1208.4 cm$^{-1}$ (C—O stretching), 815 cm$^{-1}$ (C=C twisting). Disappearance of the —NCO band at 2250 cm$^{-1}$ and appearance of the C=C stretching band at 1637.0 cm$^{-1}$ confirmed the formation of the new methacrylate monomer.

Figure 3A:
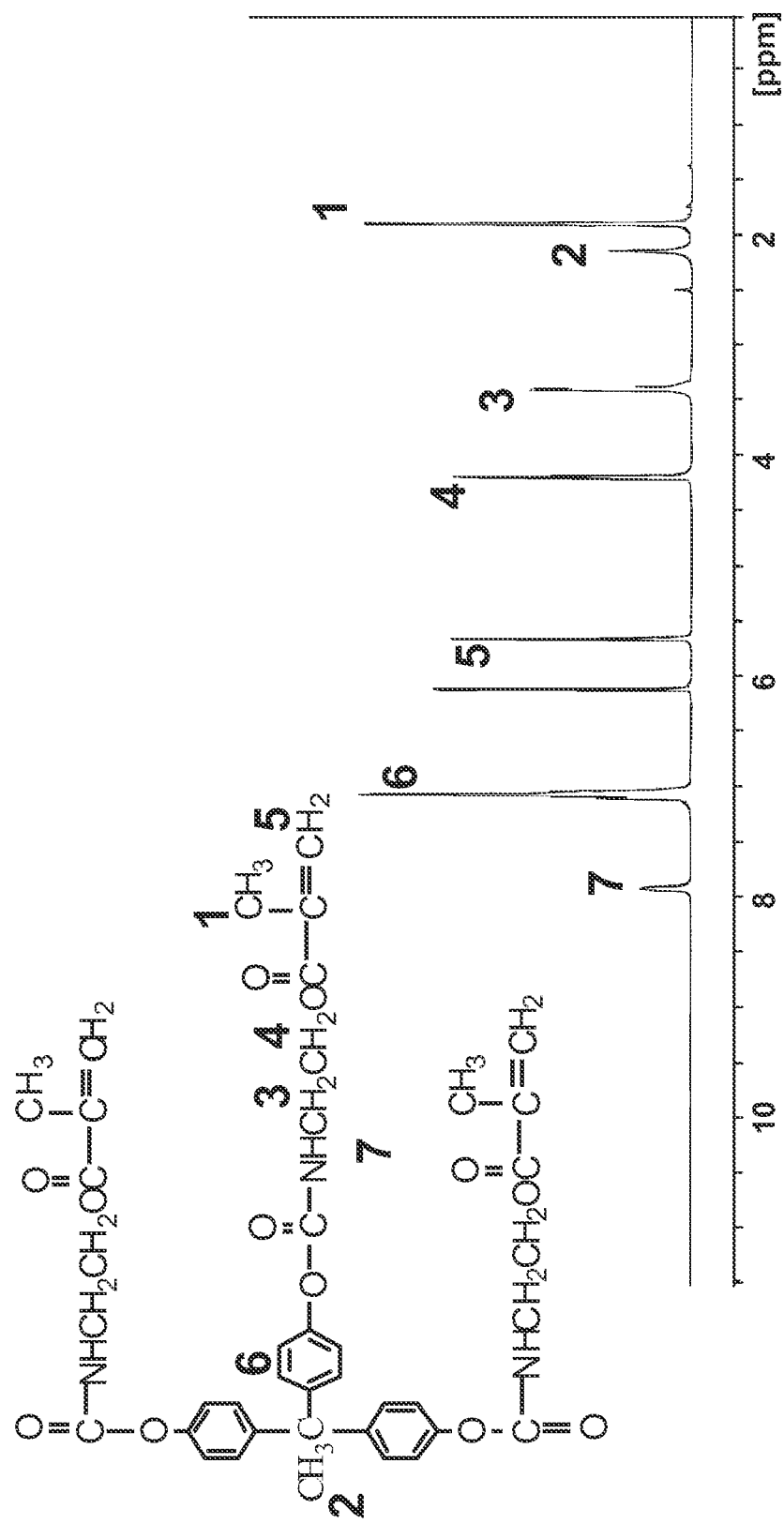
FIGS. 3A-3B are a $^1$H (FIG. 3A) and $^{13}$C (FIG. 3B) NMR spectra in DMSO of MPE.
Figure 3B:
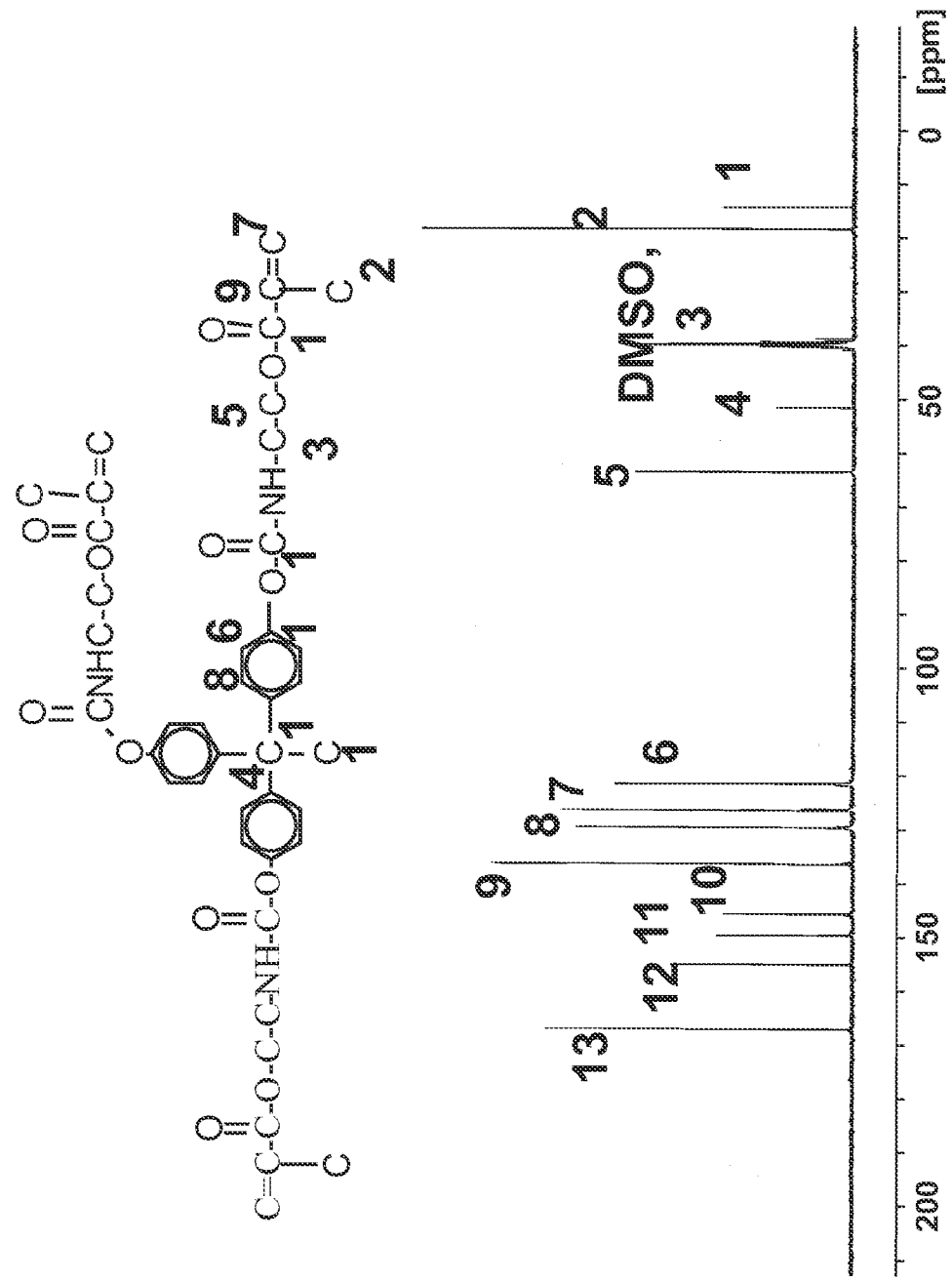

Spectral data of MPE are as follows: $^1$H-NMR (CDCl$_3$): δ7.1-6.9 (phenyl), 6.2 and 5.6 ppm (CH$_2$=C(CH$_3$)COO—), 5.4 (—NH), 4.25 (—NHCH$_2$CH$_2$O—), 3.5 —NHCH$_2$C H$_2$O—), 2.1 (CH$_3$C—), 1.9 ((CH$_2$=C(CH$_3$)COO—) (FIG. 3A). In the $^1$H-NMR spectrum (FIG. 2A), the chemical shifts of MPE were (ppm): a, 7.9 ($^1$H, —OCONH—); b, 7.1 (4H, C$_6$H$_4$—); c, 6.20 and 5.60 (2H, —CH$_2$=C(CH$_3$)COO—); d, 4.28 (2H, —NHCH$_2$CH$_2$O—); e, 3.4 (2H, —NHC H$_2$CH$_2$O—); f, 2.10 (3H, CH$_3$C(C$_6$H$_4$)$_3$—); g, 1.9 (3H, =CH$_2$=C(CH$_3$)COO—). In the $^{13}$C-NMR spectrum (FIG. 2B), the chemical shifts of MPE were (ppm): m, 166.9 (—CH$_2$=C(CH$_3$)COO—); l, 155.0 (—OCONH—); k, 149.0 (—C$_6$H$_4$—); j, 146.3 (—C$_6$H$_4$—); i, 136.0 (—CH$_2$=C(CH$_3$)COO—); h, 129.9 (=C$_6$H$_4$—); g, 126.3, (—CH$_2$=C(CH$_3$)COO—); f, 121.2 (=C$_6$H$_4$—); e, 63.6 (—N—C—C—O—); d, 51.3 (—CH$_3$C(C$_6$H$_4$)$_3$—); c, 40.0 (—N—C—C—O—); b, 18.0 (CH$_2$=C(CH$_3$)COO—); a, (CH$_3$C(C$_6$H$_4$)$_3$—). The methacrylate and aromatic groups are supported by the presence of two singlets at 6.1 and 5.6 ppm for the double bond, by multiplets at 7.1 ppm for the benzene ring on the $^1$H-NMR spectrum, by the peaks at 136.2 and 125.5 ppm for the double bond, and by peaks at 121.0, 129.9, 146.0, and 149.6 ppm for the benzene ring in the $^{13}$C-NMR spectrum.

2.
Adhesives, containing hydroxyethyl methacrylate and BisGMA (bisphenol A dimethacrylate) in addition to MPE, were formulated with $H_2O$ at 0 (2A0T), 8 (2A8T) and 16 wt % water (2A16T) and compared with control adhesives [HEMA/BisGMA, 45/55 w/w, at 0 (2A0), 8 (2A8) and 16 wt % water (2A16)]. Camphoroquinone (CQ) and Ethyl 4-(dimethylamino)benzoate were used as photoinitiators. The liquid resin was injected into aluminum pan and sealed with a cover glass and cured with visible light curing at 550 mW/cm$^2$ light intensity for 40 sec.

Figure 4:
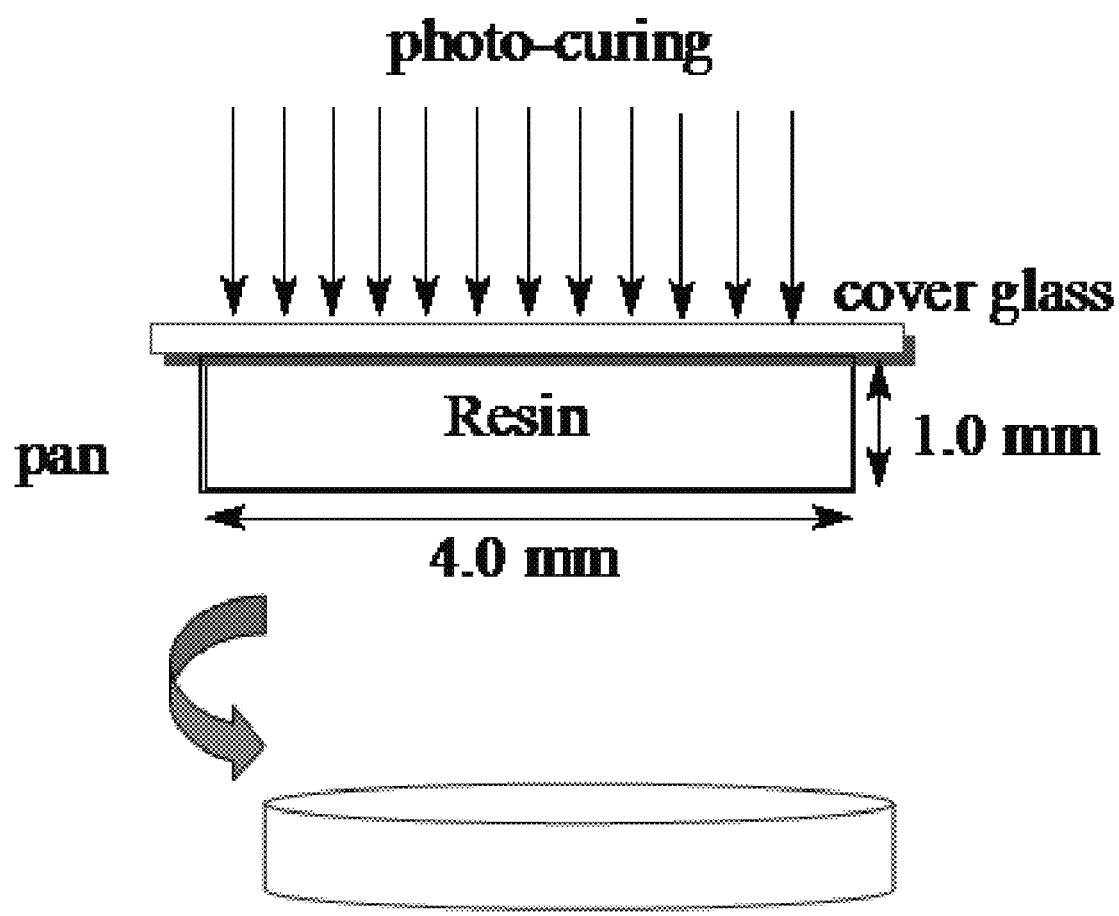
FIG. 4 is a schematic of preparing dental composition outside of a mouth. The process can also be conducted in a mouth of a subject.

FIG. 4 shows a schematic representation of a process for preparing an dental adhesive. Briefly, the liquid resin was injected into aluminum pan and sealed with a cover glass and cured with visible light curing at 550 mW/cm$^2$ light intensity for 40 sec. Control adhesive formulations consisted of HEMA and BisGMA with a mass ratio of 45/55, which is similar to commercial dentin adhesives such as Single Bond (3M ESPE, St. Paul, Minn.). Control adhesives were formulated with 0 wt % (AO), 8 wt % (A8) and 16 wt % (A16) water to simulate the moist environment of the mouth. The experimental adhesive formulations, HEMA/BisGMA/MPE=45/30/25 w/w ratio, in which MPE was used as a co-monomer, were also formulated with 0 wt % (A0T), 8 wt % (A8T) and 16 wt % (A16T) water. CQ (0.5 wt %) and EDMAB (0.5 wt %) were used as photoinitiator and co-initiator, respectively, with respect to the total amount of monomer. The resin mixtures were shaken on an orbital shaker for 2 days to dissolve the initiators completely and form a homogeneous solution. The resin solution was then placed into an aluminum mold (4 mm diameter and 1 mm thickness) and covered with a plastic film to form disc specimens for biodegradation studies. Rectangular beam specimens (1×1×11 mm$^3$) cured in a glass-tubing mold (Fiber Optic Center Inc., Vitrocom hollow square capilliaries, 1.00 mm square I.D., 0.200 mm wall thickness, borosilicate glass) were prepared for the determination of mechanical properties. The adhesives placed in the mold were light-cured for 40 s at room temperature at a distance of 1 mm using a commercial visible-light-curing unit (Spectrum® 800, Dentsply, Milford, Del., USA) at an intensity of 550 mW $cm^{-2}$, according to techniques published previously. The cured specimens were removed from the mold after storage for 24 hrs in a dark room at room temperature.

3.

The degree of conversion (DC) was determined from the surface of randomly selected discs using a Perkin-Elmer Spectrum One Fourier transform infrared spectrophotometer (FTIR) with a resolution of 4 $cm^{-1}$. For enzymatic biodegradation, from each group, five adhesive discs with a surface area of about 2 $mm^2$ (2 $mm^2$/mL) were placed in sterile bottles and pre-washed in 0.01 M phosphate buffered saline (PBS), pH 7.4, for 3 days to remove most of the unpolymerized monomers. Following the pre-wash, adhesive discs were incubated in 1 mL 0.2 M phosphate buffer solution containing porcine liver esterase (PLE, EC 3.1.1.1., Sigma E3019), 30U/ml, at 37° C. for 8 days with shaking; concurrent analysis without enzyme consisted of incubations of test specimens in 0.2M phosphate buffer (PB). Daily changes with PLE enzyme were necessary to maintain its optimum activity. PLE was selected for its non-specific effect on ester bonds and its optimum activity was routinely checked at zero and 24 hours using ethyl butyrate. Daily changes of fresh enzyme allowed daily collection of the aqueous phase supernatants, which upon collection was immediately centrifuged to remove the enzyme (15 min at 10,000 g). The supernatants were collected daily and analyzed for methacrylic acid (MAA) by HPLC with UV-detection at 208 nm up to 8 days.

The degree of conversion (DC) of the methacrylate double bond of the adhesives was determined using a Perkin-Elmer Spectrum One Fourier transform infrared spectrophotometer (FTIR) with a resolution of 4 $cm^{-1}$. One drop of adhesive solution was placed on the diamond crystal top-plate of an attenuated total reflectance (ATR) accessory (Perkin-Elmer, Waltham, Mass., USA), covered with a mylar film to prevent oxygen inhibition of polymerization. A 40 sec-exposure to the commercial visible-light-polymerization unit (described above) was initiated after 50 spectra had been recorded. Real-time IR spectra were continuously recorded for 600 sec after light activation began. The ATR crystal was zinc selenide (ZnSe) with a transmission range between 650 and 4000 $cm^{-1}$. A time-based spectrum collector (Spectrum TimeBase, Perkin-Elmer) was used for continuous and automatic collection of spectra during polymerization. Three replicates were obtained for each adhesive formulation. The change of the band ratio profile (1637 $cm^{-1}$(C=C)/1608 $cm^{-1}$(phenyl)) was monitored and DC was calculated using the following equation based on the decrease in the absorption intensity band ratios before and after light curing. The average of the last 50 of time-based spectra is reported as the DC value.

$$DC = \left(1 - \frac{\frac{Absorbance_{1637\,cm^{-1}}^{sample}}{Absorbance_{1608\,cm^{-1}}^{sample}}}{\frac{Absorbance_{1637\,cm^{-1}}^{monomer}}{Absorbance_{1608\,cm^{-1}}^{monomer}}}\right) \times 100\%$$

Figure 5:
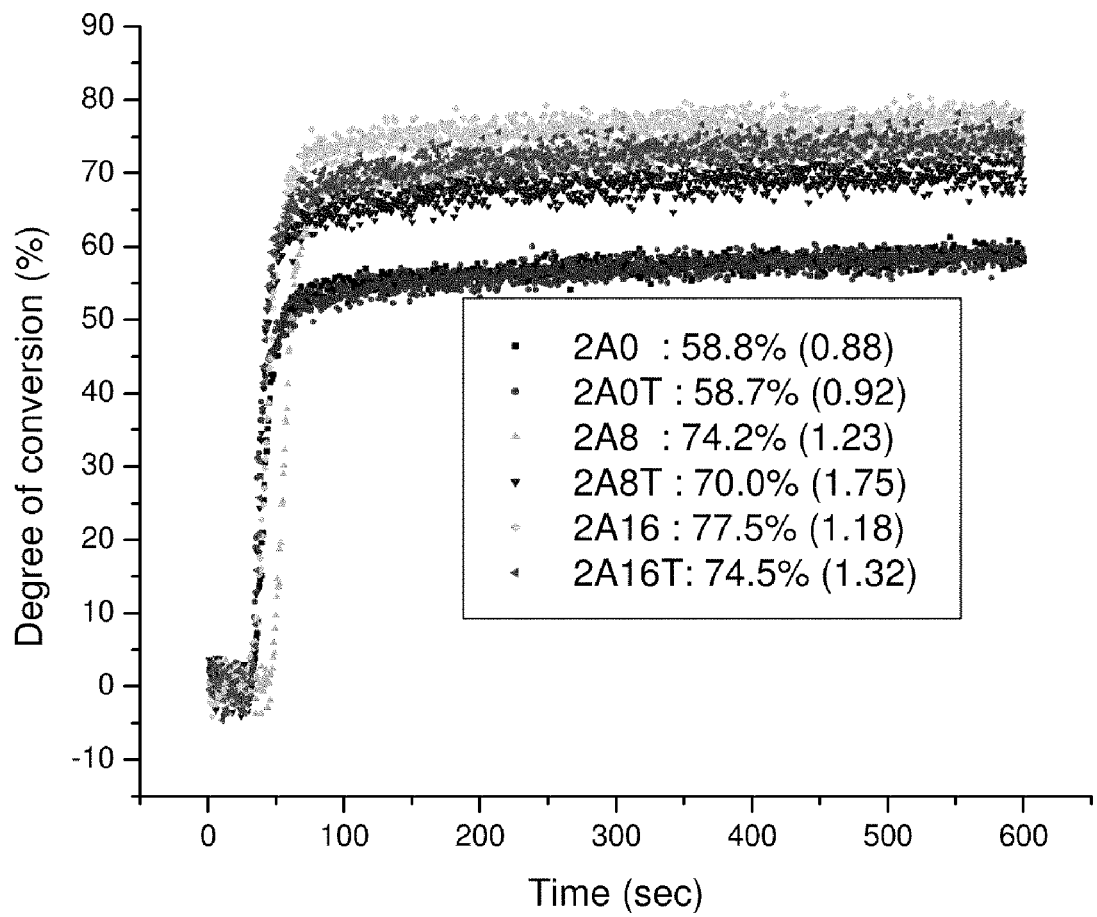
FIG. 5 is a graph of the real-time conversion of control (A0, A8, A16) and experimental adhesives (2A0T, 2A8T, 2A16T). The adhesives were light-cured for 40 sec at room temperature using a commercial visible-light-curing unit (Spectrum® 800, Dentsply, Milford, Del., USA) at an intensity of 550 mW cm$^{-2}$.

FIG. 5 is a graph that shows the degree of conversion of dentin adhesives cured in the presence or absence of water. The polymerization conversion of adhesives was about 59% when cured in the absence of water. When cured in the presence of water such as 8% and 16%, the polymerization conversion was in the range of 70-77%, which is significantly higher than those cured without water. The new adhesive showed a degree of double bond conversion and mechanical properties comparable with control, with good penetration into the dentin surface and a uniform adhesive/dentin interface. Conversion of all the adhesives tested approached a plateau at 80 seconds after light initiation. The adhesives were light-cured for 40 sec at room temperature using a commercial visible-light-curing unit (Spectrum® 800, Dentsply, Milford, Del., USA) at an intensity of 550 mW $cm^{-2}$. There were no marked differences in the DC values for in situ photopolymerization of control and experimental adhesives cured in the absence of water. The polymerization conversion was ~60 % when cured in the absence of water.

As shown in Table 5, The DC for control and experimental adhesives was nearly identical. The half-width of the peak for HBM-0 was lager than HB-0, suggesting higher heterogeneous polymer than HB, however it is not significantly different for adhesives cured in the presence of water. The HBM exhibits a smaller tan δ peak compared to the HB, suggesting higher elastic polymer than HB.

4.

The adhesives to be tested for stability against esterases were prepared to contain HEMA and BisGMA in addition to MPE. The adhesives were photopolymerized in the presence of 0, 8 and 16 wt % water to simulate the wet conditions of the mouth and were compared to control adhesives (HEMA/BisGMA, 45/55 w/w, at 0, 8 and 16 wt % water). Five adhesive discs with a surface area of ~2.0 $cm^2$/ml were placed in sterile vials and pre-washed in sterile 0.05M phosphate buffer saline (PBS) with pH 7.4 for three days to remove unreacted monomer. Following the pre-wash, adhesive discs were incubated in 1 mL of 0.2 M phosphate buffer solution containing 30 U/mL porcine liver esterase (PLE, EC 3.1.1.1., Sigma E3019) at 37° C. for 8 days with shaking; concurrent analysis without enzyme consisted of incubations of test specimens in 0.2M phosphate buffer (PB). Daily changes with PLE enzyme were necessary to maintain its optimum activity. PLE was selected for its non-specific effect on ester bonds and its activity was routinely checked at zero and 24 hours using ethyl butyrate. One unit of fresh PLE hydrolyzed 1.0 μmole of ethyl butyrate to butyric acid and ethanol per minute at pH 8.0/25° C.; after 24 hours, the activity was 96-98% of this value. Solution samples obtained each day were immediately centrifuged (15 min×13,400 rpm) to remove the enzyme. The supernatants were then stored at −20° C. until analysis by HPLC. The methacrylic acid content (MAA) was determined by reverse phase HPLC using a 600E system controller, a 717 plus autosampler and a 484 tunable wavelength UV (208 nm) detector from Waters (Milford, Mass.). Samples were thawed and centrifuged again prior to injection into the HPLC system for analysis. An enzyme-free solution at pH 7 and 37° C. served as a negative control and as a measure of the non-enzymatic hydrolysis of each material. A Phenomenex Luna 5 μm $C_{18}$ 4.6×250 mm (Phenomenex, Torrance, Calif.) column and security guard cartridge were used to isolate the products. The mobile phase was $CH_3CN$: 10 mM potassium phosphate buffer (60:40, v/v) at a flow rate of 1.0 mL/min. MAA concentrations were determined by comparing peak areas with a calibration curve prepared using MAA standards of 50, 100, 250, 500, and 1000 μM concentration. Relative retention times of HPLC peak of the standard solution were found to be 1.9 min for MAA.

Following the pre-wash for three days, adhesive discs were incubated in buffer solution with/without porcine liver esterase (PLE) at 37° C. Supernatants were collected daily and analyzed for methacrylic acid (MAA) by HPLC. Exposure of photopolymerized discs to PLE showed that the net cumulative MAA release in adhesives formulated with the new monomer and 8% water (2A8T: 306 μg/mL) was dramatically decreased in comparison to the control (2A8: 1352 μg/mL). This suggests that the new monomer improves esterase resistance.

Figure 6:
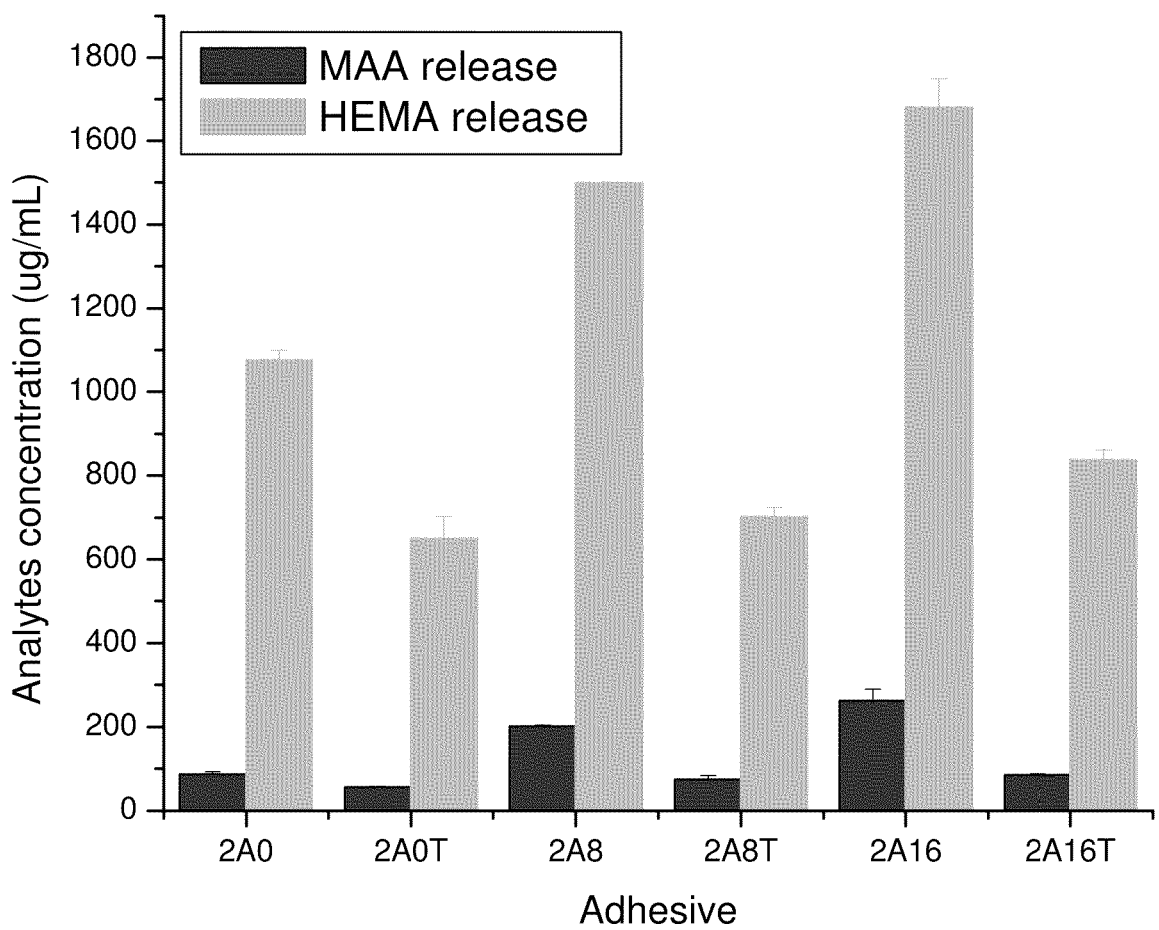
FIG. 6 is a graph of the MAA and HEMA release from various dental compositions.

Calibration curves were prepared to identify the HPLC chromatogram for HEMA and MAA. MAA and HEMA concentrations were determined by comparing peak areas with a calibration curve prepared using MAA and HEMA standards of 50, 100, 250, 500, and 1000 μM concentration. Relative retention times of HPLC peak of the standard solution were found to be 1.9 min for MAA and 3.1 min for HEMA. FIG. 6 shows the release of MAA and HEMA in the pre-wash in PBS for 3 days.

Figure 7A:
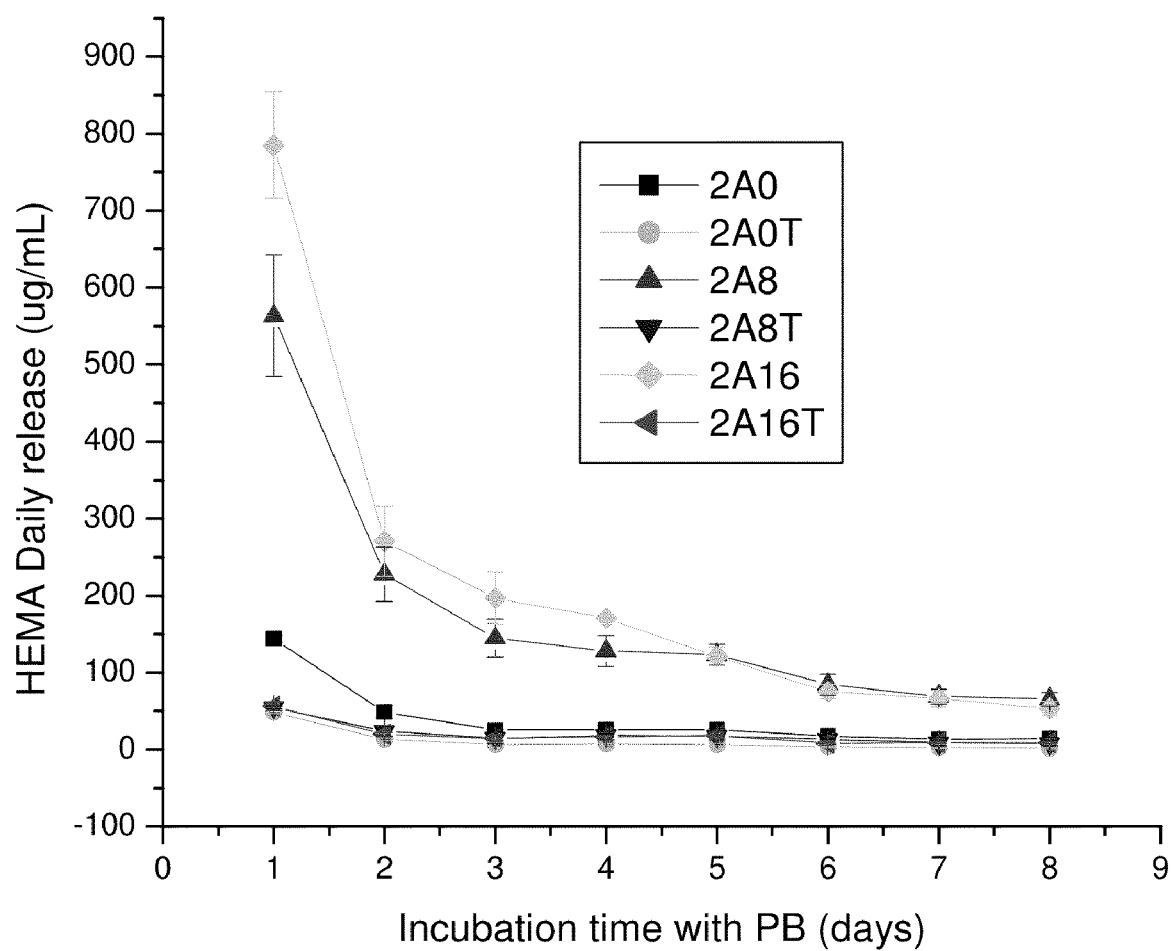
FIGS. 7A-7B include graphs of the MAA (FIG. 7B) and HEMA (FIG. 7A) daily release from various dental compositions.
Figure 7B:
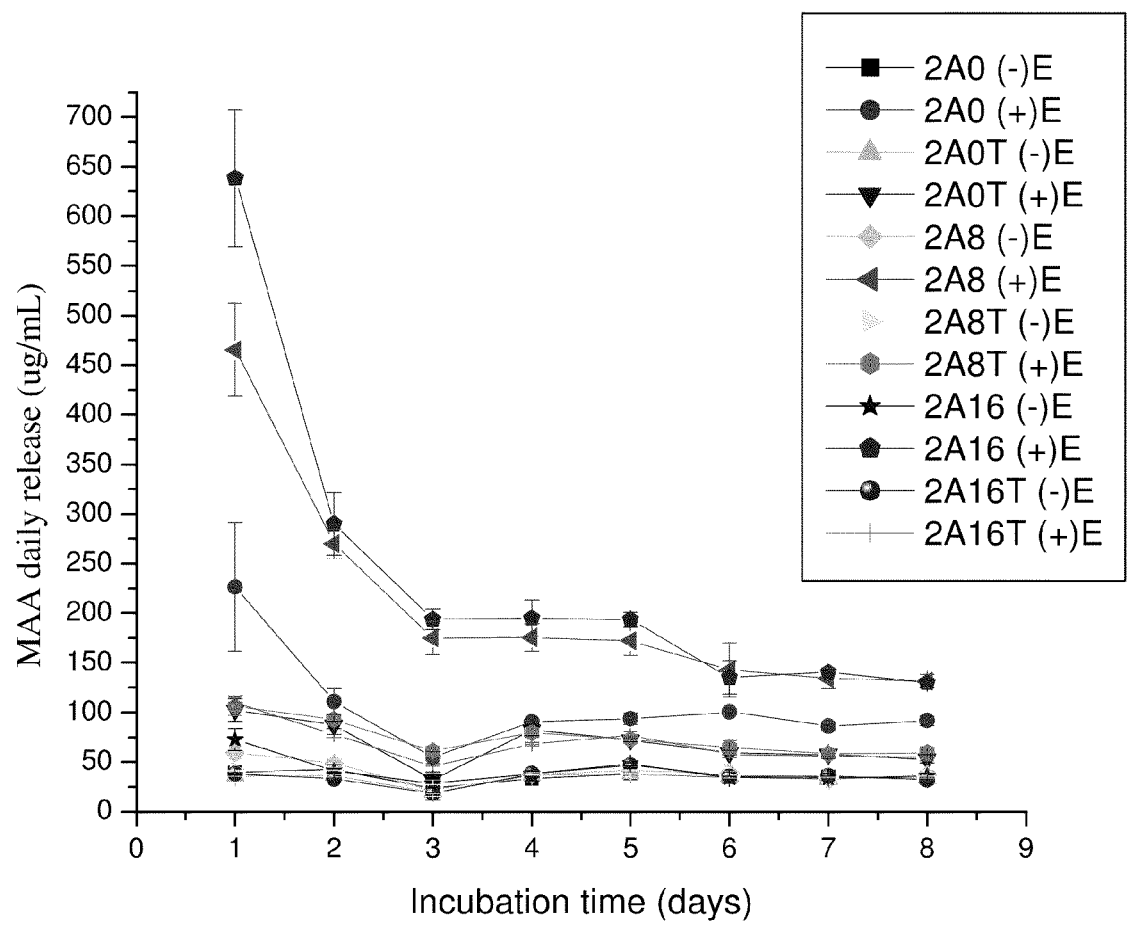

FIGS. 7A and 7B show the daily HEMA (FIG. 7A) and MAA (FIG. 7B) release in phosphate buffer solution. The concentration of unreacted MAA and HEMA release in the pre-wash increased with increasing water content, and the release of HEMA (648-1679 μg/mL) was significantly increased for all the adhesives tested compared to MAA release (56-263 μg/mL). Control adhesives (2A8 and 2A16) formulated with water showed significantly higher daily content of residual HEMA in PB than 2A0 as well as all the experimental adhesives. HEMA release for 2A8 and 2A16 was very high in the first day and decreased gradually up to 5 day and then leveled off at 6 day. In comparison, the experimental adhesives (2A0T, 2A8T and 2A16T) showed low HEMA release; HEMA release in the experimental adhesive formulated in the presence of water was comparable to the control adhesive formulated without water. HEMA release in the experimental adhesive reached a plateau after 2 days. MAA release from all the formulations in the presence of enzyme (+E) was significantly increased compared to MAA levels in phosphate buffer (−E). In systems with esterase, the daily levels of MAA release for A8 and A16 were significantly increased compared to other adhesives and leveled off by the $6^{th}$ day.

Figure 8:
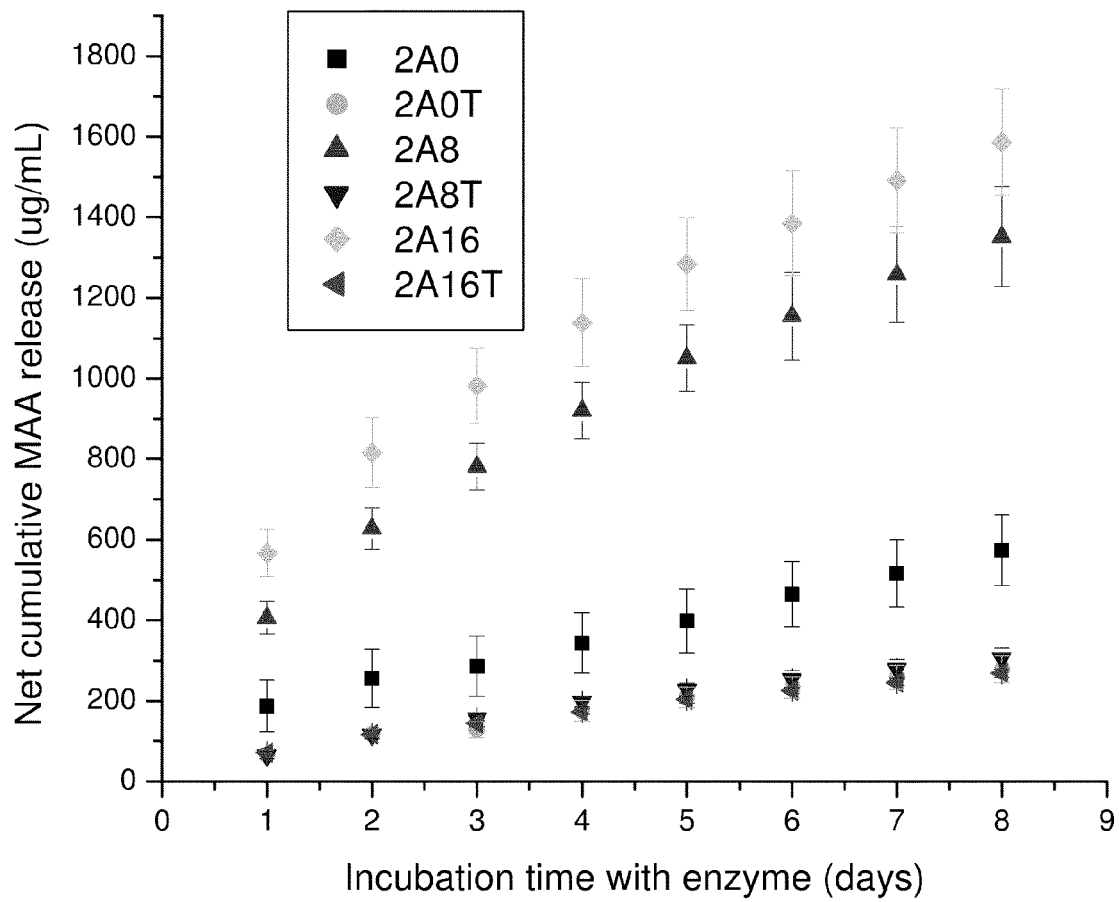
FIG. 8 is a graph showing the net cumulative MAA release from various dental adhesives as a function of incubation time on exposure to esterase for control formulations and experimental formulations. Net cumulative MAA release was obtained by subtracting the MAA release measured without PLE in phosphate buffer [MAA$_{in\ PLE}$-MAA$_{in\ PB}$]. 2A0, 2A8, 2A16 are control formulations polymerized in the presence of 0, 8 or 16 wt % water; 2A0T, 2A8T, 2A16T are experimental formulations containing MPE polymerized in the presence of 0, 8 or 16 wt % water.

Net cumulative release of MAA in the presence of PLE is shown in FIG. 8 and was obtained by subtracting the MAA release measured in buffer [$MAA_{in\ PLE}$-$MAA_{in\ PB}$].

FIG. 8 shows the net cumulative MAA release from control and experimental adhesives in enzyme. The total net cumulative release of MAA for control adhesives exposed to esterase and cured in the presence of water (2A8=1352 μg/mL; 2A16=1586 μg/mL) was significantly greater than 2A0 (574 μg/mL). The experimental adhesives showed similar MAA release upon exposure to esterase, regardless of the presence of water in the resin mixture. MAA release was approximately 300 μg/mL for 2A0T, 2A8T and 2A16T.

The net cumulative MAA release from the experimental adhesives containing MPE was significantly less than the controls, indicating that the new adhesives has greater esterase resistance than conventional adhesives. In addition, even when formulated in the presence of 16 wt % water, esterase resistance of the experimental adhesive containing MPE was superior to the control adhesive formulated under dry conditions.

The net cumulative release of MAA for control adhesives cured in the presence of water (A8, 1352 μg/mL; A16, 1586 μg/mL) was significantly greater than for control adhesives cured in the absence of water (A0, 574 μg/mL). The experimental adhesives showed similar MAA release regardless of the presence of water in the resin mixture (approximately 300 μg/mL for A0T, A8T and A16T).

The control adhesives cured in the presence of water showed greater net cumulative MAA release than the control cured in the absence of water. This result may be linked to the BisGMA structure and adhesive phase separation that occurred when the materials were photopolymerized in the presence of water. BisGMA has a relatively unhindered ester bond as compared to the new monomer and has two pendant hydroxyl groups, which are responsible for the high water sorption, and may increase its susceptibility to hydrolytic degradation. Due to adhesive phase separation, poorly polymerized hydrophilic polymer domains degrade rapidly in the aqueous oral environment.

5.

Rectangular beam specimens ($1 \times 1 \times 11$ mm$^3$) were used to determine mechanical properties. Ten specimens were prepared for each of the control (A0, A8, and A16) and experimental adhesives (A0T, A8T, and A16T). Tensile properties were determined for all samples after either 24 h storage-in-air (n=5 per sample type) at room temperature or after storage for 24 h in distilled deionized water (n=5 per sample type). Following storage, specimens were attached tightly to the upper and lower grips using cyanoacrylate cement (Zapit, Dental Ventures of America, Corona, Calif., USA) and were loaded at a cross-head speed of 0.5 mm/min using an SSTM-5000 mechanical tester (United Calibration Corporation, California, USA) with a 150 lb load cell. The toughness (T, m MN m$^{-3}$) of the specimen was calculated as the area under the stress-strain curve. Percent elongation (EL, %) was calculated as the value at the point of failure divided by the original gauge length of the specimen. The ultimate tensile strength (UTS, MPa) is the maximum resistance to fracture, and was measured from the maximum force at the point of failure divided by the specimen cross-sectional area. The elastic modulus (E, GPa) was obtained as the slope of the linear portion of the stress-strain curve between 5% and 15% strain for all specimens. Four to eight specimens in each group were tested.

Figure 9A:
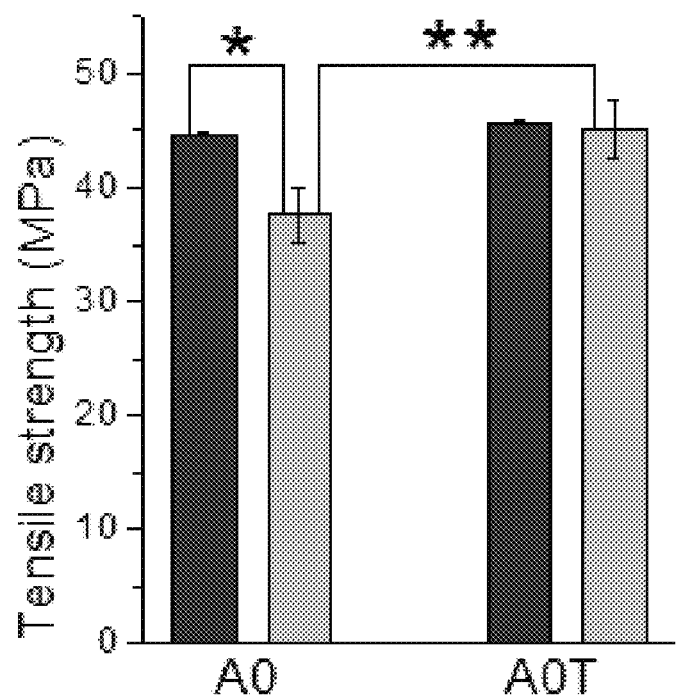
FIGS. 9A-9C are graphs showing the ultimate tensile strength of control and experimental adhesives cured in clinically relevant moist conditions. A0 (FIG. 9A), A8 (FIG. 9B), A16 (FIG. 9C) are control formulations polymerized in the presence of 0, 8 or 16 wt % water; and A0T (FIG. 9A), A8T (FIG. 9B), A16T (FIG. 9C) are experimental formulations containing MPE polymerized in the presence of 0, 8 or 16 wt % water.
Figure 9B:
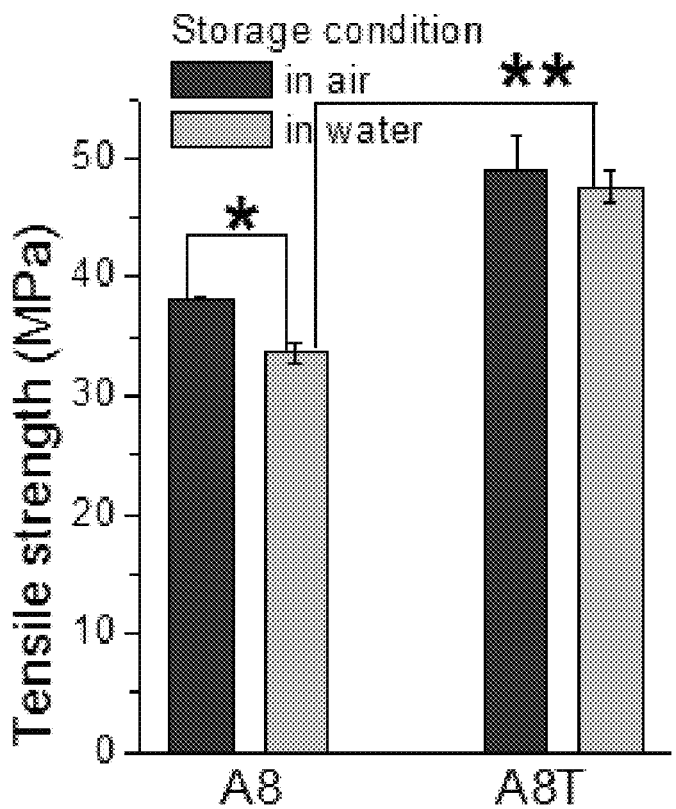
Figure 9C:
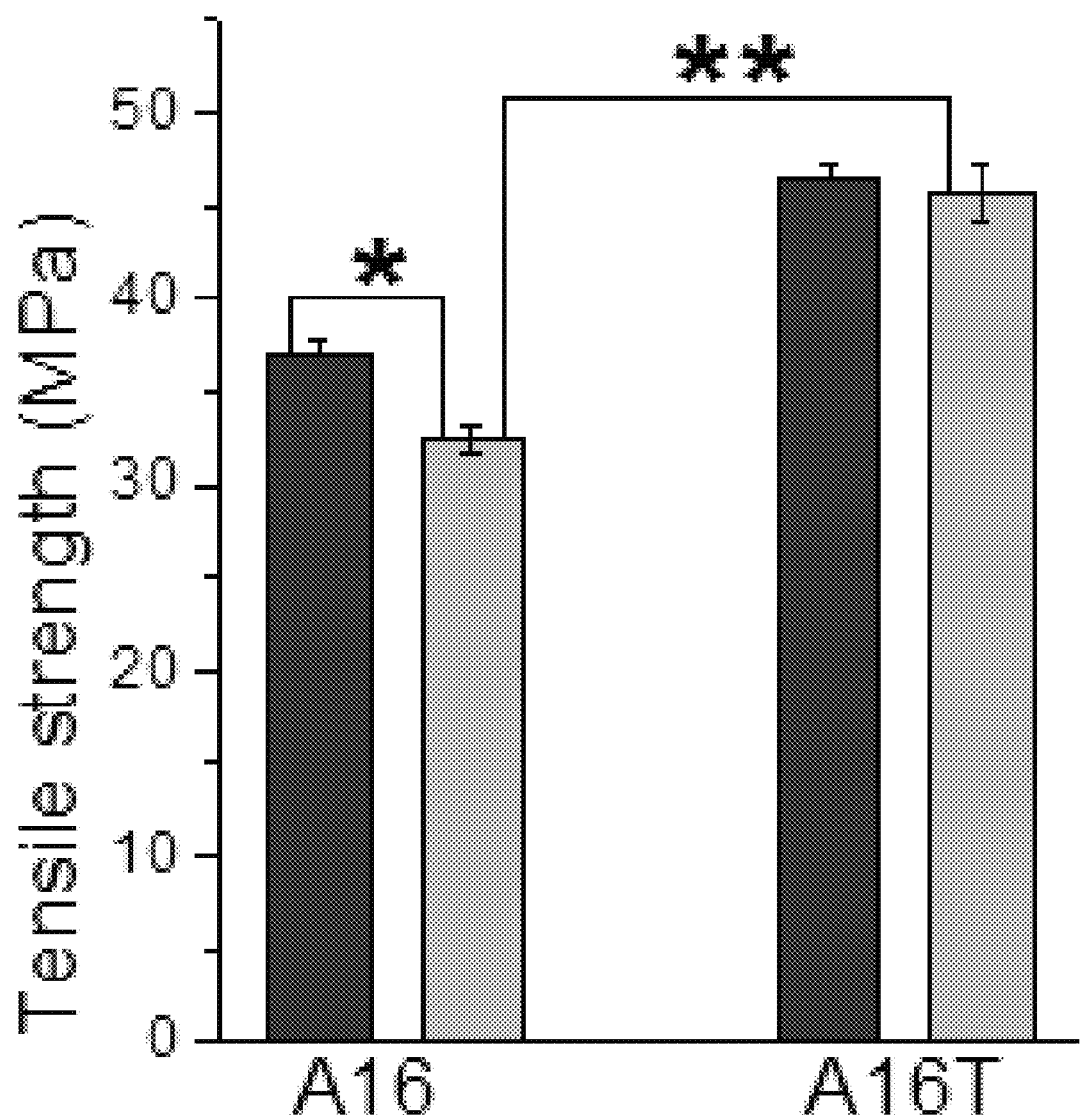

The mechanical properties of dentin adhesives cured in the absence or presence of water are summarized in Table 1 and the comparisons of ultimate tensile strength (UTS) are shown in FIG. 9A-9C.

The ultimate tensile strength (UTS) value of all the samples tested was in the range of 32.4-49.0 MPa. UTS values for control adhesives (A0, A8 and A16) stored for 24 hours in water were significantly lower than for samples stored in air. However, experimental adhesives (A0T, A8T and A16T) showed similar UTS values irrespective of the presence of water and storage conditions (FIG. 9A-9C). For example, the UTS of A0 stored in air was 44.6 MPa, which is similar to that of A0T (45.7 MPa) as a control, while the value for A0T (45.1 MPa) stored in water was significantly greater than that of the corresponding control (A0 stored in water, 37.6 MPa). The experimental adhesives cured in the presence of 8 wt % and 16 wt % water showed significantly greater UTS values than those of controls (Table 1) irrespective of storage conditions. UTS values of control air-stored samples decreased with an increase in water content, while experimental adhesives showed no significant difference (Table 1). Moduli of all specimens were in the range of 0.62~1.18 MPa. For both adhesives, specimens stored in air exhibited significantly higher moduli than samples stored in water (0.62~0.80), following the trend observed in the UTS tests. Moduli of the experimental adhesives were significantly higher when stored in water than those of control. Toughness values for the air-stored adhesives were relatively unaffected by water content, but increased with water storage for 24 h. Control adhesives showed somewhat less toughness than the experimental adhesives (Table 1). Elongation of the resins was in the range of 0.06-0.14%. There was no significant difference in elongation between control and experimental adhesives.

6.

Extracted non-carious, unerupted human third molars stored at 4° C. in 0.9% wt/vol NaCl containing 0.002% sodium azide were used to evaluate the ability of the adhesives to bond with dentin. Teeth were collected after the patients' informed consent was obtained. The teeth were collected under a protocol approved by the University of Missouri Adult Health Sciences institutional review board. In brief, dentin disks were prepared by first cutting the roots at the cementum-enamel junction with a water-cooled low speed diamond saw (Buehler, Lake Bluff, Ill.). The occlusal one-third of the crown was then removed by means of a second, parallel section. Dentin surface without any enamel remnants or exposure of the pulp chamber was prepared. A uniform smear layer was created by abrading the exposed dentin surface with 600 grit silicon carbide under water. Control and experimental adhesives were applied to the prepared dentin surfaces. The dentin surfaces were etched with 35% phosphoric acid gel for 15 seconds and rinsed with distilled water. Excess distilled water was then removed, but the dentin surface was allowed to remain visibly moist. Next, two consecutive coats of the adhesive resin were applied and the surface gently dried using air from an air-water syringe. The adhesive layer was then photo-cured for 40 seconds by exposure to a visible light source, as described previously. The prepared specimens were stored for 24 h in distilled water at 25° C. before being sectioned. The treated dentin surfaces were sectioned perpendicular and parallel to the bonded surfaces using a water-cooled low-speed diamond saw. The resulting dentin/adhesive specimens were rectangular slabs (~8 mm×~2 mm×1.5 mm).

7.

Rectangular, 8 mm×2 mm×1.5 mm, slabs of dentin/adhesive specimens were mounted on a poly(methyl methacrylate) support and 5 μm-thick sections were cut from the face of the slab using a tungsten carbide knife mounted on a Polycut S "sledge" microtome (Leica, Deerfield, Ill., USA). The sections were mounted on glass microscope slides previously treated with Haupt's adhesive (1% gelatin in water with 2% phenol crystals and 15% glycerine), which is used to keep the sections attached to the glass slide during the subsequent staining procedures. Differential staining of the microtomed sections was accomplished with Goldner's trichrome. Stained sections were dehydrated, cover-slipped with mounting media and observed under a Nikon E 800 light microscope.

Figure 10A:
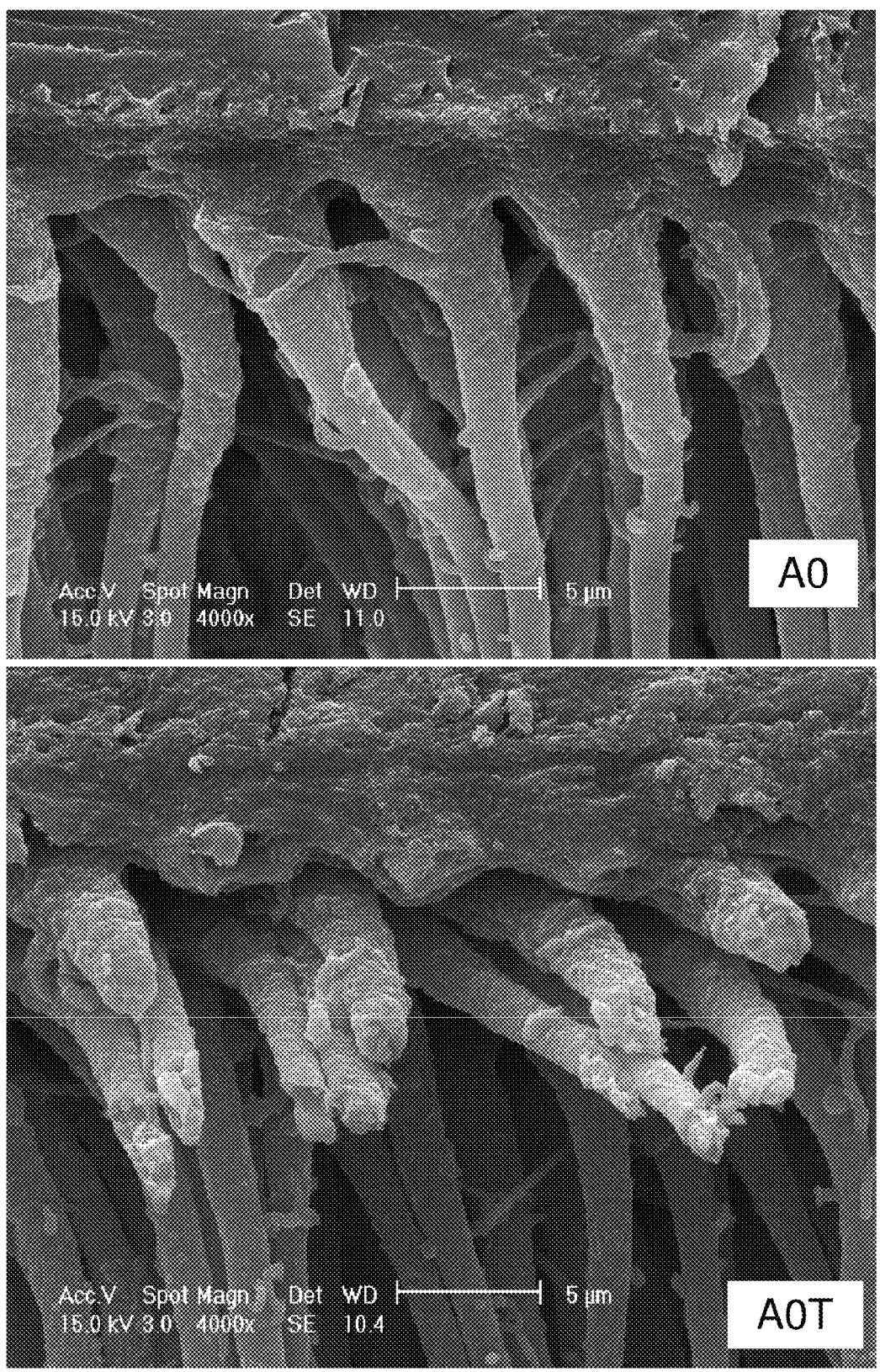
FIGS. 10A-10B are representative SEM micrographs (FIG. 10A) and staining/light microscopy (FIG. 10B) of dentin/adhesive interface for control (A0) and experimental (A0T) resins. The SEM images indicated good resin penetration into the prepared dentin surface for both adhesive formulations. The staining light micrographs of adhesive/dentin interfaces stained with Goldner's trichrome clearly show an interface in which the dentin structure is connected with the adhesive resin. Adhesive resin composition: (A0:HEMA/Bis-GMA=45/55 w/w ratio+40 wt % EtOH; A0T:HEMA/Bis-GMA/MPE=45/30/25 w/w ratio+40 wt % EtOH).
Figure 10B:
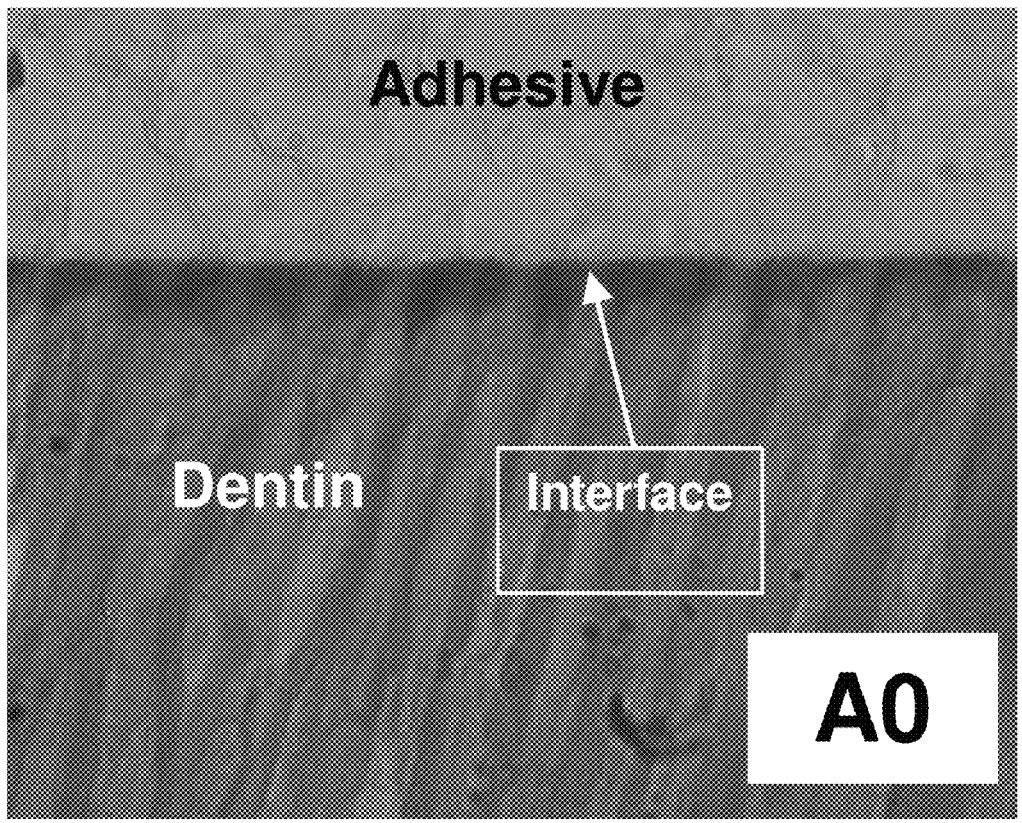
Figure 10B:
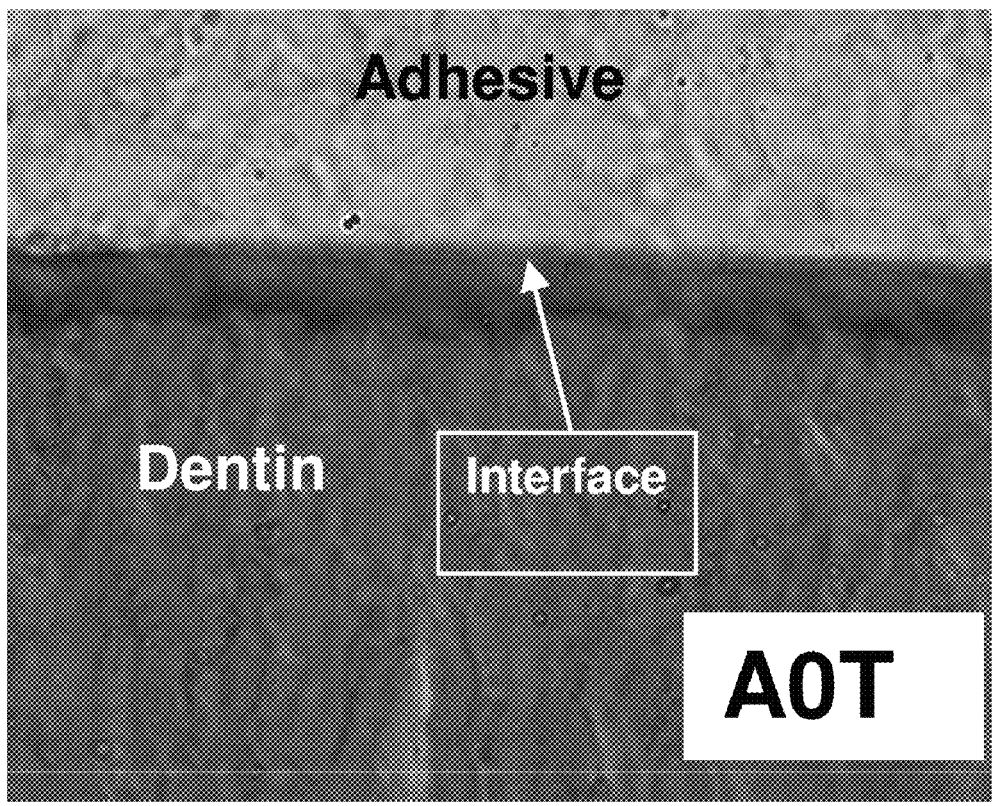

Representative optical micrographs of Goldner's trichrome stained sections of the adhesive/dentin interface are shown in FIG. 10B (control: A0; experimental: A0T). Using this staining technique, mineralized dentin collagen is stained green, unprotected exposed collagen/protein is stained red and pure adhesive is either stained pale yellow or not stained. Both micrographs clearly showed an interface which connected the dentin structure with the adhesive resin (FIG. 10B). The width of the interface zone treated with control adhesive is about 2.4 μm, while the experimental adhesive is 3.5 μm in width. However, Finger et al. found no correlation between interface thickness and the bond strength of adhesive resins, suggesting that bond strength is determined by the quality of the interface rather than its thickness.

8.

The in vitro penetration of adhesive resin into the dentin and the micromorphology of the resin-dentin interface were observed by scanning electron microscopy. The sectioned specimens were treated with 5N HCl for 15 s and 5% NaOCl for 30 min. After rinsing with distilled water, the specimens were dehydrated using a graded series of ethyl alcohol solutions and air-dried in a fume hood overnight. Following drying, the specimens were mounted on 12 mm aluminum stubs and sputter-coated with gold-palladium. Specimens were then examined at a variety of magnifications using a Field Emission Philips XL30 ESEM-FEG 515 electron microscope (Philips Electron Optics Inc., Hillsboro, Oreg.) at 15 kV.

Representative SEM micrographs of the dentin/adhesive interfaces are shown in FIG. 10A. The exposure technique, in which the sectioned specimen was treated with 5N HCl for 15 s and 5% NaOCl for 30 min, has been commonly used to determine the adhesive penetration into the dentin. Numerous resin tags were observed in both control and experimental adhesives and these were formed by the photopolymerization of adhesive resins that penetrated into the dentinal tubules, indicating good resin infiltration into the prepared dentin surface. Both experimental and control adhesives exhibited a distinct hybrid layer (HL) zone. The thickness of the HL formed by the control adhesives in dentin was approximately 2.5 μm. For the experimental adhesive, the HL thickness was ~3.5 μm. In the micrographs of the experimental adhesive (FIG. 10A; A0T), some resin tags cut by a water-cooled low speed diamond saw are seen on the front side, due to the orientation of the dentinal tubules. The resin tags also showed small lateral branches. Thus, there were no marked differences in the control and experimental adhesives on SEM evaluation.

SEM observations of both control and experimental adhesives showed numerous resin tags and small lateral branches, suggesting good resin penetration into the dentinal tubules. There were no significant differences in the morphology of the adhesive/dentin interfaces for the control and experimental adhesives. SEM observation involves time-consuming specimen preparation and is very sensitive to sample preparation techniques that may alter or even destroy the interface. Many of the disadvantages associated with the SEM specimen preparation technique can be overcome using the staining/light microscopic method. The light micrographs of adhesive/dentin interfaces stained with Goldner's trichrome (FIG. 10B) clearly show an interface in which the dentin structure is connected with the adhesive resin. These thin sections were differentially stained using Goldner's trichrome, a conventional bone stain. The width of the interface was 2.4 and 3.5 μm for the control and experimental adhesives, respectively, consistent with the SEM observations. The SEM images for experimental and control adhesives showed no separation between the adhesive and dentin along the length of the interface, indicating overall structural integrity of the interface.

9.

The model resin consisted of 2,2-bis[4-(2-hydroxy-3-methacryloxypropoxy)phenyl]-propane (BisGMA, Polysciences Inc., Washington, Pa., USA) and hydroxyethyl-methacrylate (HEMA, Acros Organics, NJ, USA) at 55/45 wt/wt ratio. The adhesives were formulated with 0 wt %, 8 wt % and 16 wt % water to simulate the moist environment of the mouth, and were selected on the basis of our previous work. The concentration of water was based on the total final weight of the model resin. When monitoring of the aliphatic C=C bond was employed to determine degree of conversion, heavy water (deuterium oxide, 99.9%, $D_2O$) (Cambridge Isotope Laboratories, Inc. Andover, Mass., USA) was used due to the absence of overlapping water peak at 1640 $cm^{-1}$. Four photoinitiator systems (all from Aldrich, Milwaukee, Wis.) were used. The two-component systems contained camphorquinone (CQ) as a hydrophobic photosensitizer and 2-(dimethylamino)ethyl methacrylate (DMAEMA) as a hydrophilic co-initiator or CQ and ethyl-4-(dimethylamino) benzoate (EDMAB) as a hydrophobic co-initiator. The three-component systems were prepared by adding diphenyliodonium hexafluorophosphate (DPIHP) as the iodonium salt to each of the two-component systems.

10.

Rheological measurements for the liquid resin formulated with or without water were carried out in a TA Instruments AR2000 rheometer (New Castle, Del.) in the controlled-rate mode. The measurements were made at 25° C. with 40 mm diameter and 2° cone angle in the shear rate range of 10/s to 100/s, at 10 points per decade to generate data on shear stress ($\tau$) and shear rates ($\gamma$). The viscosities of the resin solutions ($\eta$) were evaluated from the equation: $\eta=\tau/\gamma$.

Figure 11:
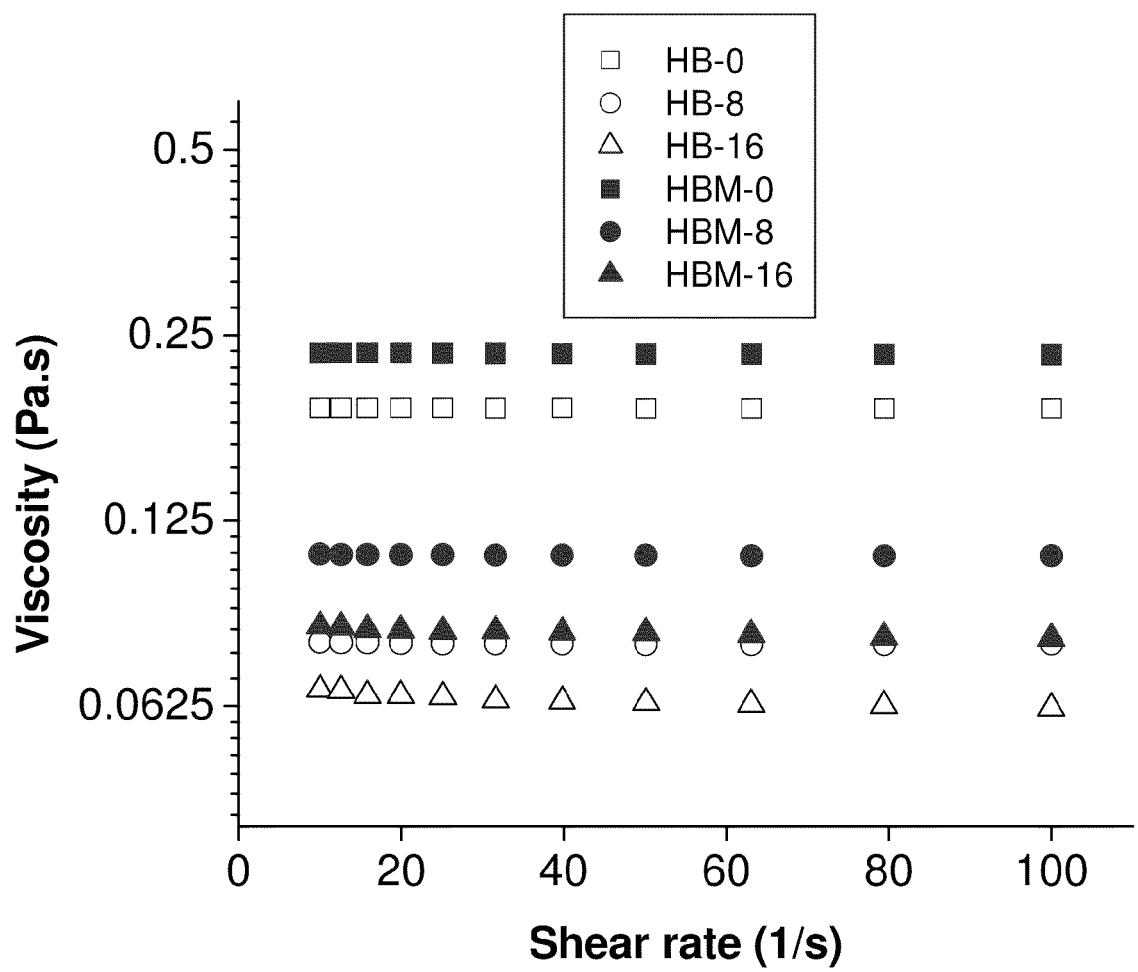
FIG. 11 is a graph that shows the viscosities of adhesive resins containing different water content as a function of shear rate at 25° C. Abbreviations: BH-0=bisGMA/HEMA=55/45+0 wt % water; BH-8=bisGMA/HEMA=55/45+8 wt % water; BH-16=bisGMA/HEMA=55/45+16 wt % water.

FIG. 11 shows the measured viscosities of adhesive resins with different water content as a function of shear rate at 25° C. Typical Newtonian behavior, with viscosity independent of shear rates, is observed. The viscosity of resin solution decreased in the order (mPa·s): HBM-0 (233.7)>HB-0 (190.6)>HBM-8 (110.1)>HBM-16 (82.7)>HB-8 (79.17)> HB-16 (64.5). As expected, the viscosities of the resin solutions decrease with increasing water content.

Table 2 shows the degree of conversion (DC) and the curing time (CT) of adhesive resins containing different photoinitiator systems. For the two-component systems, DC values of samples initiated by CQ/DMAEMA (i.e., CD-0, CD-8, CD-16) are lower than those for the other three photoinitiator systems. Significantly, DC values for samples initiated by CQ/DMAEMA are decreased dramatically by polymerization in the presence of water, from ~75% in the absence of water (CD-0, Table 2) to ~38% with water (CD-8, CD-16, Table 2) Including DPIHP significantly increased the DC for all photoinitiator systems, regardless of the presence of water (Table 2). For example, incorporation of DPIHP into the CQ/DMAEMA system increased the DC from 75% (CD-0, Table 2) to 88% (CDD-0, Table 2) for the adhesives cured in the absence of water. In the presence of 8% water, the DC increased from 38% (CD-8, Table 2) to 94% (CDD-8, Table 2). Similarly, the incorporation of DPIHP into the CQ/EDMAB system increased the DC from 85% (CE-8, Table 2) to 97% (CED-8, Table 2) in the presence of 8 wt % water.

The curing time (CT) in the two-component systems was greater than in the three-component systems, and even longer in the presence of water (Table 2). Interestingly, the CQ/DMAEMA system showed a CT of 33 seconds in the absence of water (CD-0, Table 2), but is too long to measure in the presence of water (CD-8, CD-16, Table 2). The resulting resins have a low DC and gel-like consistency. The CT values in the three-component systems were on the order of 5 seconds, and were unaffected by the presence of water.

Incomplete polymerization can compromise the performance of resin-based dental restoratives. The presence of residual monomer can have a plasticizing effect on the polymer, thereby altering the physical and mechanical properties of the hardened materials. In addition, the presence of unreacted monomer can make the polymeric matrix more susceptible to oxidative and hydrolytic degradation reactions, leading to poor durability. It is important, therefore, to evaluate the final degree of conversion of monomer to polymer after polymerization. The studies reported here showed dramatic differences in DC and CT of bisGMA/HEMA resin between the two-component (CQ/DMAEMA and CQ/EDMAB) and three-component systems (CQ/DMAEMA/DPIHP and CQ/EDMAB/DPIHP) (Table 2). Moreover, the resin formulated with the aliphatic amine (i.e., DMAEMA) showed significantly lower DC and longer CT than the resin formulated with the aromatic amine (i.e., EDMAB), especially in the presence of water. This result is in agreement with previous findings that demonstrated a faster polymerization rate and higher DC with the CQ/aromatic amine initiator system. The addition of DPIHP to the two-component initiator systems thus increased DC and reduced CT dramatically.

11.

Rectangular beam specimens (1×1×11 mm$^3$) cured in a glass-tubing mold (Wilmad Labglass, #LG-25001-100, Standard wall borosilicate tubing) were prepared for the determination of dynamic mechanical properties and degree of conversion (DC). The model adhesives were light-cured for 40 sec at room temperature with a commercial visible light-curing unit (Spectrum® 800, Dentsply, Milford, Del., USA) at an intensity of 550 mW cm$^{-2}$ placed at a distance of 1 mm according to a protocol published previously. The polymerized samples were stored at room temperature for 2 days in a dark room, and then for 1 week in a vacuum oven in the presence of a drying agent.

The DC of the methacrylate double bond was obtained using a LabRAM ARAMIS Raman spectrometer (LabRAM HORIBA Jobin Yvon, Edison, N.J.) with a HeNe laser ($\lambda=633$ nm, a laser power of 17 mW) as an excitation source. The instrument conditions were: 200 µm confocal hole, 150 µm wide entrance slit, 600 gr/mm grating, and 10×objective Olympus lens. Data processing was performed using LabSPEC 5 (HORIBA Jobin Yvon). The samples were mounted in a computer-controlled, high-precision x-y stage. To determine the DC, spectra of the uncured resins and beam samples were acquired over a range of 700-1800 cm$^{-1}$. The change of the band height ratios of the aliphatic carbon-to-carbon double bond (C=C) peak at 1640 cm$^{-1}$ and the aromatic C=C at 1610 cm$^{-1}$ (phenyl) in both the cured and uncured states was monitored and DC was calculated by using the following equation based on the decrease in the intensity band ratios before and after light curing: DC (%)=[1−($R_{cured}$/$R_{uncured}$)]×100, where R=band height at 1640 cm$^{-1}$/band height at 1610 cm$^{-1}$.

Curing time was evaluated by inserting a metal rod into the center of the adhesive resin immediately after placing the material into a two-end open glass tubing. The curing time was taken as the period from which the light exposure was initiated to the moment at which the metal rod could not be moved by hand, and reported as the average of four readings.

12.

The viscoelastic properties of the polymerized dentin adhesives were characterized using DMA Q800 (TA Instruments, New Castle, USA) with a three-point bending clamp. In DMA, a sinusoidal stress is applied and the resultant strain is measured. The properties measured under this oscillating loading are storage modulus, loss modulus, and tan δ. The storage modulus (E') represents the stiffness of a viscoelastic material and is proportional to the energy stored during a loading cycle. The loss modulus (E") is related to the amount of energy lost due to viscous flow. The ratio of loss (E") to storage modulus (E') is referred to as the mechanical damping, or tan δ. For the DMA test, the temperature was varied from −20 to 200° C. with a ramping rate of 3° C./min at a frequency of 1 Hz. No pre-heating cycle was applied, and the storage modulus and tan δ were recorded as a function of temperature. The tan δ value goes through a maximum as the polymer undergoes the transition from the glassy to the rubbery state. The glass transition temperature (Tg) was determined as the position of the maximum on the tan δ vs. temperature plot. Five specimens of each material were measured and the results averaged.

Figure 12A:
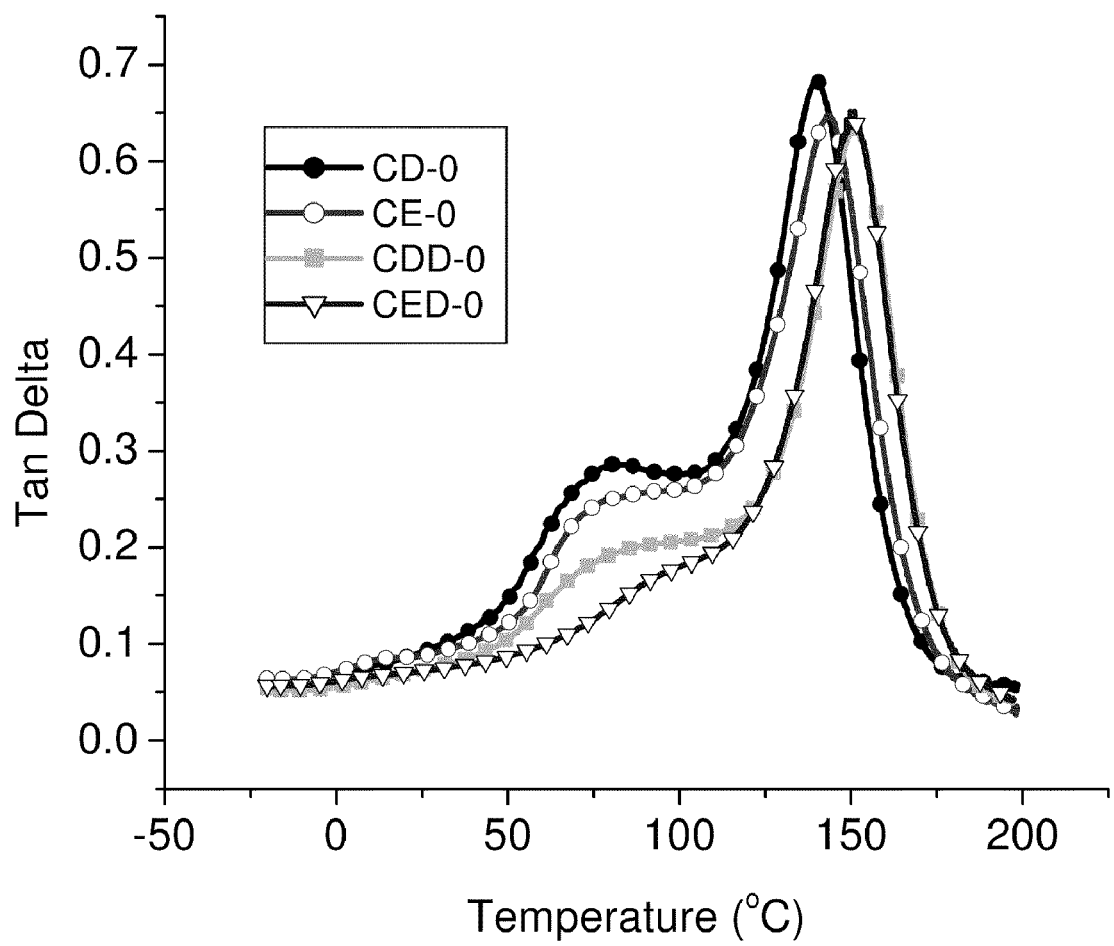
FIGS. 12A-12g are graphs showing representative tan delta curves of dentin adhesives containing different water content and different photoinitiators as a function of temperature.
Figure 12B:
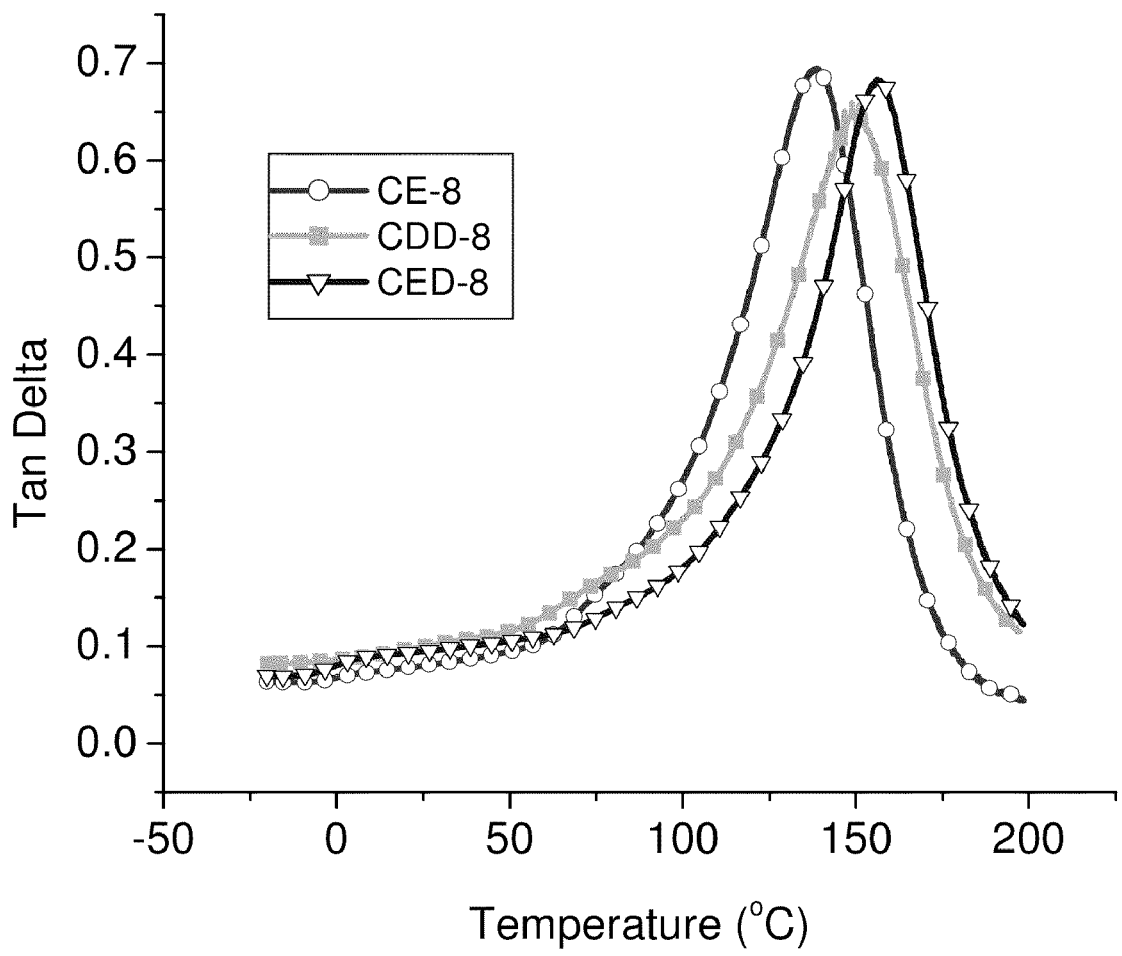
Figure 12C:
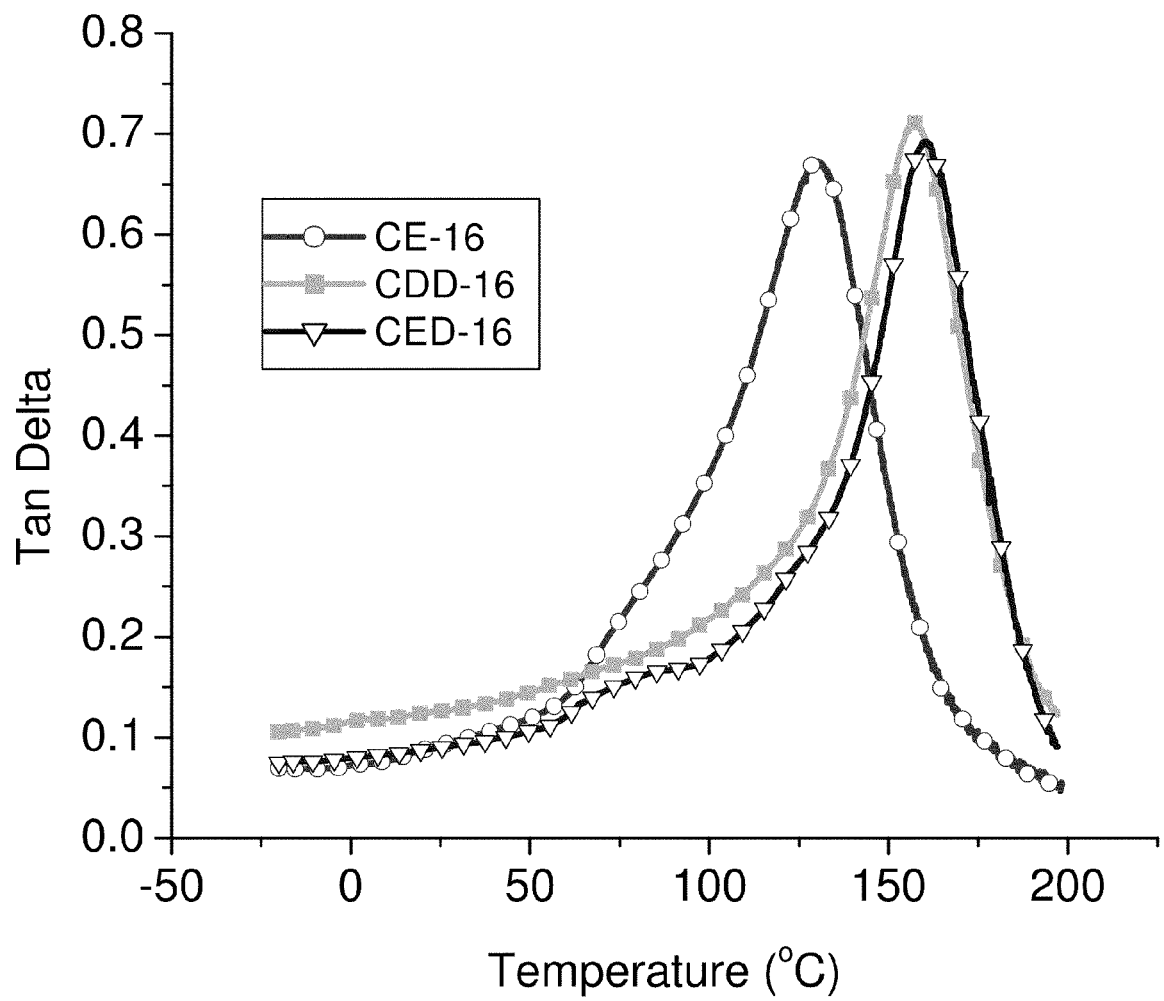
Figure 13A:
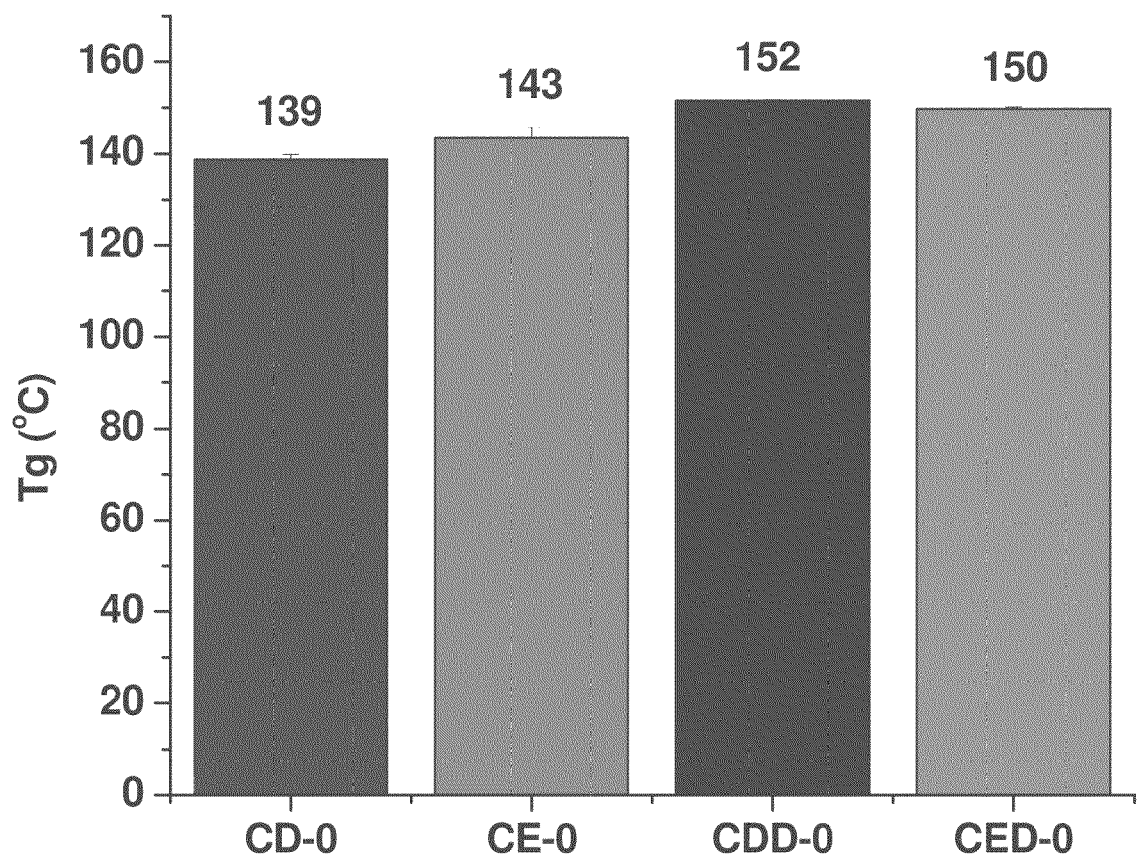
FIGS. 13A-13G are graphs that show representative average glass transition temperatures of dental adhesives containing different water content and different photoinitiators as a function of temperature.
Figure 13B:
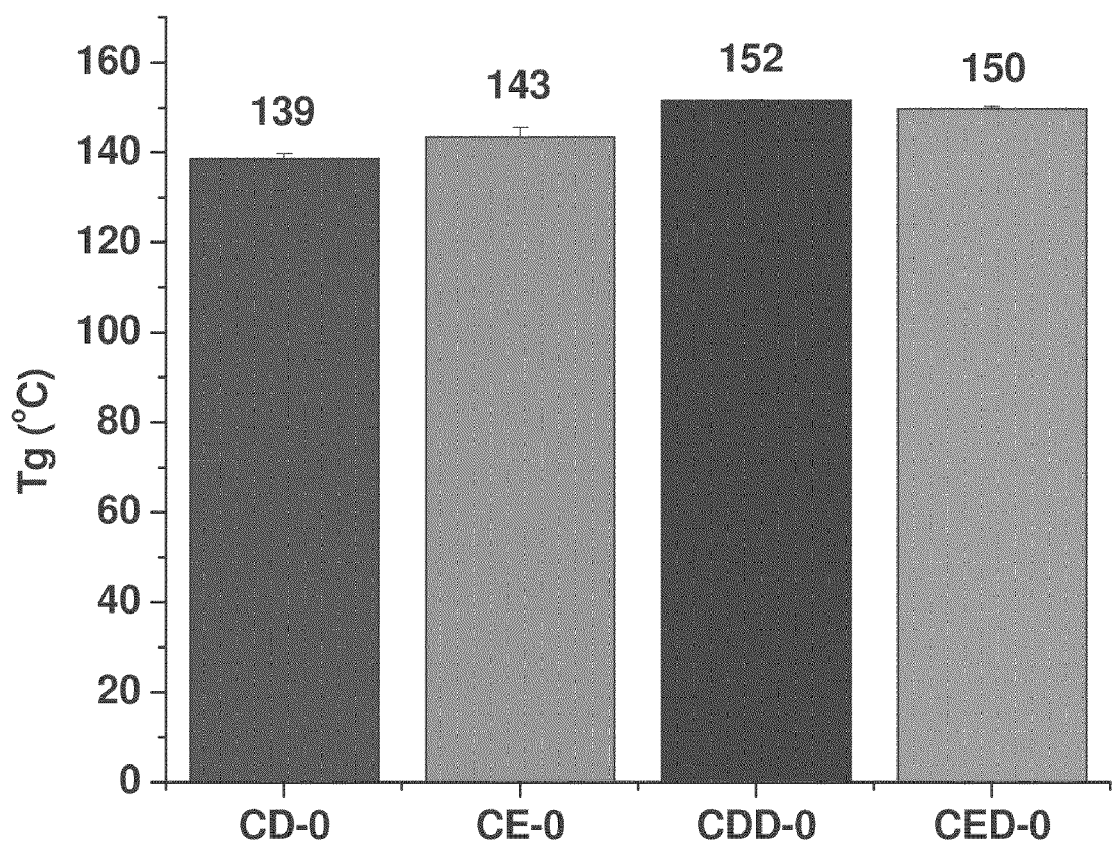
Figure 13C:
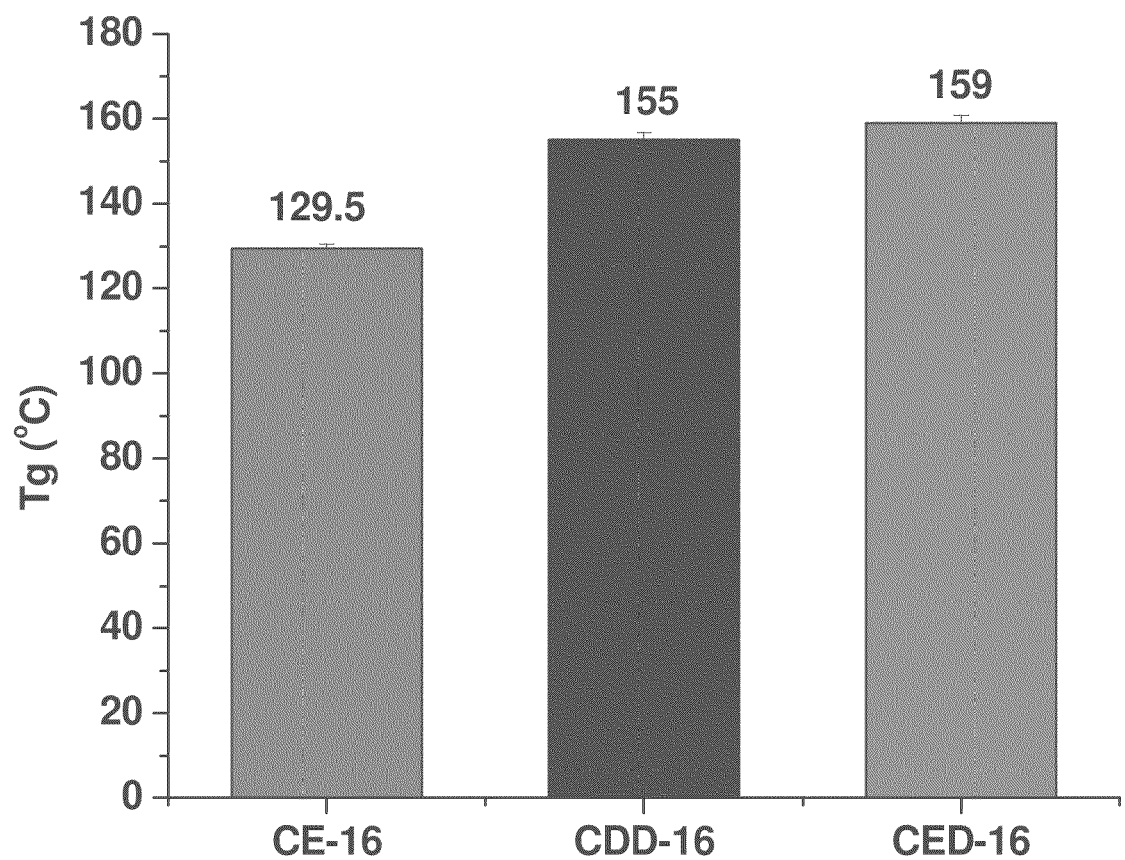

FIGS. 12A-12C show tan δ values as a function of temperature, and FIGS. 13A-13C show the average glass transition temperatures (Tg) of model adhesives cured in the absence and presence of water. The tan δ values gradually increased with increasing temperature for all samples tested, reaching a maximum in the glass transition region (FIG. 12A-12C). Samples cured in the absence of water showed a shoulder at low temperature, a feature generally absent for samples cured in the presence of water (FIG. 12A-12C). As mentioned above, the sample formulated with CQ/DMAEMA as two-component system and cured in the presence of water was gel-like, and so could not be tested by DMA. As shown in FIGS. 13A-13C, Tg values for samples polymerized with the CQ/EDMAB system were lower (130 to 143° C.) than those for the three-component systems (151 to 159° C.), regardless of the presence of water. Tg values for the two-component photoinitiator systems decreased slightly with increasing water content, while those for the three-component photoinitiator system showed no change or a slight increase with increasing water content.

Figure 12D:
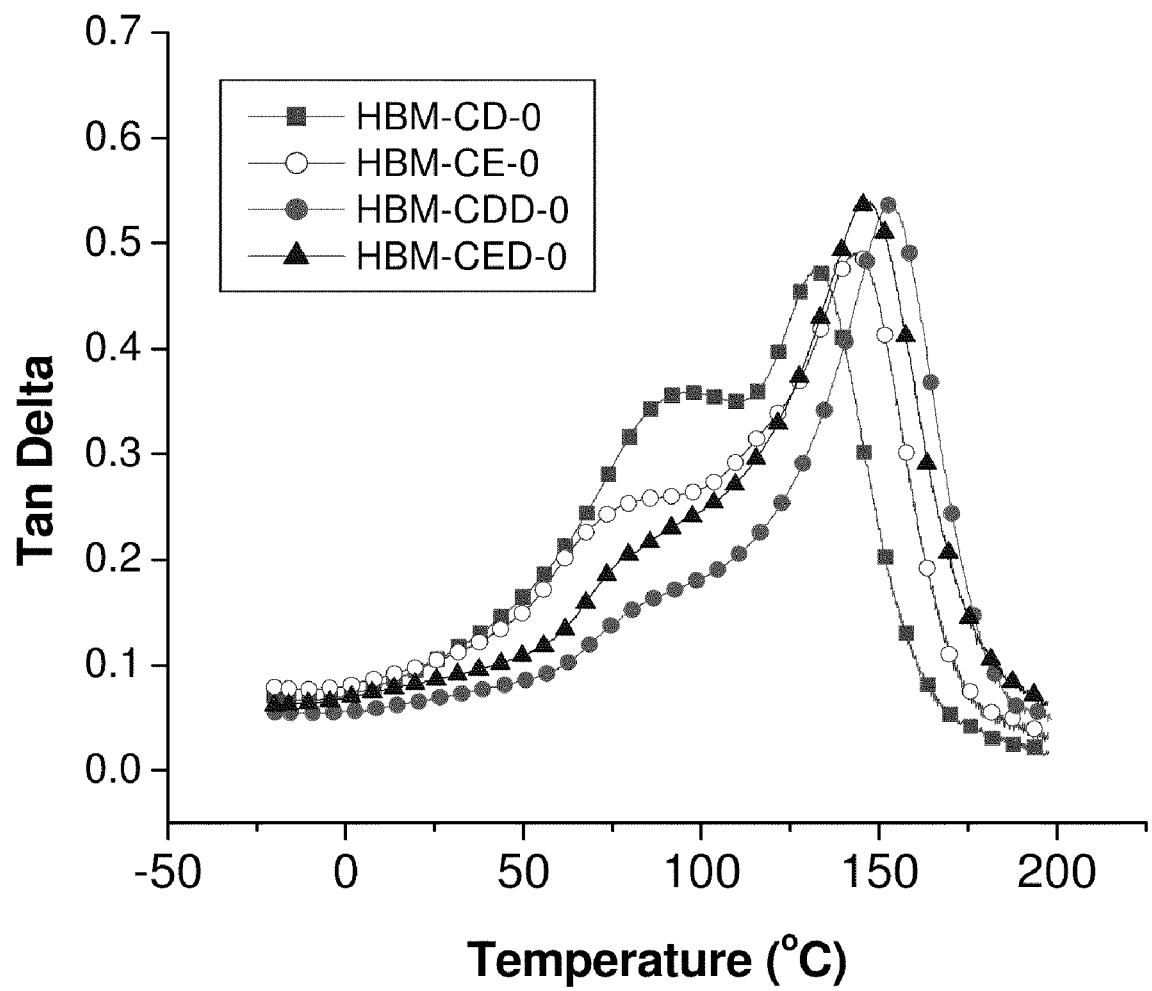
Figure 12E:
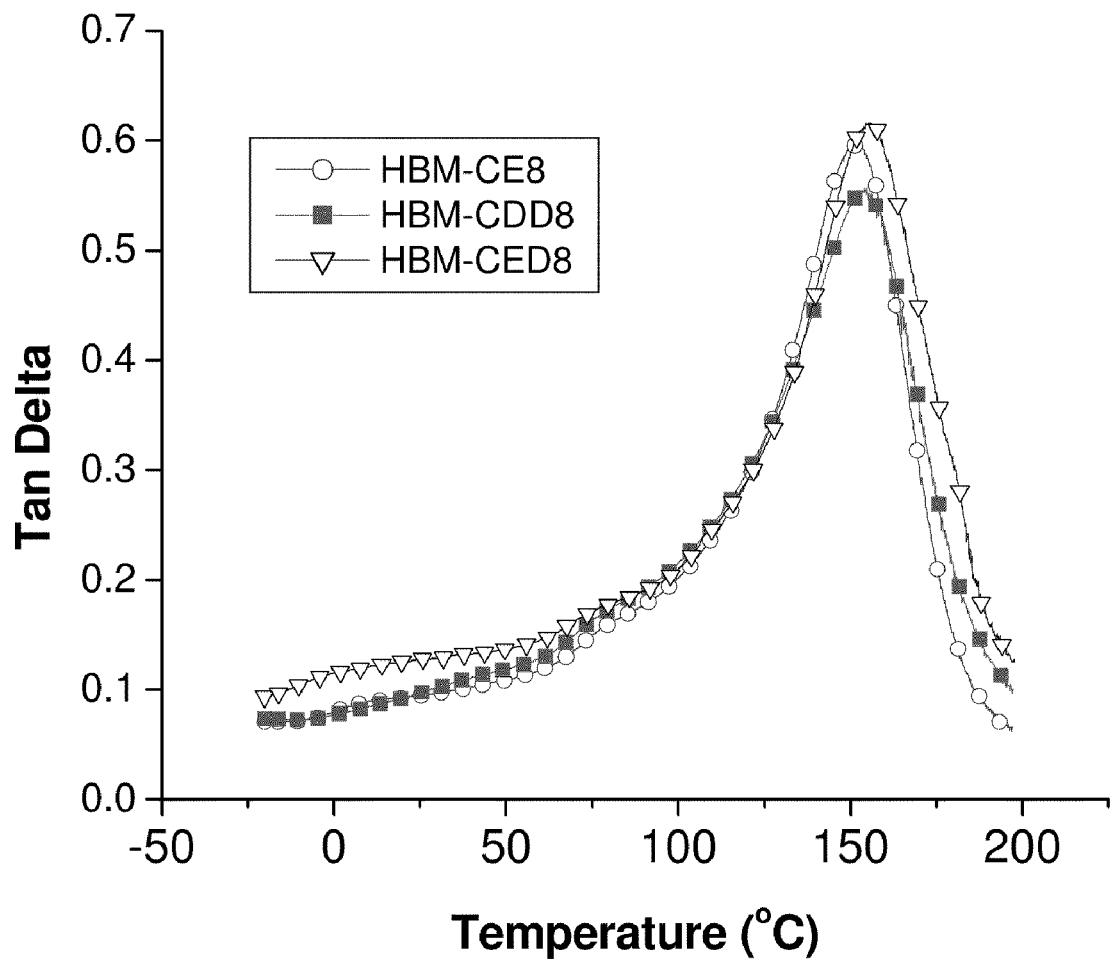
Figure 12F:
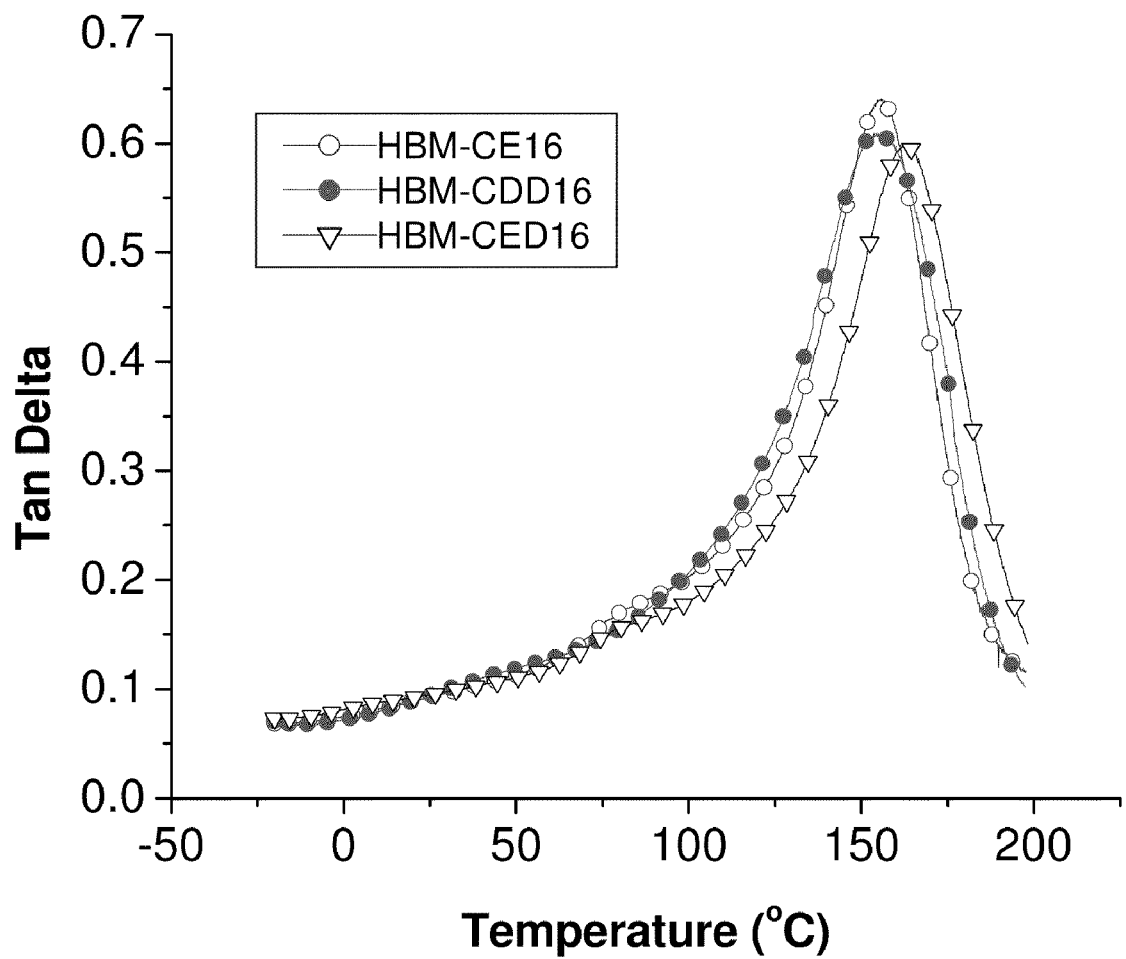

As shown in FIG. 12D-12F, the tan δ values gradually increased with increasing temperature for all samples tested, reaching a maximum in the glass transition region. Samples cured in the absence of water showed a shoulder at low temperature, a feature generally absent for samples cured in the presence of water (FIG. 12D). The sample formulated with CQ/DMAEMA as two-component system and cured in the presence of water was gel-like, and so could not be tested by DMA. In addition, Tg values for samples polymerized with the CQ/EDMAB system were lower (145 to 157° C.) than those for the three-component systems (CQ/EDMAB/DPIHP system: 146 to 163° C.).

Figure 12G:
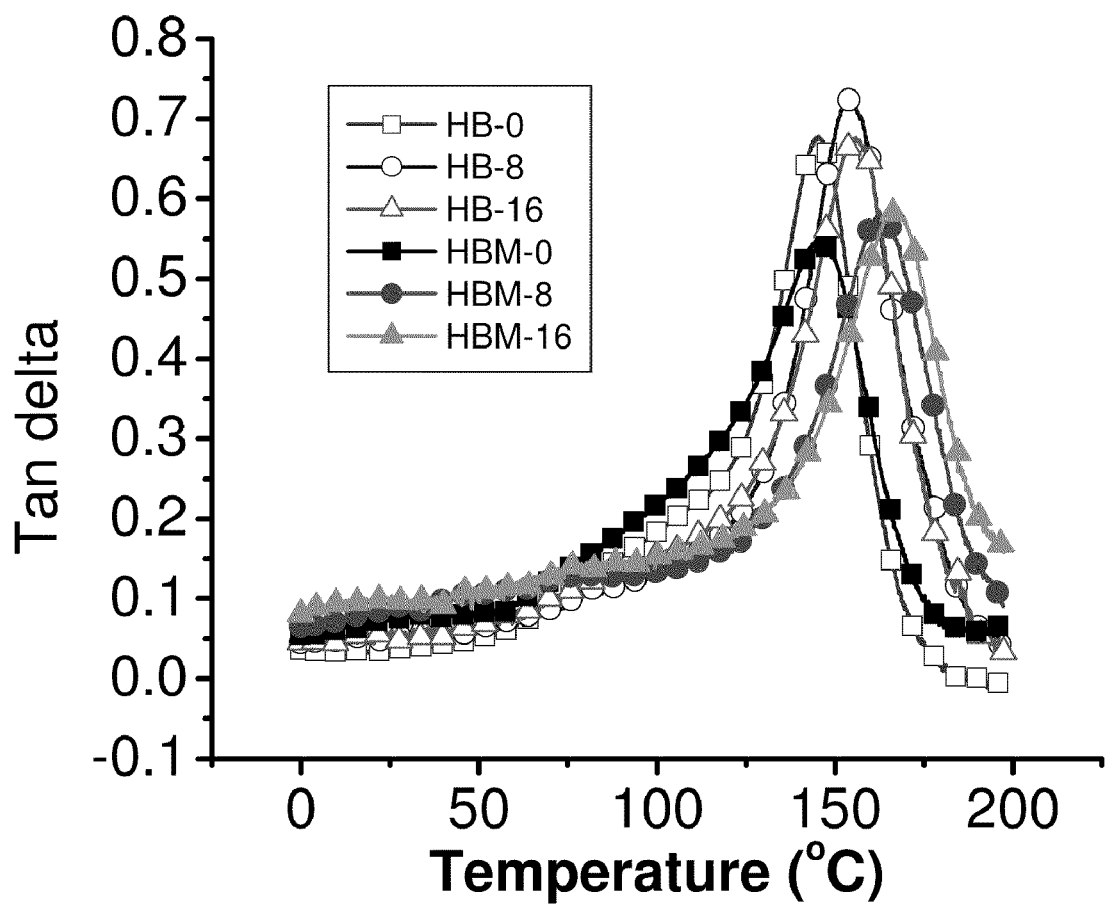
Figure 13D:
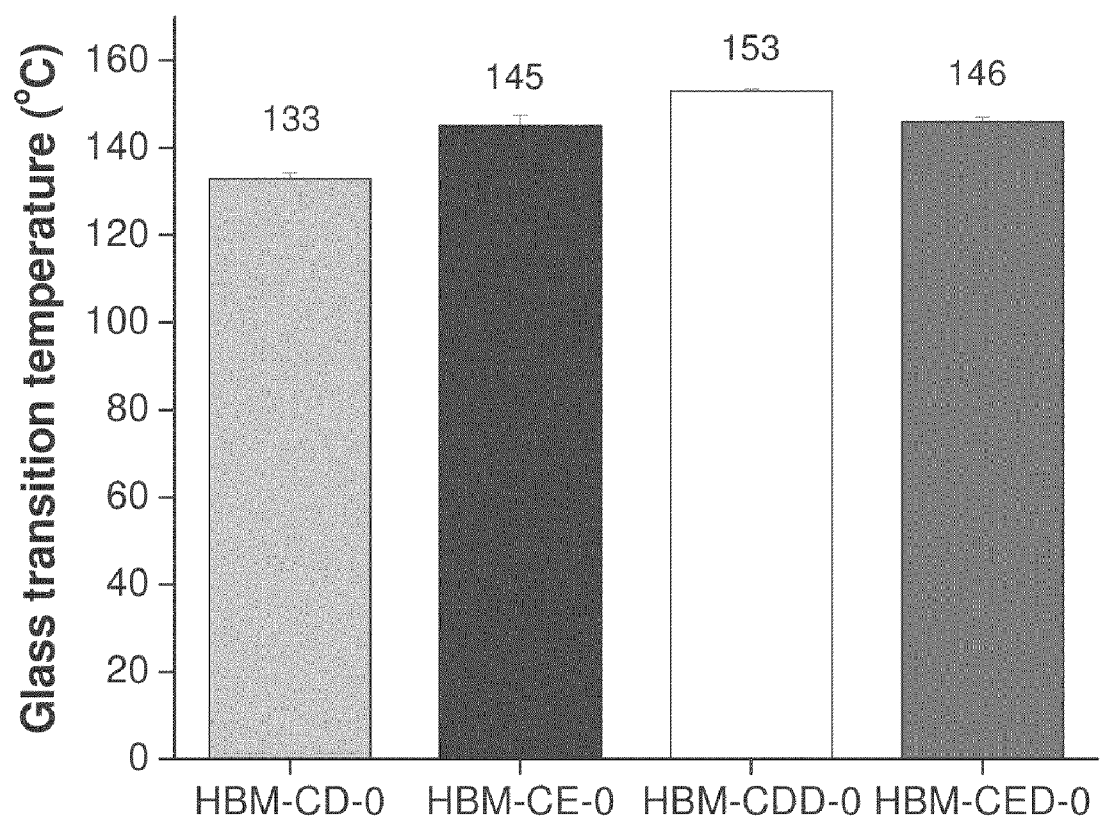
Figure 13E:
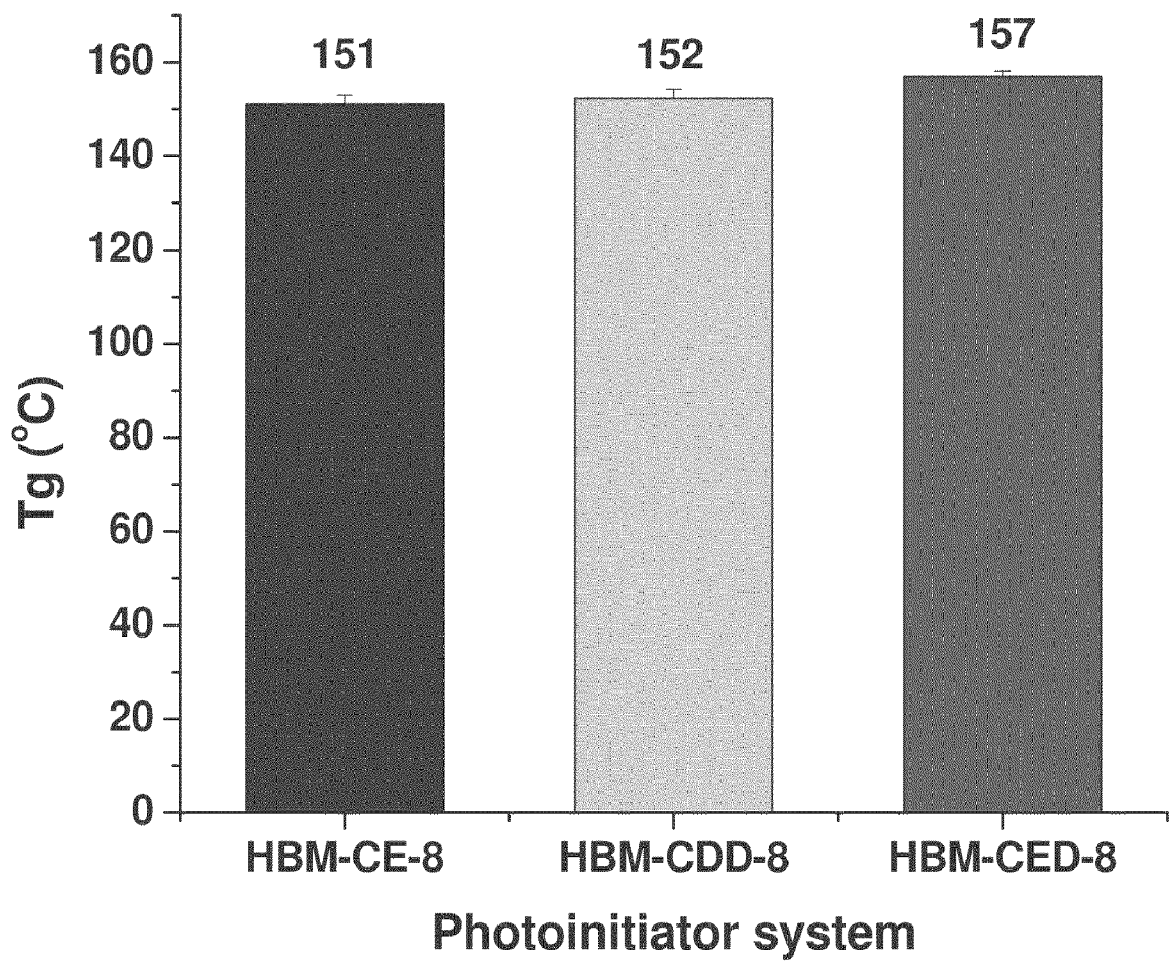
Figure 13F:
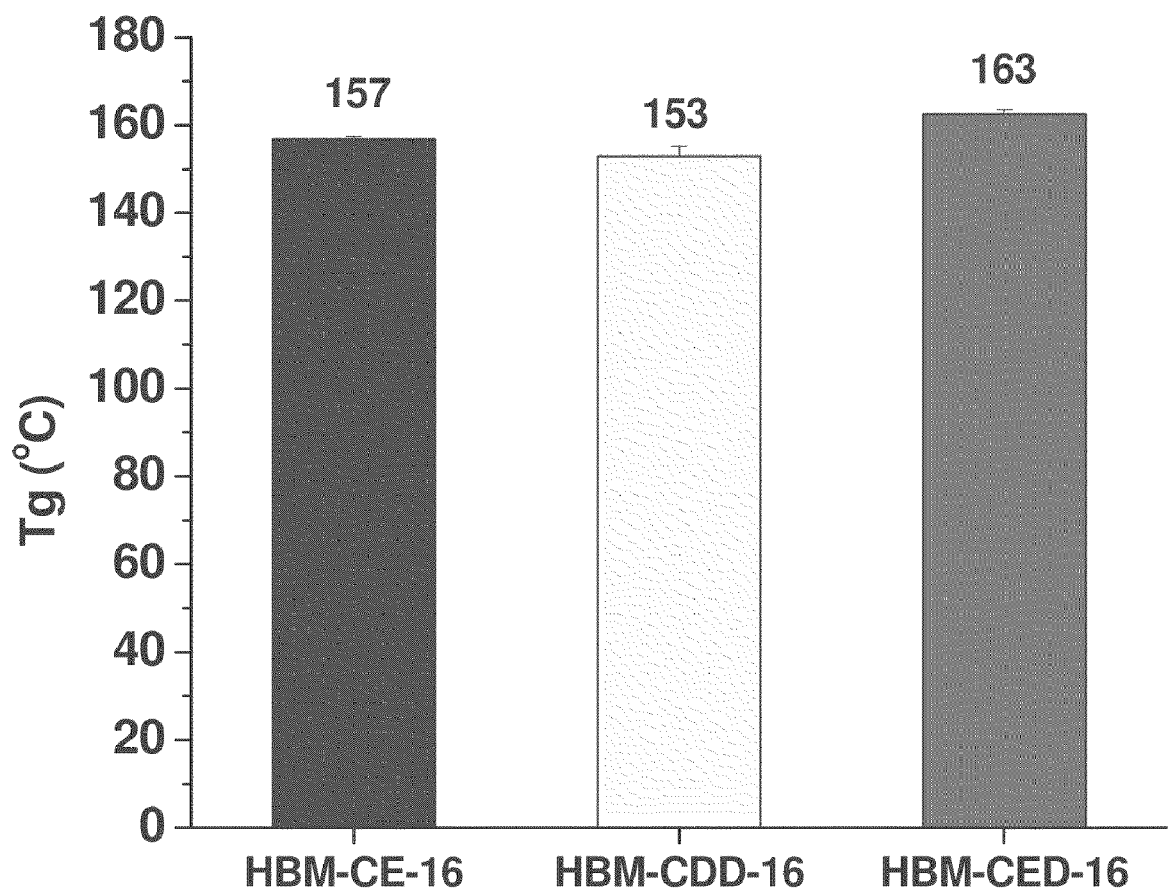
Figure 13G:
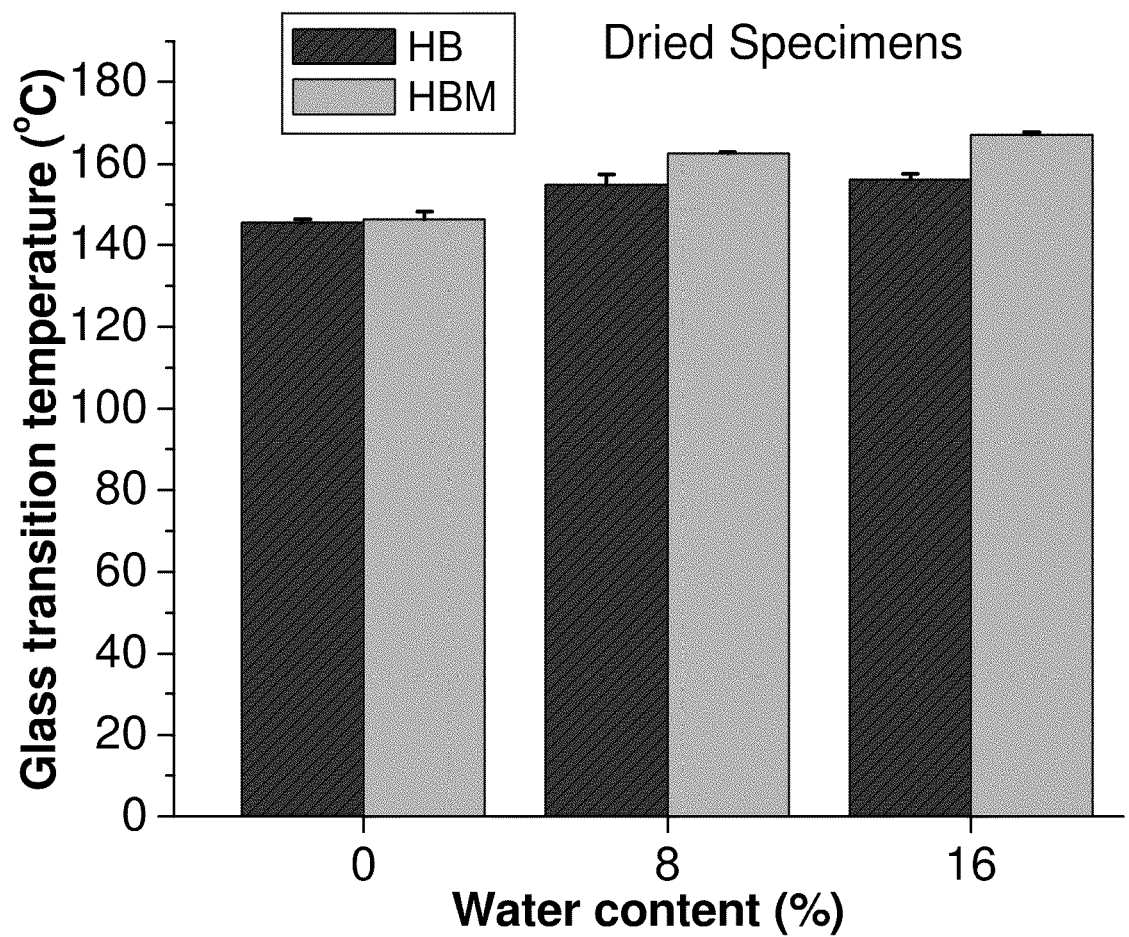

As shown in FIGS. 12G and 13G, broad tan δ peaks were obtained for all samples, indicating that the formed networks are inhomogeneous. The intensity of the tan δ peak at the Tg temperature reflects the extent of mobility of the macromolecular chain segments at this temperature. The HBM exhibits a smaller tan δ peak as compared to the HB, suggesting higher elastic polymer than HB. HBM cured in the presence of water showed significant higher Tg than those of the control.

FIGS. 13D-13F show the average glass transition temperatures of dentin adhesives containing new monomer, MPE, different water content, and different photoinitiators as a function of temperature ((FIG. 13D) : 0 wt % water; (FIG. 13E): 8 wt % water; (FIG. 13F): 16 wt % water in adhesive).

Because DMA gives information on the relaxation of molecular motions which are sensitive to structure, it can be used to provide information on the properties of polymer networks, such as storage modulus, glass transition temperature and structural heterogeneity. DMA is particularly suitable for determining glass transitions because the change in modulus is much more pronounced in DMA than, for example, the heat capacity change in a DSC measurement. High Tg values are generally desirable for dental restoratives, since creep and distortion resulting from consuming hot fluids and foods are minimized with high Tg materials. The widths of the tan δ curves indicate that the glass transition occurs over a wide range of temperature rather than at a specific temperature. This broad glass transition can be attributed to the fact that the polymerization of multifunctional monomers produces heterogenous networks containing both highly crosslinked and less densely crosslinked regions. The main peaks of the tan δ curve correspond to polymer main chain relaxation. The shoulder at lower temperature for adhesives cured in the absence of water can be attributed to relaxation of chain segments for different crosslinked regions, which may be associated with the restriction of mobility of the propagating radicals with relatively high viscosity in a bulk solution without water. Interestingly, it can be seen that adhesives containing three-component photoinitiator systems showed Tg values that remained constant or increased with increases in water content. In contrast, the polymer cured with the two-component CQ/DMAEMA system in the presence of water was gel-like and could not be tested mechanically, while the Tg of polymers cured with CQ/EDMAB system decreased with increasing water content. These results indicate that Tg is influenced by not only DC, but also by crosslink density; although CQ/EDMAB system gives higher DC as water content is increased, crosslink density may be different due to the poor compatibility of monomers with initiators and micro-phase separation in the presence of water.

Figure 14A:
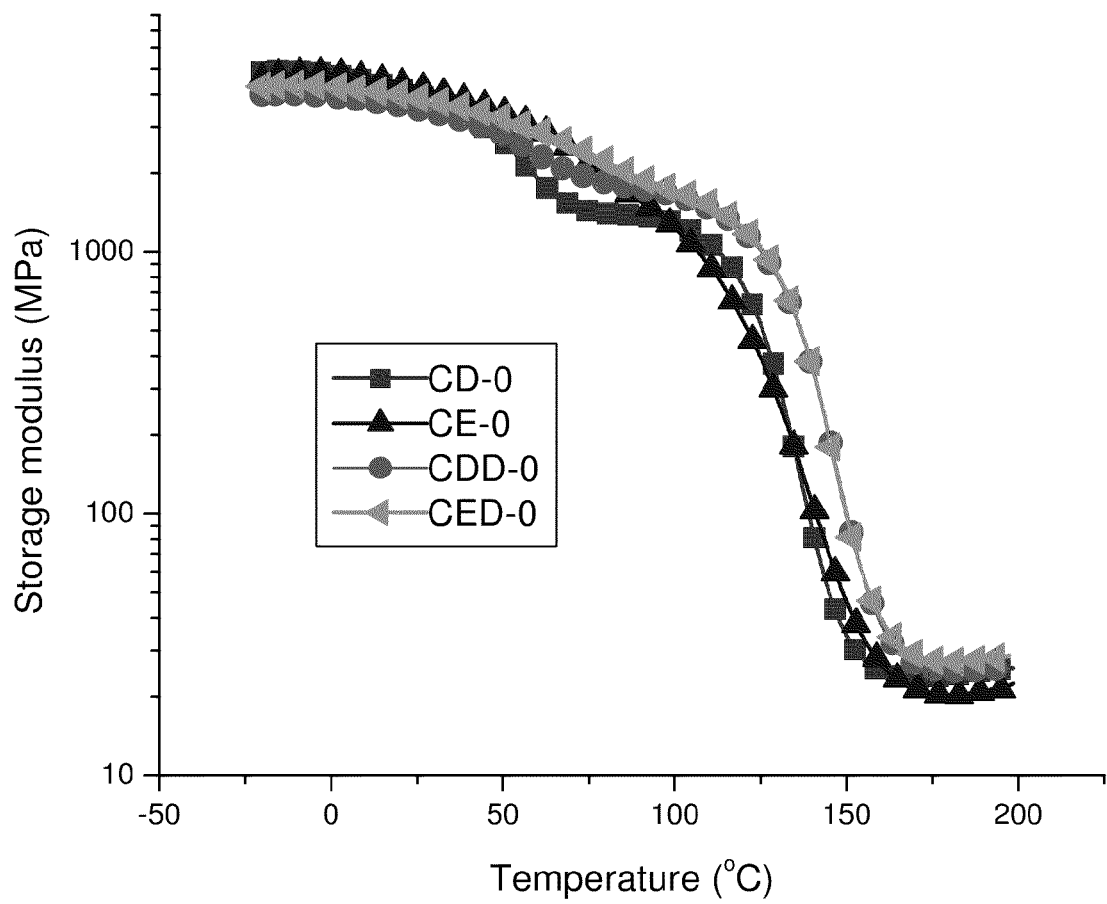
FIGS. 14A-14H are graphs that show the representative storage modulus of adhesives containing different photoinitiator systems and different water content as a function of temperature and/or water content.
Figure 14B:
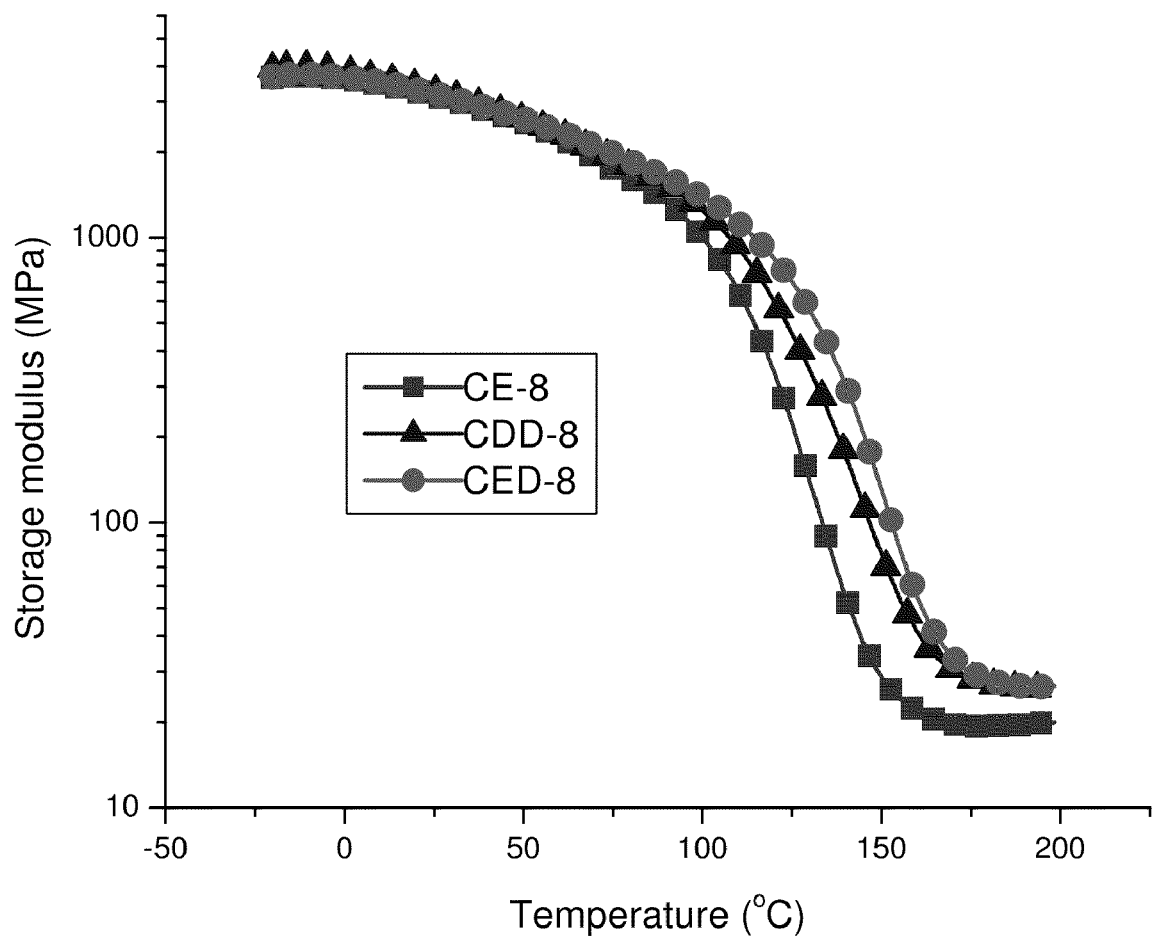
Figure 14C:
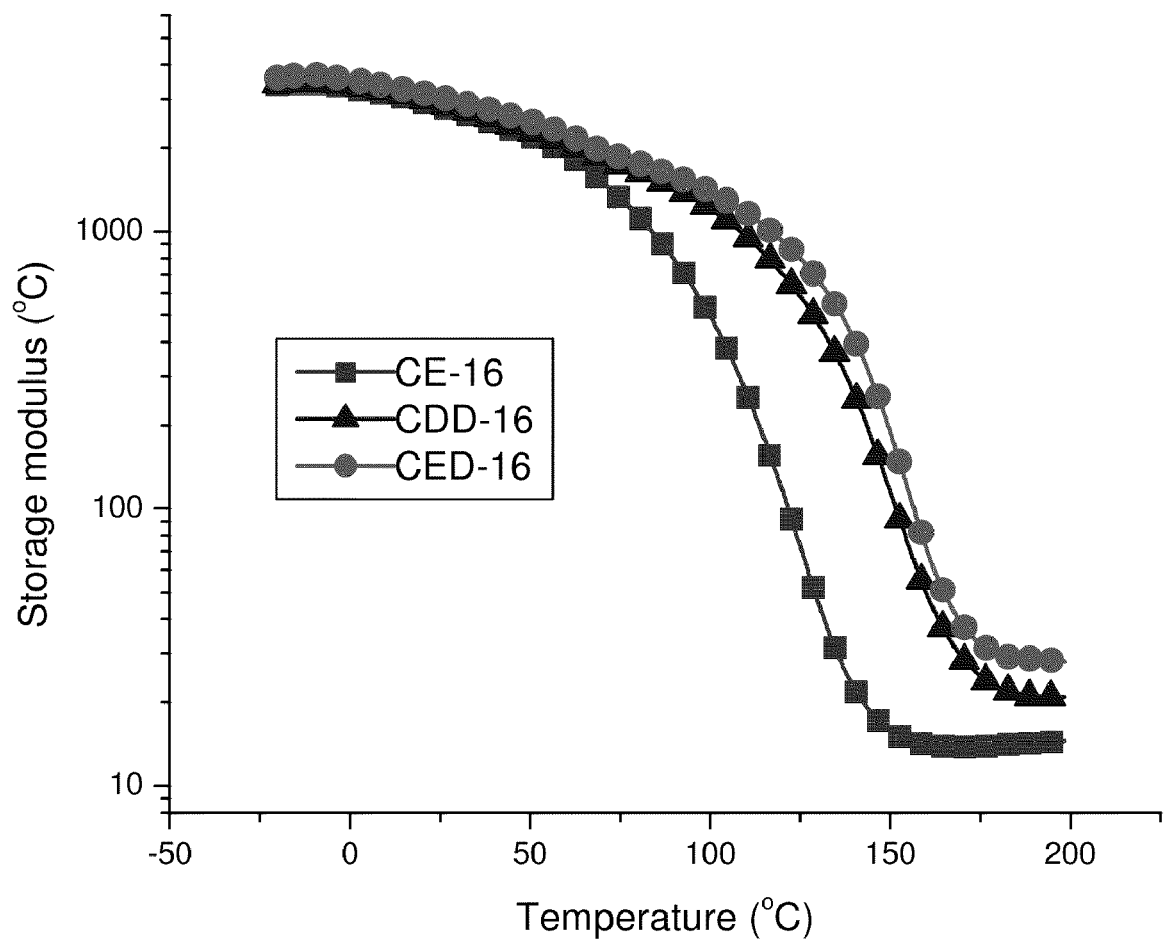

FIG. 14A-14C shows the representative storage modulus of adhesives containing different photoinitiator systems and water content as a function of temperature. Storage modulus values for polymer networks cured in the absence of water are in the range of 3.4~3.7 GPa at 37° C. and in the range of 21~26 MPa at temperatures in the rubbery plateau region. Similar values of storage modulus were obtained for all systems at 37° C., regardless of water content. However, somewhat higher values were obtained for three-component systems in the rubbery region cured in the presence of water.

Figure 14D:
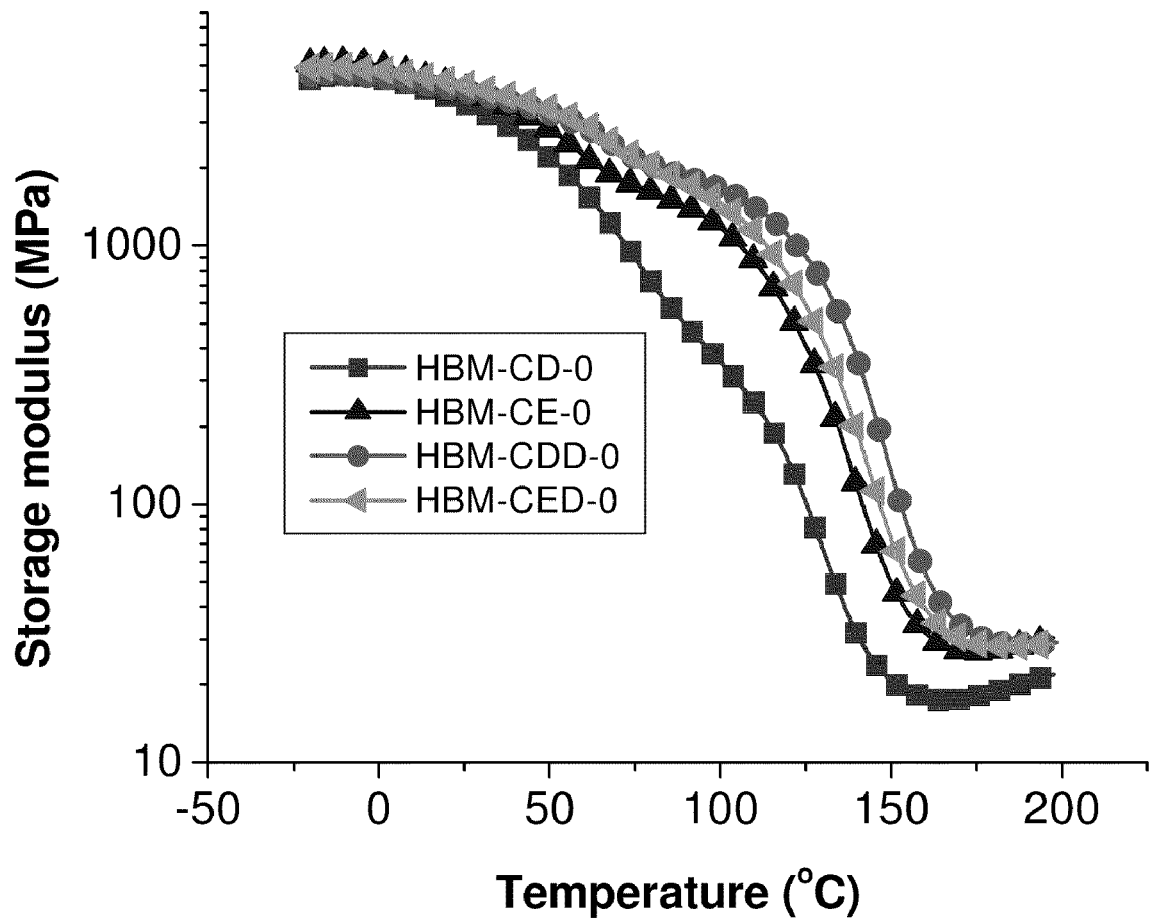
Figure 14E:
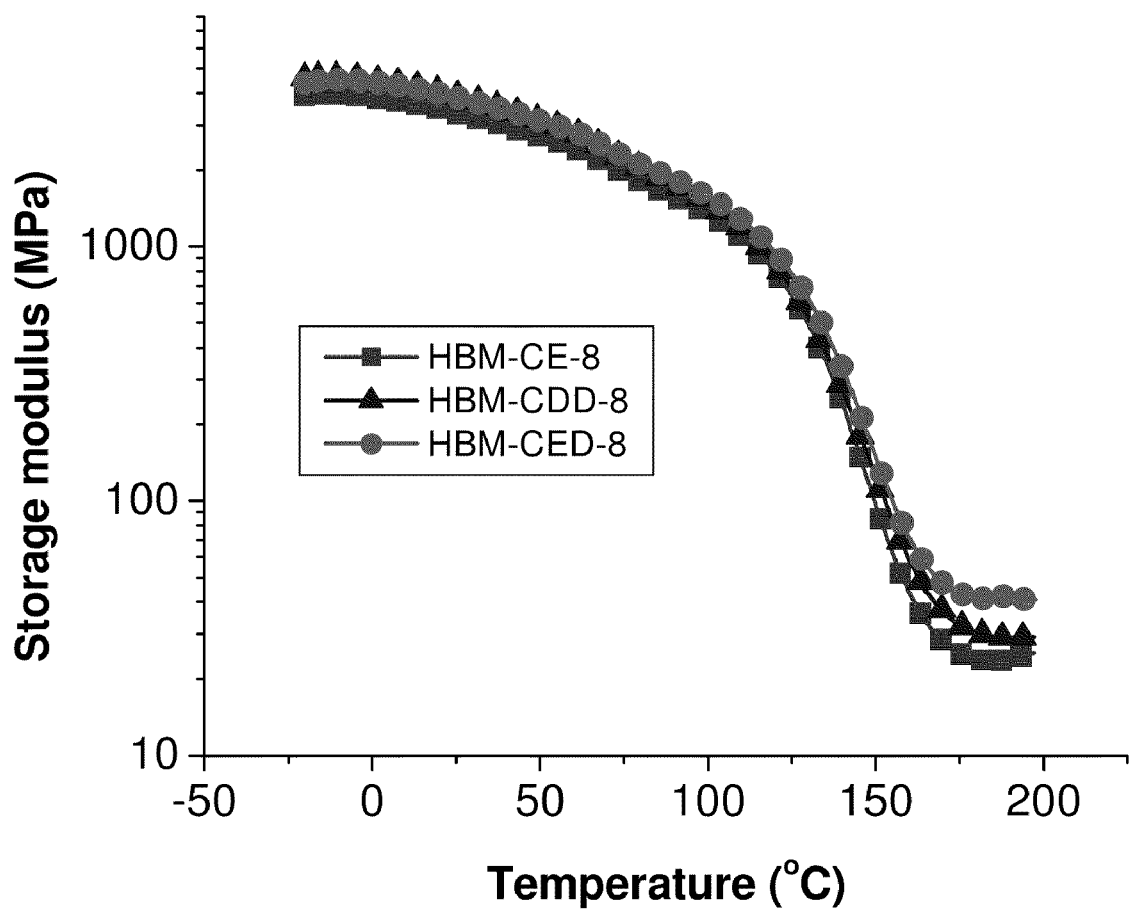
Figure 14F:
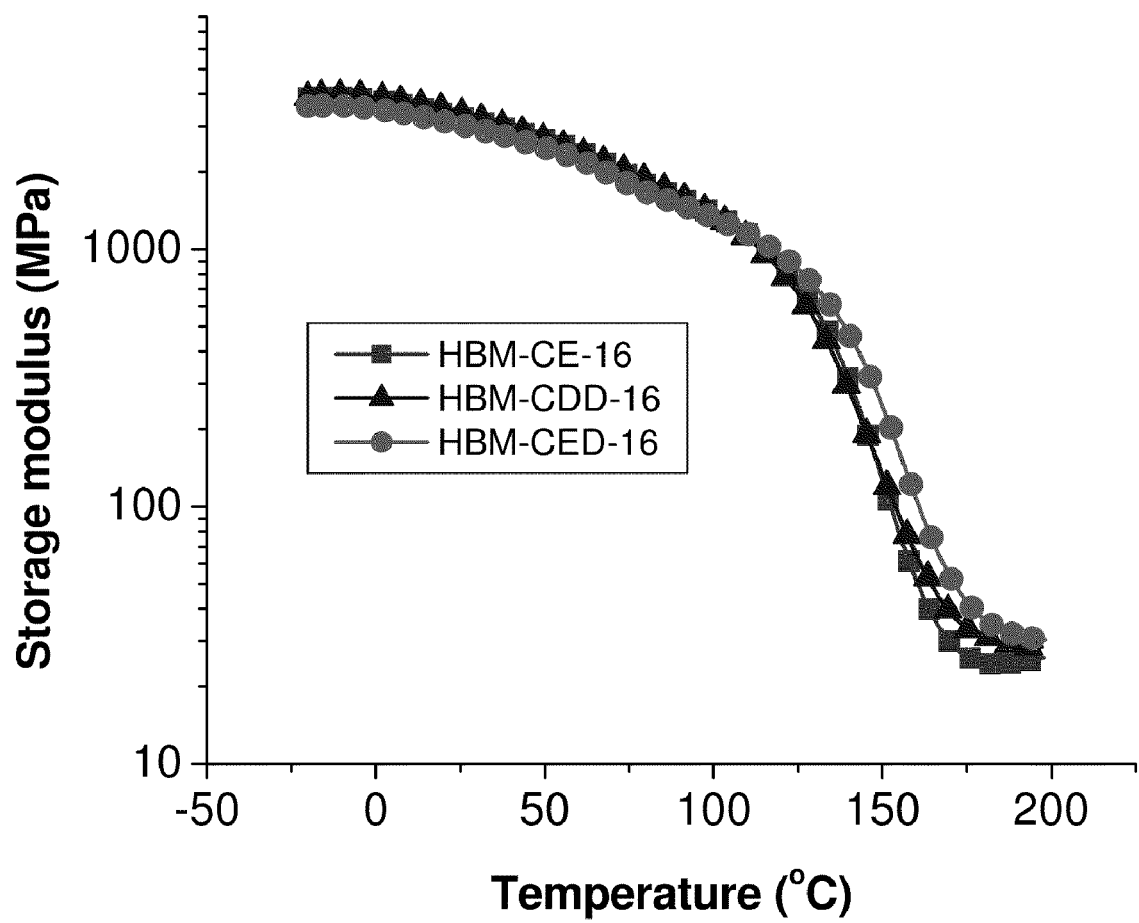

FIGS. 14D-14F show the representative storage modulus of adhesives containing different photoinitiator systems and water content as a function of temperature. Storage modulus values for polymer networks cured in the absence of water are in the range of 3.3~3.7 GPa at 37° C. and in the range of 20~31 MPa at temperatures in the rubbery plateau region.

Figure 14G:
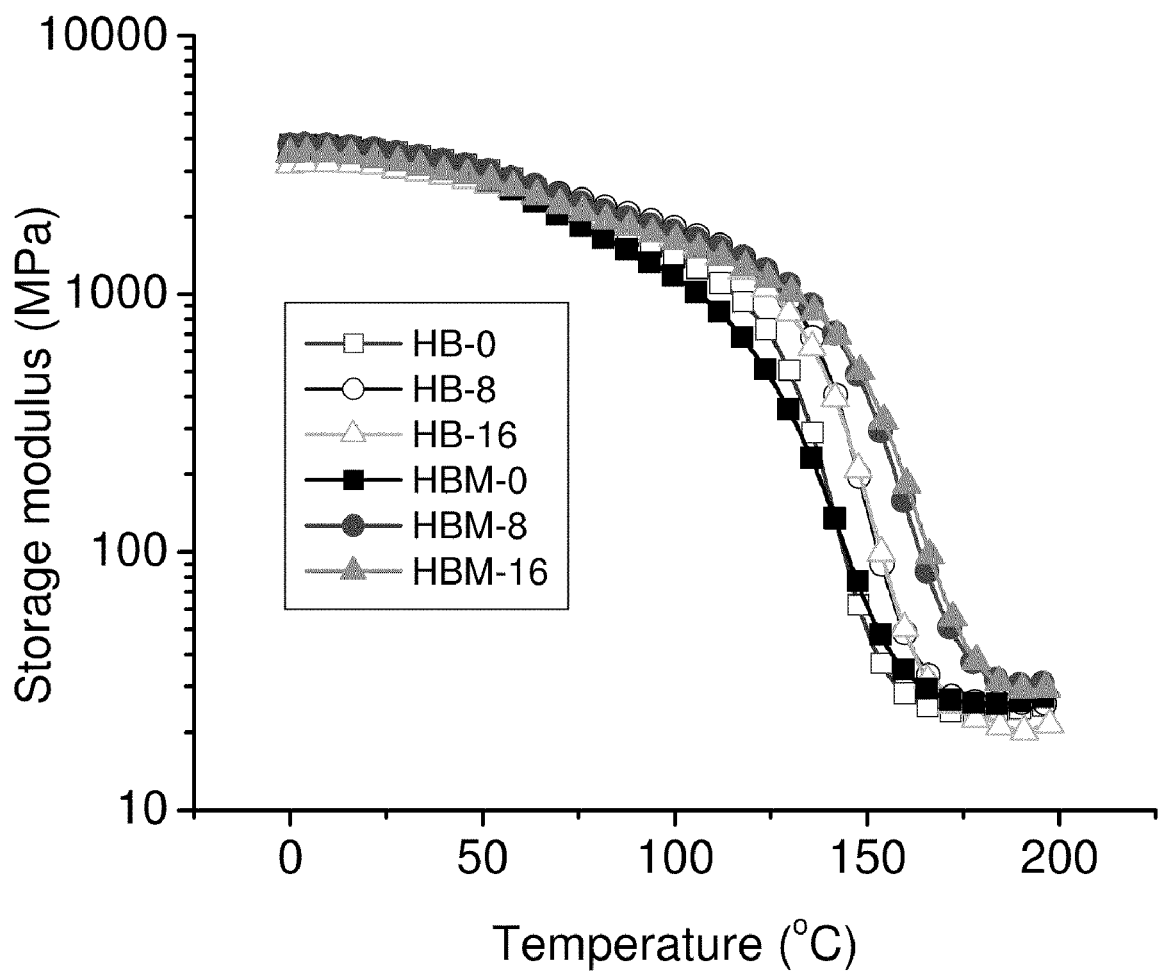
Figure 14H:
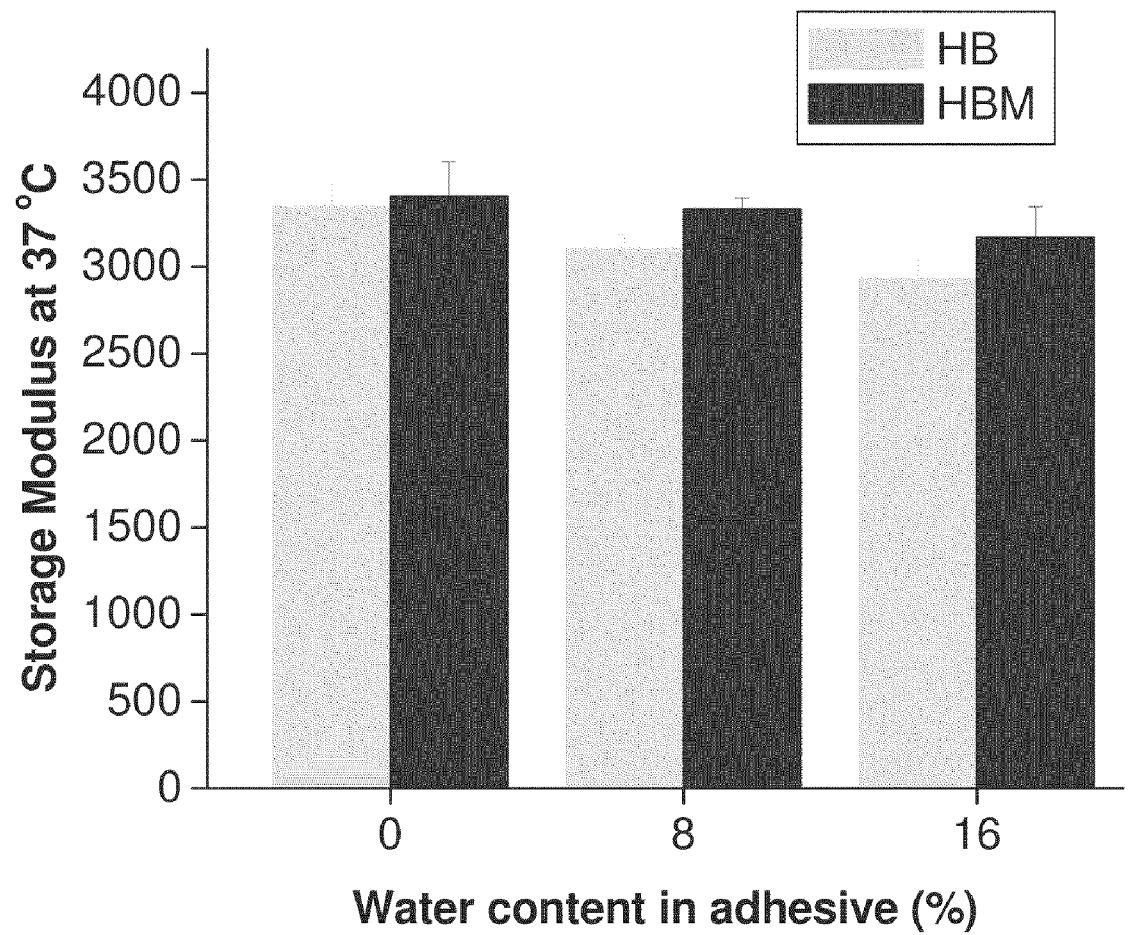

As shown in FIGS. 14G-14H, at very low temperature, all tested copolymers dropped their storage modulus slowly when temperature was raised. As temperature was further raised reaching the glass transition region (around 150° C.), their modulus drastically dropped. As heating continued, storage modulus stopped dropping, reaching the plateau. These are equilibrium storage moduli which do not change their values up to the beginning of the thermal decomposition of the polymer. Storage modulus at 37° C. is not significantly different for both control and experimental adhesives. These rubbery moduli values are related to the crosslinking density of the materials. In this study, the plateau in the rubbery region is used as a measure of crosslinking density. The results showed higher rubbery modulus in HBM system, as compared to HB system.

Figure 15A:
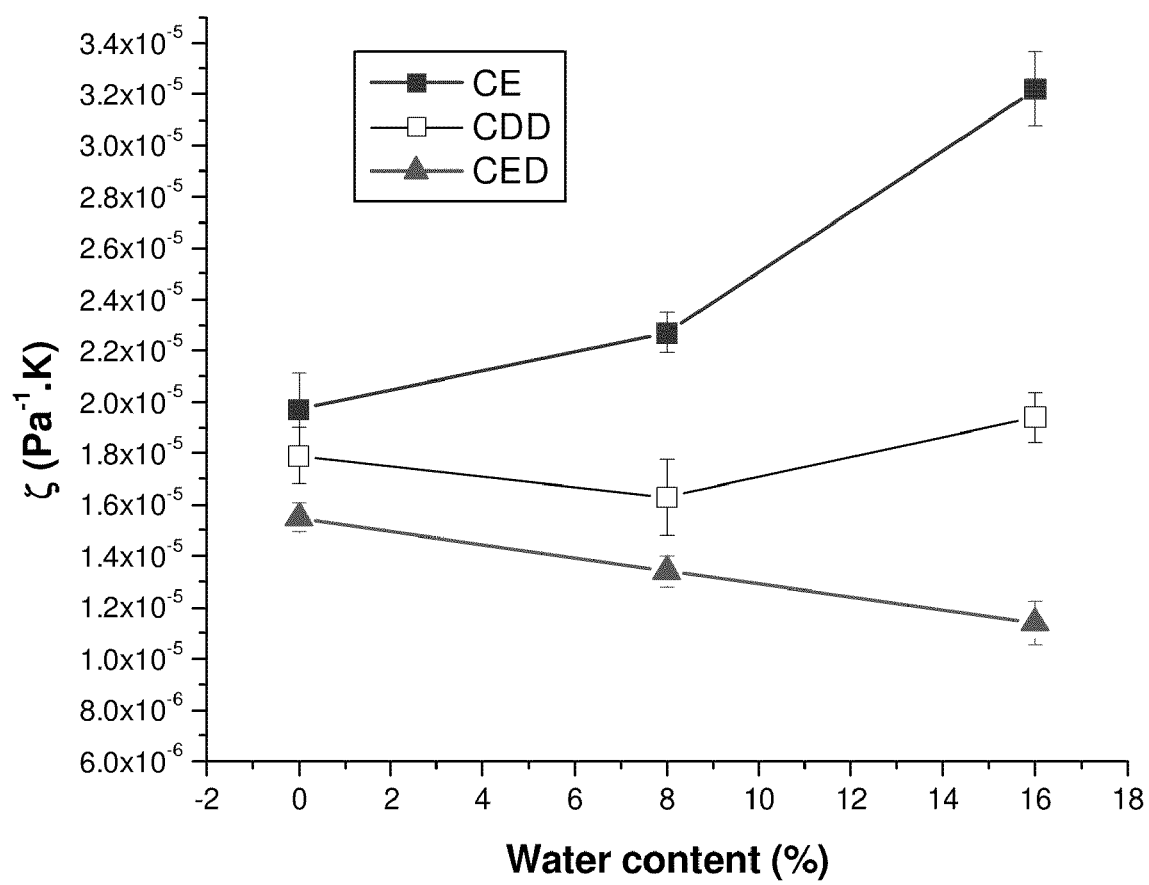
FIGS. 15A-15C are graphs that show the representative inverse ratio ($\zeta$) of the modulus in the rubbery region to temperature at which the modulus was measured plotted as a function of water content (%) in adhesives. $\zeta$ is inversely related to the crosslinking density of the copolymer. (Reference: Kannurpatti A et al. Polymer 39:2507, 1998).

FIG. 15A shows the inverse ratio (ζ) of the modulus in the rubbery region to the temperature at which the modulus was measured as a function of water content (%). The ζ value for the three-component system is less than that of two-component system (FIG. 15). Interestingly, the ζ value for the CQ/EDMAB system increases with increasing water content, but generally decreases with increasing water content for the three-component systems. The lowest ζ values are observed for CQ/EDMAB/DPIHP photocured in the presence of 16% water, suggesting higher crosslink density in this resin. The difference between CQ/EDMAB and CQ/EDMAB/DPIHP is greatest at the highest water content (16%).

Figure 15B:
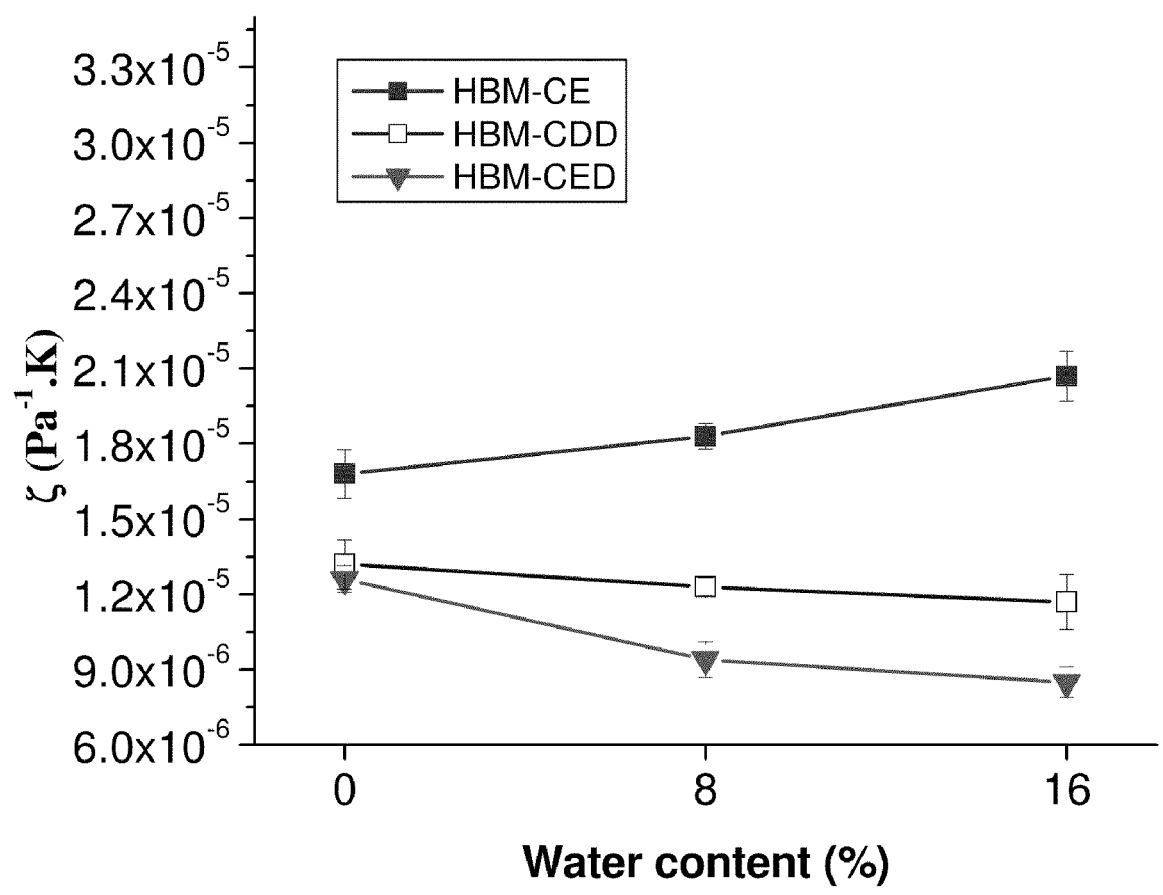

FIG. 15B shows the inverse ratio (ζ) of the modulus in the rubbery region to the temperature at which the modulus was measured as a function of water content (%). The ζ value for the three-component system (HBM-CDD and HBM-CED) is less than that of two-component system (HBM-CE). Interestingly, the ζ value for the CQ/EDMAB system increases with increasing water content, but generally decreases with increasing water content for the three-component systems. The lowest ζ values are observed for CQ/EDMAB/DPIHP photocured in the presence of 16% water, suggesting higher crosslink density in this resin. The difference between CQ/EDMAB and CQ/EDMAB/DPIHP is greatest at the highest water content (16%).

Figure 15C:
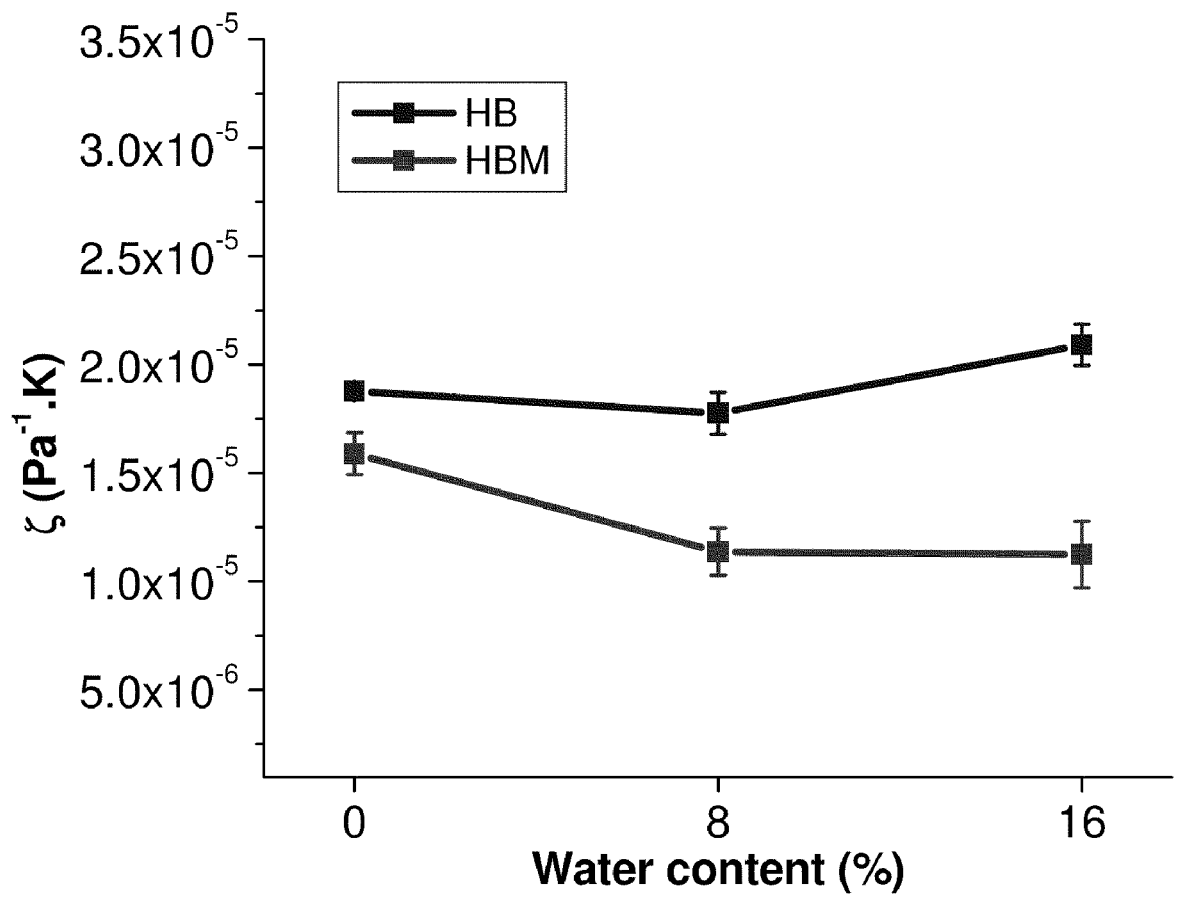

FIG. 15A shows the inverse ratio ($\zeta$) of HEMA/Bis-GMA=45/55 resin composition on the photoinitiator effect and FIG. 15B shows the inverse ratio of HEMA/BisGMA/MPE resin composition on the photoinitiator effect. As you can see from both figures, CED (CQ/EDMAB/DPIHP) photoinitiator system shows the lowest inverse ratio and decreases with water contents. FIG. 15C should be eliminated because it was determined from different light source.

The storage modulus indicates a change from a glassy state to the rubbery state over the temperature range. At very low temperature, all the samples tested show gradual decreases in storage moduli with increasing temperature. Near the glass transition, storage moduli decrease drastically. As heating continues, all the samples reach the rubbery plateau, in which storage modulus is insensitive to further increases in temperature. Among the photoinitiator systems tested, the three-component CQ/EDMAB/DPIHP system exhibited the highest rubbery modulus regardless of water content, while the comparable two-component system (i.e., CQ/EDMAB) showed significantly lower rubbery modulus in the presence of water. This rubbery modulus value has been related to the crosslink density of the material. The ratio of rubbery modulus to the absolute temperature at which that modulus was measured, $\zeta$, is inversely related to the crosslink density of the polymer network and is directly proportional to the molecular weight between crosslinks. By this measure, the adhesives formulated with the aromatic amine (EDMAB) as a co-initiator and DPIHP as a third component showed higher crosslink density than those formulated with the aliphatic amine and a two-component initiator system (Table 2), an implication consistent with the DC, Tg, and storage modulus results.

Thus, the results presented here suggest that DMAEMA is a less efficient photoreducer than EDMAB, leading to lower DC and dynamic mechanical properties. This behavior may be attributed to the fact that DMAEMA is more prone to combine with oxygen than aromatic amines. In addition, since DMAEMA carries a methacrylate group with a double bond, DMAEMA-dimer or oligomers may be formed in the presence of radicals. The addition of DPIHP to the two-component photoinitiator systems increased the final degree of conversion, Tg, storage modulus, and crosslink density, especially in the presence of water. The enhanced properties observed in the presence of the iodonium salt, DPIHP may be due in part to its ability to generate an active phenyl radical. As an electron acceptor, the iodonium salt abstracts an electron from the inactive CQ neutral radical, regenerating the original CQ and producing a diphenyliodonium radical. The diphenyliodonium radical rapidly fragments into a molecule of phenyl iodide and a phenyl radical that is very active in initiating the polymerization. In addition, since DPIHP is ionic in nature as a salt, it may increase the compatibility between amphiphilic monomers (i.e., having both hydrophilic and hydrophobic characteristics) and initiators, especially in the presence of water. The results indicate that the performance of photoinitiator systems can be quite sensitive to the presence of water, and thus should be evaluated under both dry and wet conditions.

13.
Effective bonding at the prepared tooth/composite material interface requires dentin adhesives that provide superior properties and rapid polymerization under clinical conditions. The reactivity and the mechanical behavior are influenced by the photoinitiator system and curing conditions. The aim of this study was to determine the effect of photoinitiator systems on dynamic mechanical properties of dentin adhesives. The adhesive formulation: HEMA, bisGMA 45/55 w/w was cured in the presence of 0 (A0), 8 (A8) and 16 (A16) wt % $H_2O$ to simulate wet bonding. The photoinitiators were: camphorquinone (CQ) as a photosensitizer, 2-(dimethylamino)ethyl methacrylate (DMAEMA) and ethyl-4-(dimethylamino)benzoate (EDMAB) as co-initiator and diphenyliodonium hexafluorophosphate (DPIHP). Beam specimens (1×1×11 $mm^3$) were used for measurement of dynamic mechanical properties (TA Instruments Q800) and degree of conversion (LabRAM ARAMIS Raman spectrometer). The adhesives were cured for 40 s at 25° C. with commercial visible-light, (Spectrum® 800, Dentsply, Milford, Del., USA), Intensity=550 mW $cm^{-2}$. DC ranged from 75-97% increasing w $H_2O$ content. The CQ/DMAEMA system was gel-like in $H_2O$, but DPIHP addition led to comparable rubbery moduli in all systems regardless of water content. Tg-° C. and storage moduli in the rubbery region ($E_r'$-MPa). The addition of DPIHP to either the CQ/EDMAB or the CQ/DMAEMA photoinitiator system improved the polymerization conversion, Tg and rubbery moduli of the polymer networks formulated in water to simulate wet bonding. Table 3 shows the results of the study.

14.
New adhesives, containing hydroxyethyl methacrylate (HEMA), bisGMA (bisphenol-A diglycidyl ether dimethacrylate) in addition to MPE, 45/30/25 w/w, were light polymerized in the presence of 0, 8, 16 wt % $H_2O$ and compared to control adhesives [HEMA/bisGMA, 45/55 w/w, at 0, 8, 16 wt % $H_2O$]. Property characterization included degree of conversion (DC) by Raman spectroscopy and thermomechanical analysis ($T_g$, storage modulus in the rubbery region ($E_r'$), tan delta) using a dynamic mechanical analyzer (TA Instruments Q800, three-point bending clamp). For enzymatic degradation, adhesive discs were prewashed for 3 days, incubated in phosphate buffer w/wo porcine liver esterase (PLE) for 8 days; supernatants were collected daily and analyzed for methacrylic acid (MAA) by HPLC. In the presence of 16 wt % $H_2O$, the properties are shown in Table 4. Formulated in the presence of water, the higher storage modulus in the rubbery region and increased $T_g$ indicate notable increase in crosslink density in the new adhesive. When polymerized in the presence of water to simulate the wet oral environment, dentin adhesives containing new multifunctional monomer with urethane linkage showed higher crosslink density and significantly less MAA release indicating greater esterase resistance relative to HEMA/bisGMA controls.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein by specific reference in their entirety.

TABLES

TABLE 1

Mechanical Properties of Adhesive Resins

| Sample | Water Content (wt %) | Storage and Test Condition | Toughness (MN/m$^3$) | Elongation (%) | Ultimate Tensile Strength (MPa) | Modulus of Elasticity (GPa) |
|---|---|---|---|---|---|---|
| 2A0 | 0 | In air[a] | 2.5 (0.1) | 0.08 (0.01) | 44.6 (0.3) | 1.00 (0.16) |
|  |  | In water[b] | 5.2 (2.5) | 0.12 (0.02) | 37.6 (2.5) | 0.62 (0.11) |

TABLE 1-continued

Mechanical Properties of Adhesive Resins

| Sample | Water Content (wt %) | Storage and Test Condition | Toughness (MN/m³) | Elongation (%) | Ultimate Tensile Strength (MPa) | Modulus of Elasticity (GPa) |
|---|---|---|---|---|---|---|
| 2A0T | 0 | In air | 2.7 (0.6) | 0.06 (0.01) | 45.7 (0.3) | 1.18 (0.02) |
|  |  | In water | 6.1 (2.6) | 0.11 (0.02) | 45.1 (2.5) | 0.80 (0.11) |
| 2A8 | 8 | In air | 1.7 (0.7) | 0.07 (0.02) | 38.1 (0.3) | 0.78 (0.20) |
|  |  | In water | 2.7 (0.2) | 0.08 (0.02) | 33.6 (0.9) | 0.70 (0.02) |
| 2A8T | 8 | In air | 2.6 (0.2) | 0.09 (0.01) | 49.0 (3.0) | 0.91 (0.07) |
|  |  | In water | 4.1 (1.6) | 0.11 (0.02) | 47.6 (1.3) | 0.80 (0.05) |
| 2A16 | 16 | In air | 1.3 (0.3) | 0.06 (0.01) | 37.0 (0.8) | 0.77 (0.02) |
|  |  | In water | 1.9 (0.1) | 0.11 (0.01) | 32.4 (0.8) | 0.69 (0.05) |
| 2A16T | 16 | In air | 2.9 (0.5) | 0.10 (0.02) | 46.4 (0.8) | 0.89 (0.07) |
|  |  | In water | 2.9 (0.3) | 0.14 (0.03) | 45.6 (1.5) | 0.78 (0.06) |

[a] 24 hr storage in air at room temperature after polymerization, the specimens were subjected to mechanical testing under dry conditions.
[b] 24 hr storage in air at room temperature and 24 hr storage in water and then tested while wet after polymerization.

TABLE 2

Degree of Conversion Values and Curing Time of Adhesive Resins Containing Different Photoinitiator Systems and Different Water Content

| Samples | Photoinitiator system[a] | Water content (%) | DC (%)[b] | CT (sec)[c] |
|---|---|---|---|---|
| CD-0 | CQ/DMAEMA | 0 | 74.7 (0.4) | 33 (0.7) |
| CD-8 | CQ/DMAEMA | 8 | 37.9 (3.4) | n/a[c] |
| CD-16 | CQ/DMAEMA | 16 | 37.8 (1.3) | n/a |
| CE-0 | CQ/EDMAB | 0 | 84.9 (0.6) | 9 (0.5) |
| CE-8 | CQ/EDMAB | 8 | 85.2 (0.4) | 19 (0.5) |
| CE-16 | CQ/EDMAB | 16 | 89.7 (0.2) | 18 (0.5) |
| CDD-0 | CQ/DMAEMA/DPIHP | 0 | 88.0 (0.6) | 7 (0.4) |
| CDD-8 | CQ/DMAEMA/DPIHP | 8 | 93.9 (0.7) | 5 (0.4) |
| CDD-16 | CQ/DMAEMA/DPIHP | 16 | 95.7 (0.5) | 7 (0.4) |
| CED-0 | CQ/EDMAB/DPIHP | 0 | 92.4 (1.4) | 5 (0.4) |
| CED-8 | CQ/EDMAB/DPIHP | 8 | 97.2 (0.4) | 5 (0.4) |
| CED-16 | CQ/EDMAB/DPIHP | 16 | 97.3 (0.7) | 5 (0.4) |

The adhesive resin composition used in this study consisted of HEMA/BisGMA = 45/55 wt %.
[a] Abbreviations: CQ = Camphorquinone; DMAEMA = 2-(dimethylamino)ethyl methacrylate; EDMAB = ethyl-4-(dimethylamino) benzoate; DPIHP = diphenyliodonium hexafluorophosphate.
[b] DC was determined by using a LabRAM ARAMIS Raman spectrometer.
[c] The curing time was taken as the period from which the light exposure was initiated to the moment at which the metal rod could not be moved by hand. The data are presented as mean values with standard deviations in parentheses, and the number of specimens tested for DC and CT is 4.
[c] CT could not be measured because the cured polymer was gel-like due to its low DC.

TABLE 3

| Formulation | Initiator | 0% H₂O (SD) Tg | 0% H₂O (SD) $E_r'$ | 8% H₂O (SD) Tg | 8% H₂O (SD) $E_r'$ | 16% H₂O (SD) Tg | 16% H₂O (SD) $E_r'$ |
|---|---|---|---|---|---|---|---|
| F1 | CQ/DMAEMA | 139 (1.1) | 23.2 (0.8) | — | — | — | — |
| F2 | CQ/EDMAB | 143 (2.2) | 22.5 (1.1) | 138 (3.1) | 19.5 (1.4) | 130 (1.0) | 13.8 (0.7) |
| F3 | CQ/DMAEMA/DPIHP | 152 (0.2) | 25.2 (1.7) | 151 (2.1) | 27.6 (2.1) | 155 (1.6) | 23.3 (1.2) |
| F4 | CQ/EDMAB/DPIHP | 150 (0.4) | 28.6 (0.7) | 156 (2.8) | 33.0 (1.1) | 159 (1.7) | 38.9 (1.6) |

TABLE 4

| Property | New (SD) | Control (SD) |
|---|---|---|
| DC (%) | 95.4 (0.3) | 89.7 (0.2) |
| $T_g$ (° C.) | 157 (0.7) | 130 (1.0) |
| $E_r'$ (MPa) | 23.4 (2.5) | 13.9 (1.3) |
| Tan delta | 0.62 (0.01) | 0.67 (0.02) |
| MAA (µg/mL) | 268.7 (009.8) | 585.7 (131.7) |
|  | $p < 0.05$ |  |

TABLE 5

| Samples | DC (%) | Tg (° C.) | Tan $\delta_{max}$ | Half-width (° C.) of tandelta peak |
|---|---|---|---|---|
| HB-0 | 91.3 (0.2) | 145.5 (0.8) | 0.68 (0.01) | 29.81 (0.63) |
| HB-8 | 96.3 (0.3) | 155.0 (2.4) | 0.70 (0.02) | 30.44 (1.06) |
| HB-16 | 95.6 (0.8) | 156.2 (1.4) | 0.68 (0.01) | 32.06 (0.53) |
| HBM-0 | 91.9 (0.3) | 146.3 (1.9) | 0.54 (0.01) | 41.76 (0.79) |
| HBM-8 | 96.3 (0.3) | 162.5 (0.4) | 0.60 (0.02) | 33.94 (1.69) |
| HBM-16 | 97.6 (0.2) | 167.1 (0.7) | 0.58 (0.02) | 31.36 (1.02) |

Abbreviations

1. CQ : Camphorquinone
2. DMAEMA: 2-(dimethylamino)ethyl methacrylate
3. EDMAB: ethyl-4-(dimethylamino)benzoate
4. DPIHP: diphenyliodonium hexafluorophosphate
5. HB: HEMA/BisGMA=45/55 wt %
6. HBM: HEMA/BisGMA/MPE=45/30/25 wt %
7. HB-0: HEMA/BisGMA=45/55 wt % +0 wt % water
8. HB-8: HEMA/BisGMA=45/55 wt % +8wt % water
9. HB-16: HEMA/BisGMA=45/55 wt % +16wt % water
10. HBM-0: HEMA/BisGMA/MPE=45/30/25 wt % +0 wt % water
11. HBM-8: HEMA/BisGMA/MPE=45/30/25 wt % +8wt % water
12. HBM-16: HEMA/BisGMA/MPE=45/30/25 wt % +16wt % water
13. HBM-CD-0: HBM-0+CQ (0.5wt %)/DMAEMA (0.5wt %)
14. HBM-CE-0: HBM-0+CQ (0.5wt %)/EDMAB (0.5wt %)
15. HBM-CDD-0: HBM-0+CQ (0.5wt %)/DMAEMA (0.5wt %)/DPIHP (0.5wt %)
16. HBM-CED-0: HBM-0+CQ (0.5wt %)/EDMAB (0.5wt %)/DPIHP (0.5wt %)
17. HBM-CD-8: HBM-8+CQ (0.5wt %)/DMAEMA (0.5wt %)
18. HBM-CE-8: HBM-8+CQ (0.5wt %)/EDMAB (0.5wt %)

19. HBM-CDD-8: HBM-8+CQ (0.5wt %)/DMAEMA (0.5wt %)/DPIHP (0.5wt %)
20. HBM-CED-8: HBM-8+CQ (0.5wt %)/EDMAB (0.5wt %)/DPIHP (0.5wt %)
21. HBM-CD-16: HBM-16+CQ (0.5wt %)/DMAEMA (0.5wt %)
22. HBM-CE-16: HBM-16+CQ (0.5wt %)/EDMAB (0.5wt %)
23. HBM-CDD-16: HBM-16+CQ (0.5wt %)/DMAEMA (0.5wt %)/DPIHP (0.5wt %)
24. HBM-CED-16: HBM-16+CQ (0.5wt %)/EDMAB (0.5wt %)/DPIHP (0.5wt %)
25. CD-0=CQ/DMAEMA (Resin composition: HEMA/Bis-GMA=45/55wt %+0 wt % water)
26. CE-0=CQ/EDMAB (Resin composition: HEMA/Bis-GMA=45/55wt %+0 wt % water)
27. CDD-0=CQ/DMAEMA/DPIHP (Resin composition: HEMA/BisGMA=45/55wt %+0 wt % water)
28. CED-0=CQ/EDMAB/DPIHP (Resin composition: HEMA/BisGMA=45/55wt %+0 wt % water)
29. CE-8, CDD-8, CED-8 and CE-16, CDD-16, and CED-16 are the same as above, but different water content, 8% and 16%.
30. HBM-CD-0=CQ/DMAEMA (Resin composition: HEMA/BisGMA/MPE=45/30/25 wt %+0 wt % water)
31. HBM-CE-0=CQ/EDMAB (Resin composition: HEMA/BisGMA/MPE=45/30/25 wt %+0 wt % water)
32. HBM-CDD-0=CQ/DMAEMA/DPIHP (Resin composition
33. HEMA/BisGMA/MPE=45/30/25 wt %+0 wt % water)
34. HBM-CED-0=CQ/EDMAB/DPIHP (Resin composition
35. HEMA/BisGMA/MPE=45/30/25 wt %+0 wt % water)

The invention claimed is:
1. A dental composition, comprising:
a dental composition filler;
a monomer that polymerizes to form a polymer suitable for use in dentistry, said monomer comprising:
a structure as shown in Formula 1 or derivative thereof:

Formula 1

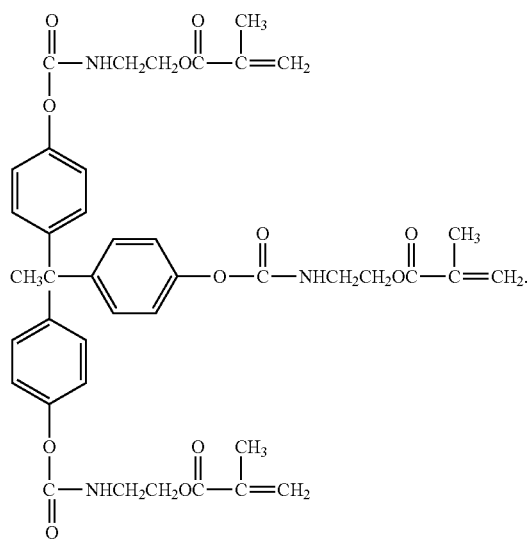

2. A composition as in claim 1, wherein the monomer consists essentially of the structure of Formula 1.
3. A dental composition as in claim 1, comprising a polymer produced from the polymerization of the monomer having the structure of formula 1.
4. A composition as in claim 1, further comprising one or more co-monomers.
5. A composition as in claim 4 wherein the one or more co-monomers are selected from monomers or oligomers having one or more ethylenically unsaturated groups, di- acrylates and methacrylates, tri- acrylates and methacrylates poly-acrylates and methacrylates, 2-hydroxyethyl methacrylate (HEMA), methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, diurethane dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol ("Bis-GMA"), bis[1-(2-acryloxy)]-p-ethoxyphenyldimethylmethane, bis[1-(3-acryloxy-2-hydroxy)]-p-propoxyphenyldimethylmethane, trishydroxyethyl-isocyanurate trimethacrylate, the bis-acrylates and bis-methacrylates of polyethylene glycols of molecular weight 200-500, copolymerizable mixtures of acrylated monomers, copolymerizable acrylated oligomers, phosphoric acid derivatives and carboxylic acid derivatives of ethylenically unsaturated monomers, vinyl compounds, styrene, diallyl phthalate, divinyl succinate, divinyl adipate and divinylphthalate, and combinations thereof.
6. A composition as in claim 5, wherein the one or more co-monomers are 2-hydroxyethyl methacrylate (HEMA) and bisphenol A dimethacrylate (BisGMA).
7. A composition as in claim 6, wherein the composition includes HEMA/BisGMA/MPE at 45/30/25 w/w ratio, where MPE is 1,1,1-tri-[4-(methacryloxyethylaminocarbonyloxy)-phenyl]ethane .
8. A composition as in claim 6, wherein the composition includes HEMA/BisGMA/MPE+40 wt % EtOH, where MPE is 1,1,1-tri[4-(methacryloxyethylaminocarbonyloxy)-phenyl]ethane.
9. A composition as in claim 4, further comprising a photoinitiator system.
10. A composition as in claim 9, wherein the photoinitiator system includes a component selected from the group of acylphosphine oxides, bis-acyl phospine oxides, camphorquinone, benzophenone, alkyl ethers of benzoin, diphenoxy benzophenone, benzildimethylketal, halogenated functional benzophenones, amino functional benzophenones, benzils, benzimidazozles, 2-hydroxy-2-methylphenol-1-propanone, fluorenone, fluorenone derivatives, 2,2-diethoxyacetophenone, benzoin, 9,10-phenanthrenequinone, anthraquinone derivatives, 2-benzyl-2-N,N-dimethylamino-1-(f -morpholinophenyl)butanone, zanthone, zanthone derivatives, halogenated acetophenone, halogenated acetophenone derivatives, thioxanthone, thioxanthone derivatives, sulfonyl chlorides of aromatic compounds, diacetyl, furil, anisil, 4,4'-dichlorobenzil, 4,4'-dialkoxybenzil, phenylpropanedione, acylphosphine oxides, 2-(dimethylamino) ethyl methacrylate, diphenyliodonium hexafluorophosphate, diphenyliodonium chloride, ethyl -4-(dimethylamino) benzoate, or combinations thereof.
11. A composition as in claim 9, wherein the photoinitiator system includes an iodonium salt.
12. A composition as in claim 11, wherein the iodonium salt is selected from the group of diphenyliodonium hexafluorophosphate and diphenyliodonium chloride.
13. A dental composition, comprising:
a monomer, that polymerizes to form a polymer suitable for use in dentistry, said monomer comprising:
a structure as shown in Formula 1 or derivative thereof:

Formula 1

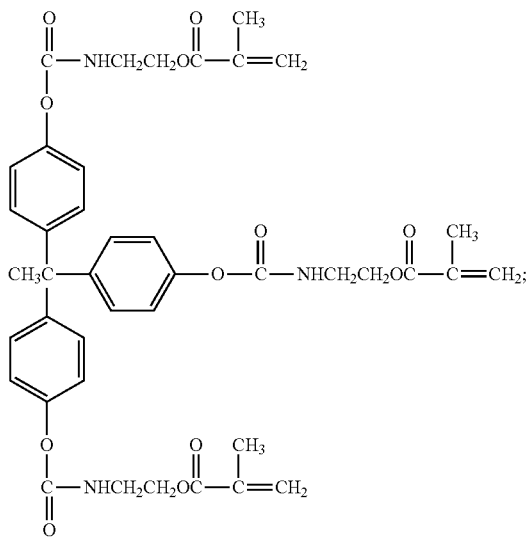

and a photoinitiator system, wherein the photoinitiator system includes camphorquinone, ethyl-4-(dimethylamino) benzoate, and diphenyliodonium hexafluorophosphate or camphorquinone, 2-(dimethylamino) ethyl methacrylate, and diphenyliodonium hexafluorophosphate.

14. A composition as in claim 9, wherein the photoinitiator system is included at a total amount of 0.001 wt % to about 10 wt %.

15. A composition as in claim 12, wherein the composition includes camphorquinone at about 0.5 wt % and ethyl-4-(dimethylamino) benzoate at about 0.5 wt %).

16. A composition as in claim 12, wherein the composition includes camphorquinone from about 0.1 to about 1 wt %, ethyl-4-(dimethylamino) benzoate from 0.1 to about 1 wt %, and iodonium salt from about 0.1 to about 1 wt %.

17. A dental composition comprising a polymer prepared from polymerizing the monomer of claim 13.

18. A dental composition as in claim 17, wherein the polymer is prepared from polymerizing one or more co-monomers.

19. A dental composition as in claim 18, wherein the one or more co-monomers are selected from monomers or oligomers having one or more ethylenically unsaturated groups, di- acrylates and methacrylates, tri- acrylates and methacrulates, poly-acrylates and methacrylates, methyl acrylate, 2-hydroxyethyl methacrylate (HEMA), methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, diurethane dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol ("Bis -GMA"), bis[1-(2-acryloxy)]-p-ethoxyphenyldimethylmethane, bis[1-(3-acryloxy-2-hydroxy)]-p-propoxyphenyldimethylmethane, trishydroxyethyl-isocyanurate trimethacrylate, the bis-acrylates and bis-methacrylates of polyethylene glycols of molecular weight 200-500, copolymerizable mixtures of acrylated monomers, copolymerizable acrylated oligomers, phosphoric acid derivatives and carboxylic acid derivatives of ethylenically unsaturated monomers, vinyl compounds, styrene, diallyl phthalate, divinyl succinate, divinyl adipate and divinylphthalate, and combinations thereof.

20. A method of preparing a dental composition comprising:
polymerizing the monomer of claim 1.

21. A method as in claim 20, wherein the monomer is polymerized in a mouth of a subject.

22. A method as in claim 21, further comprising polymerizing one or more co-monomers with the monomer.

23. A method as in claim 22, wherein the one or more co-monomers are selected from monomers or oligomers having one or more ethylenically unsaturated groups, di- acrylates and methacrylates, tri- acrylates and methacrulates, poly-acrylates and methacrylates, 2-hydroxyethyl methacrylate (HEMA), methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, diurethane dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol ("Bis-GMA"), bis[1-(2-acryloxy)]-p-ethoxyphenyldimethylmethane, bis[1-(3-acryloxy-2-hydroxy)]-p-propoxyphenyldimethylmethane, trishydroxyethyl-isocyanurate trimethacrylate, the bis-acrylates and bis-methacrylates of polyethylene glycols of molecular weight 200-500, copolymerizable mixtures of acrylated monomers, copolymerizable acrylated oligomers, phosphoric acid derivatives and carboxylic acid derivatives of ethylenically unsaturated monomers, vinyl compounds, styrene, diallyl phthalate, divinyl succinate, divinyl adipate and divinylphthalate, and combinations thereof.

24. A method as in claim 22, further comprising polymerizing the monomer and co-monomers with a photoinitiator system.

25. A method as in claim 24, wherein the photoinitiator system includes a component selected from the group of acylphosphine oxides, bis-acyl phospine oxides, camphorquinone, benzophenone, alkyl ethers of benzoin, diphenoxy benzophenone, benzildimethylketal, halogenated functional benzophenones, amino functional benzophenones, benzils, benzimidazozles, 2-hydroxy-2-methylphenol-1-propanone, fluorenone, fluorenone derivatives, 2,2-diethoxyacetophenone, benzoin, 9,10-phenanthrenequinone, anthraquinone derivatives, 2-benzyl-2-N,N-dimethylamino-1-(f -morpholinophenyl)butanone, zanthone, zanthone derivatives, halogenated acetophenone, halogenated acetophenone derivatives, thioxanthone, thioxanthone derivatives, sulfonyl chlorides of aromatic compounds, diacetyl, furil, anisil, 4,4'-dichlorobenzil, 4,4'-dialkoxybenzil, phenylpropanedione, acylphosphine oxides, 2-(dimethylamino) ethyl methacrylate, diphenyliodonium hexafluorophosphate, diphenyliodonium chloride, ethyl-4-(dimethylamino) benzoate, or combinations thereof.

26. A method as in claim 24, wherein the photoinitiator system includes a iodonium salt.

27. A method as in claim 26, wherein the iodonium salt is selected from the group of diphenyliodonium hexafluorophosphate and diphenyliodonium chloride.

28. A method as in claim 24, wherein the photoinitiator system includes camphorquinone, ethyl-4-(dimethylamino) benzoate, and diphenyliodonium hexafluorophosphate or camphorquinone, 2-(dimethylamino) ethyl methacrylate, and diphenyliodonium hexafluorophosphate.

29. A method of making the monomer of claim 1, comprising chemical synthesis of 1,1,1-tri[4-(methacryloxyethylaminocarbonyloxy)-phenyl]ethane (MPE) by reaction of 1,1,1-tris(4-hydroxyphenyl)ethane and 2-isocyantoethyl methacrylate.
30. A method as in claim 29, wherein the chemical synthesis is as follows:
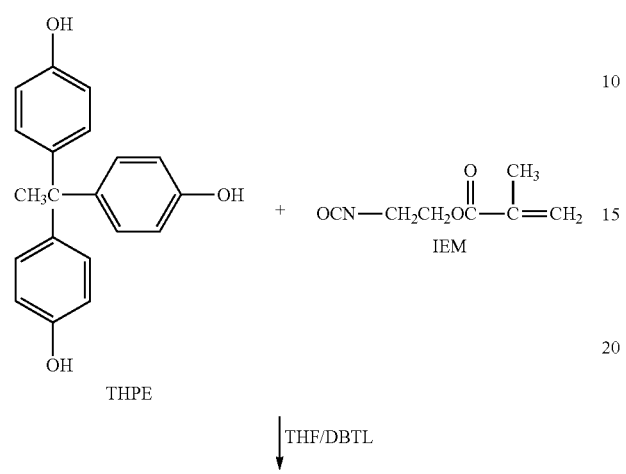
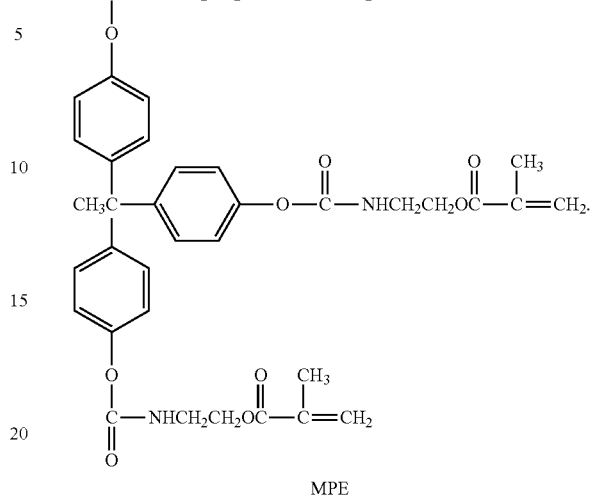
* * * * *